(12) United States Patent
Caroff et al.

(10) Patent No.: US 8,058,263 B2
(45) Date of Patent: Nov. 15, 2011

(54) SUBSTITUTED 2-PHENYL-PYRIDINE DERIVATIVES

(75) Inventors: Eva Caroff, Ranspach-le-Haut (FR); Kurt Hilpert, Hofstetten (CH); Francis Hubler, Hegenheim (FR); Emmanuel Meyer, Aarau (CH); Dorte Renneberg, Basel (CH)

(73) Assignee: Actelion Pharmaceuticals Ltd, Allschwil (CH)

( * ) Notice: Subject to any disclaimer, the term of this patent is extended or adjusted under 35 U.S.C. 154(b) by 0 days.

(21) Appl. No.: 12/936,661

(22) PCT Filed: Apr. 9, 2009

(86) PCT No.: PCT/IB2009/051499
§ 371 (c)(1),
(2), (4) Date: Oct. 6, 2010

(87) PCT Pub. No.: WO2009/125366
PCT Pub. Date: Oct. 15, 2009

(65) Prior Publication Data
US 2011/0046089 A1   Feb. 24, 2011

(30) Foreign Application Priority Data
Apr. 11, 2008   (WO) .................. PCT/IB2008/051384

(51) Int. Cl.
*A61K 31/675* (2006.01)
*C07F 9/6509* (2006.01)
(52) U.S. Cl. .......................................... 514/85; 544/337
(58) Field of Classification Search .......................... None
See application file for complete search history.

(56) References Cited

U.S. PATENT DOCUMENTS

| | | |
|---|---|---|
| 6,855,715 B1 | 2/2005 | Liebeschuetz et al. |
| 2003/0060474 A1 | 3/2003 | Bryant et al. |
| 2005/0038037 A1 | 2/2005 | Bryant et al. |
| 2005/0065163 A1 | 3/2005 | Bryant et al. |
| 2008/0194576 A1 | 8/2008 | Caroff et al. |
| 2008/0234272 A1 | 9/2008 | Binkert et al. |
| 2010/0261678 A1 | 10/2010 | Caroff et al. |

FOREIGN PATENT DOCUMENTS

| | | |
|---|---|---|
| EP | 0 407 200 A1 | 1/1991 |
| JP | 53-073586 | 6/1978 |
| WO | WO 02/098856 | 12/2002 |
| WO | WO 2004/052366 | 6/2004 |
| WO | WO 2004052366 | 6/2004 |
| WO | WO 2004/092189 | 10/2004 |
| WO | WO 2006/114774 | 11/2006 |
| WO | WO 2008/044217 | 4/2008 |
| WO | WO 2008/050301 | 5/2008 |
| WO | WO 2009/069100 | 6/2009 |
| WO | WO 2009/080226 | 7/2009 |
| WO | WO 2009/080227 | 7/2009 |
| WO | WO 2009/125365 | 10/2009 |
| WO | WO 2009/125366 | 10/2009 |
| WO | WO 2010/116328 | 10/2010 |
| WO | WO 2010/122504 | 10/2010 |

OTHER PUBLICATIONS

Norgard, Expert Opin. Invest.Drugs vol. 18(8), pp. 1219-1230 (2009).*
Bartoli, G., et al., "Reaction of Dianions of Acyclic β-Enamino Ketones with Electrophiles. 3. Nitriles: Synthesis of Pyridine and Pyrimidine Derivatives", J. Org. Chem., vol. 57, pp. 6020-6025, (1992).
Furstner, A., et al., "Iron-Catalyzed Cross-Coupling Reactions", J. Am. Chem. Soc., vol. 124, pp. 13856-13863, (2002).
Gould, P.L., "Salt Selection for Basic Drugs", International Journal of Pharmaceutics, vol. 33, pp. 201-217, (1986).
Parlow, J.J., et al., "Piperazinyl-glutamate-pyridines as Potent Orally Bioavailble P2Y12 Antagonists for Inhibition of Platelet Aggregation", Bioorganic & Medicinal Chemistry Letters, vol. 19, pp. 4657-4663, (2009).
Parlow, J.J., et al., "Piperazinyl-glutamate-pyrimidines as Potent P2Y12 Antagonists for Inhibition of Platelet Aggregation", Bioorganic & Medicinal Chemistry Letters, vol. 19, pp. 6148-6156, (2009).
Remington, The Science and Practice of Pharmacy, 21st Edition (2005), Part 5, "Pharmaceutical Manufacturing" [published by Lippincott Williams & Wilkins].
Shao, B., et al., "Phenoxyphenyl Pyridines as Novel State-Dependent, High-Potency Sodium Channel Inhibitors", J. Med. Chem., vol. 47, pp. 4277-4285, (2004).
Amir, J., et al., "Treatment of Thrombotic Thrombocytopenic Pupura with Antiplatelet Drugs", Blood, vol. 42, No. 1, pp. 27-33 Jul. 1973.

(Continued)

*Primary Examiner* — Emily Bernhardt
(74) *Attorney, Agent, or Firm* — Hoxie & Associates LLC

(57) ABSTRACT

The present invention relates to compounds of formula I

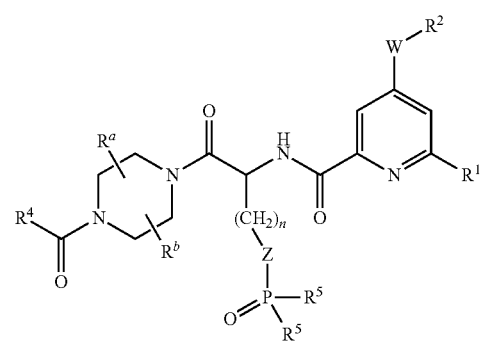

wherein $R^1$, $R^2$, $R^4$, $R^5$, $R^a$, $R^b$, n, W and Z are as defined in the application, their preparation and their use as $P2Y_{12}$ receptor antagonists in the treatment and/or prevention of peripheral vascular, of visceral-, hepatic- and renal-vascular, of cardiovascular and of cerebrovascular diseases or conditions associated with platelet aggregation, including thrombosis in humans and other mammals.

19 Claims, No Drawings

OTHER PUBLICATIONS

Antithrombotic Trialists' Collaboration, "Collaborative Meta-Analysis of Randomised Trials of Antiplatelet Therapy for Prevention of Death, Myocardial Infarction, and Stroke in High Risk Patients", British Medical Journal, vol. 324, pp. 71-86, 2002.

Balduini, C.L., et al., "Platelet Aggregation in Platelet-Rich Plasma and Whole Blood in 120 Patients with Myeloproliferative Disorders", Coagulation and Transfusion Medicine, vol. 95, No. 1, pp. 82-86, Jan. 1991.

Bertrand, Michel. E., "Randomized Multicenter Comparison of Conventional Anticoagulation Versus Antiplatelet Therapy in Unplanned and Elective Coronary Stenting: . . . " Circulation, vol. 98, pp. 1597-1603, 1998.

Born G.V.R., et al., "The Aggregation of Blood Platelets", J. Physiol., vol. 168, pp. 178-195, (1963).

Brighton, T.A., et al., "Antiphospholipid Antibodies and Thrombosis", Bailliere's Clinical Haematology, vol. 7, No. 3, pp. 541-557, Sep. 1994.

Caprie Steering Committee, "A randomized, blinded, trial of clopidogrel versus aspirin in patients at risk of ischaemic events (CAPRIE)", The Lancet, vol. 348, pp. 1329-1339, Nov. 16, 1996.

Collins, C.E. et al., "Review Article:Platelets in Inflammatory Bowel Diease-Pathogenic Role and Therapeutic Implications", Aliment Pharmacol. Ther., vol. 11, pp. 237-247, 1997.

Database Chemcats, Chemical Abstracts Service, Columbus, OH, USA; XP002420714; Order No. (ON) CGX-3221820.

Database Chemcats, Chemical Abstracts Service, Columbus, OH, USA; XP002420715; Order No. (ON): 15569369, 15467386.

Davies, M.J., et al., "Intramyocardial Platelet Aggregation in Patients with Unstable Angina Suffering Sudden Ischemic Cardiac Death", Pathophysiology and Natural History—Platelets, Circulation, vol. 73, No. 3, pp. 418-427, 1986.

Felfernig-Boehm, D., et al., "Early Detection of Preeclampsia by Determination of Platelet Aggregability", Thrombosis Research, vol. 98, pp. 139-146, 2000.

Feokistov et al., "Adenosine A2B receptors, Pharmacological Reviews", vol. 49, No. 4, pp. 381-402, 1997.

Fox, K.A.A., et al. Benefits and Risks of the Combination of Clopidogrel and Aspirin in Patients Undergoing Surgical Revascularization for Non-ST-Elevation Acute Coronary Syndrome: The Clidogrel in Unstable Angina to Prevent Recurrent Ischemic Events (CURE) Trial, Circulation, vol. 110, pp. 1202-1208, 2004.

Halushka, P.V., et al., "Protective Effects of Aspirin in Endotoxic Shock", The Journal of Pharmacology and Experimental Therapeutics, vol. 218, No. 2, pp. 464-469, 1981.

Hovens, M.M.C., et al., "Aspirin in the Prevention and Treatment of Venous Thromboembolism", Journal of Thrombosis and Haemostasis, vol. 4, pp. 1470-1475, 2006.

Iyer, R.P., et al., "Synthesis of Iodoalkylacylates and their Use in the Preparation of S-Alkyl Phosphorothiolates", Synthetic Communications, vol. 25(18), pp. 2739-2749, (1995).

Kharbanda, R.K., et al., "Prevention of Inflammation-Induced Endothelial Dysfunction: A Novel Vascula-Protective Action of Aspirin", Circulation, vol. 105, pp. 2600-2604, 2002.

Megalopoulos, a., et al., "Recurrent Arterial Thromboses in a Woman with Heparin Induced Thrombocytopenia, Successfully Managed with Iloprost Followed by Clopidogrel. An Alternative Therapeutic Option for Heparin Induced Thrombocytopenia Type II Syndrome", International Angiology, vol. 25, No. 1, pp. 84-89, Mar. 2006.

Mehta, S.R., et al., "Effects of Pretreatment with Clopidogrel and Aspirin Followed by Long-Term Therapy in Patients Undergoing Percutaneous Coronary Intervention: The PCI-CURE Study", The Lancet, vol. 358, pp. 527-533, Aug. 18, 2001.

Office Action dated Oct. 28, 2010, U.S. Appl. No. 11/912,545.

Office Action dated Jan. 29, 2011, U.S. Appl. No. 12/445,352.

Parlow, John J. et al., "Piperazinyl-glutamate-pyrimidines as potent $P2Y_{12}$ antagonists for inhibition of platelet aggregation", 2009, Bioorganic & Medicinal Chemistry Letters, pp. 6148-6156.

Payne, D.A., et al., "Beneficial Effects of Clopidogrel Combined with Aspirin in Reducing Cerebral Emboli in Patients Undergoing Carotid Endarterectomy", Circulation, vol. 109, pp. 1476-1481, 2004.

Stathakis, N.E., et al., Platelet Dysfunction in Essential Thrombocythaemia, Annals of Clinical Research, vol. 6, pp. 198-202, 1974.

Thorsen, C. A., et al., "The Treatment of the Hemolytic-Uremic Syndrome with Inhibitors, of Platelet Function", The American Journal of Medicine, vol. 66, pp. 711-716, Apr. 1979.

Triadou, P., et al., "Platelet Function in Sickle Cell Disease During Steady State", Nouvelle Revue Francaise Hematologie, vol. 32, pp. 137-142, 1990.

University of Perugia, "Aspirin for the Prevention of Recurrent Venous Thromboembolism and Cardiovascular Events", pp. 1-3, ClinicalTrials.gov/ct/show/NCT00222677, Sep. 13, 2005.

Yao, S., et al., "Clopidogrel is More Effective Than Aspirin as Adjuvant Treatment to Prevent Reocclusion After Thrombolysis", Am. J. Physiol., vol. 267, pp. H488-H493, 1994.

* cited by examiner

SUBSTITUTED 2-PHENYL-PYRIDINE DERIVATIVES

CROSS REFERENCE TO RELATED APPLICATIONS

This application is a United States Application under 35 U.S.C. 371 claiming benefit of PCT Application No. PCT/IB2009/051499, filed on Apr. 9, 2009, which claims the benefit of PCT Application No. PCT/IB2008/051385, filed on Apr. 11, 2008, the contents of each of which are incorporated herein by reference.

FIELD OF THE INVENTION

The present invention relates to certain substituted 2-phenyl-pyridine derivatives and their use as $P2Y_{12}$ receptor antagonists in the treatment and/or prevention of peripheral vascular, of visceral-, hepatic- and renal-vascular, of cardiovascular and of cerebrovascular diseases or conditions associated with platelet aggregation, including thrombosis in humans and other mammals.

BACKGROUND OF THE INVENTION

Haemostasis is referred to as the natural balance of maintaining the fluidity of the blood in the vascular system and preventing excessive blood loss subsequent to blood vessel injury by rapid formation of a solid blood clot. After vascular damage, contraction of the vessels and platelet adhesion occur immediately followed by aggregation of the platelets, activation of the coagulation cascade and finally also of the fibrinolytic system. Haemostatic abnormalities can lead to excessive bleeding or thrombosis, both life-threatening situations.

A series of antiplatelet agents have been developed over the past several years based on different mechanisms of action. The most widely used agent in antiplatelet therapy is aspirin, which irreversibly inhibits cyclooxygenase-1 and thereby affecting the thromboxane pathway. Although not optimally efficacious, treatment with aspirin remains the standard therapy against which new therapeutics are compared and judged.

Other drugs like the phosphodiesterase inhibitors dipyridamole and cilostazol, as well as the vitamin K antagonists (warfarin), are marketed but do not show all desirable features for such drugs. Three intravenously applicable, potent GPIIb/IIIa receptor antagonists (abciximab, eptifibatide, and tirofiban) blocking platelet aggregation are available on the market. Besides, some orally active GPIIb/IIIa antagonists (e.g. sibrafiban, xemilofiban or orbofiban) have not been successful in clinical development so far.

Adenosine 5'-diphosphate (ADP) is a key mediator in platelet activation and aggregation interfering with two platelet ADP receptors $P2Y_1$ and $P2Y_{12}$.

Antagonists of the platelet ADP receptor have been identified and display inhibition of platelet aggregation and antithrombotic activity. The most effective antagonists known so far are the thienopyridines ticlopidine, clopidogrel and CS-747, which have been used clinically as antithrombotic agents. It could be shown that these drugs, via their reactive metabolites, irreversibly block the ADP receptor subtype $P2Y_{12}$.

Some $P2Y_{12}$ antagonists like AR-C69931MX (Cangrelor) or AZD6140 have reached phase III clinical studies. These inhibitors are selective platelet ADP receptor antagonists, which inhibit ADP-dependent platelet aggregation, and are effective in vivo.

piperazino-carbonylmethylaminocarbonyl-naphtyl or -quinolyl derivatives have been described as ADP receptor antagonists in WO 02/098856 and WO 2004/052366.

WO 2006/114774 describes 2-phenyl-4-(carbonylmethylaminocarbonyl)-pyrimidine derivatives as $P2Y_{12}$ receptor antagonists and WO 2008/044217 describes 2-phenyl-6-(carbonylmethylaminocarbonyl)-pyridine derivatives as $P2Y_{12}$ receptor antagonists. However all these compounds do not contain any phosphonic acid or phosphonate motif.

DESCRIPTION OF THE INVENTION

The inventors have now found that the substituted 2-phenyl-pyridine derivatives according to the present invention surprisingly show significantly improved biological properties compared to the corresponding carboxylic acid derivatives previously known to one skilled in the art.

Various embodiments of the invention are presented hereafter:

i) The present invention firstly relates to the compounds of formula I

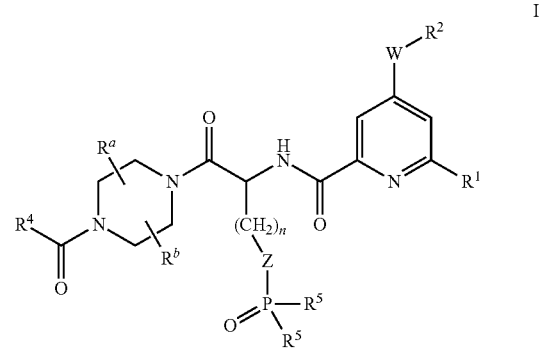

wherein
$R^1$ represents phenyl optionally substituted 1 to 3 times (preferably optionally substituted once or twice and more preferably optionally substituted once) by substituents each independently selected from the group consisting of halogen, methyl, methoxy, trifluoromethyl and trifluoromethoxy;
W represents a bond and $R^2$ represents alkyl, cycloalkyl, aryl or heteroaryl; or
W represents —O— and $R^2$ represents alkyl, hydroxyalkyl, alkoxyalkyl or heterocyclyl; or
W represents —NR$^3$—, $R^2$ represents alkyl, carboxyalkyl, hydroxyalkyl, alkoxyalkyl, heterocyclyl, cycloalkyl, aryl or aralkyl and $R^3$ represents hydrogen or alkyl; or
W represents —NR$^3$— and $R^2$ and $R^3$ form, together with the nitrogen that carries them, a heterocyclic ring of 4 to 7 members wherein the members needed to complete said heterocyclic ring are each independently selected from —CH$_2$—, —CHR$^x$—, —O—, —S—, —CO— and —NR$^y$—, it being understood however that said heterocyclic ring does not contain more than one member selected from the group consisting of —CHR$^x$—, —O—, —S—, —CO— and —NR$^y$—, $R^x$ representing hydroxy, hydroxymethyl, alkoxymethyl or alkoxy and $R^y$ representing hydrogen or alkyl;
$R^a$ represents hydrogen or methyl;
$R^b$ represents hydrogen or methyl;
$R^4$ represents alkoxy;

$R^5$ represents hydroxy, $R^6$—OCH$_2$O— or $R^7$-alkyl-NH—;
$R^6$ represents alkylcarbonyl or alkoxycarbonyl;
$R^7$ represents alkoxycarbonyl;
n represents 0, 1, 2 or 3 and Z is a bond or n is 1 and Z is phenyl (the —P(O)(R$^5$)$_2$ group being preferably in para position in this case);
and to the salts (in particular pharmaceutically acceptable salts) of such compounds.

The compounds of formula I may contain one or more stereogenic or asymmetric centers, such as one or more asymmetric carbon atoms. The compounds of formula I may thus be present as mixtures of stereoisomers or preferably as pure stereoisomers. Mixtures of stereoisomers may be separated in a manner known to a person skilled in the art.

The compounds of formula I are P2Y$_{12}$ receptor antagonists. Accordingly, they are useful in therapy (including combination therapy), where they can be widely used as inhibitors of platelet activation, aggregation and degranulation, as promoters of platelet disaggregation or as anti-thrombotic agents.

The following paragraphs provide definitions of the various chemical moieties for the compounds according to the invention. Said definitions are intended to apply uniformly throughout the specification and claims unless an otherwise expressly set out definition provides a broader or narrower definition.

The term "halogen" refers to fluorine, chlorine, bromine or iodine, preferably to fluorine, chlorine or bromine and more preferably to fluorine.

The term "alkyl", used alone or in combination, refers to a saturated straight or branched chain alkyl group containing 1 to 7 carbon atoms (e.g. methyl, ethyl, n-propyl, iso-propyl, n-butyl, iso-butyl, sec-butyl, tert-butyl, n-pentyl, neopentyl, iso-pentyl, n-hexyl, iso-hexyl, n-heptyl or iso-heptyl), and preferably 1 to 4 carbon atoms. Representative examples of preferred alkyl groups include methyl, ethyl, propyl, iso-propyl, n-butyl, iso-butyl, sec-butyl and tert-butyl. The term "(C$_x$-C$_y$)alkyl" (x and y being integers) refers to a straight or branched chain alkyl group containing x to y carbon atoms.

The term "alkoxy", used alone or in combination, refers to a saturated straight or branched chain alkoxy group containing 1 to 6 carbon atoms (e.g. methoxy, ethoxy, n-propoxy, iso-propoxy, n-butoxy, iso-butoxy, sec-butoxy, tert-butoxy, n-pentoxy, neopentyloxy, iso-pentyloxy, n-hexyloxy or iso-hexyloxy), and preferably 1 to 4 carbon atoms. Representative examples of preferred alkoxy groups include methoxy, ethoxy, n-propoxy, iso-propoxy, n-butoxy, iso-butoxy, sec-butoxy and tert-butoxy. The term "(C$_x$-C$_y$)alkoxy" (x and y being integers) refers to a straight or branched chain alkoxy group containing x to y carbon atoms.

The term "hydroxyalkyl", as used herein, refers to an alkyl group as previously defined wherein one hydrogen atom has been replaced by a hydroxy (i.e. —OH) group. Examples of hydroxyalkyl groups include, but are not limited to, hydroxymethyl, 2-hydroxy-ethyl, 2-hydroxy-propyl, 2-hydroxy-1-methyl-ethyl, 2-hydroxy-1,1-dimethyl-ethyl, 1-hydroxy-propyl, 3-hydroxy-propyl, 1-hydroxy-butyl, 3-hydroxy-butyl, 4-hydroxy-butyl, 3-hydroxy-pentyl and 3-hydroxy-3-methyl-butyl.

The term "alkoxyalkyl", as used herein, refers to an alkyl group as previously defined wherein one hydrogen atom has been replaced by an alkoxy group as previously defined. Examples of alkoxyalkyl groups include, but are not limited to, methoxymethyl and 2-methoxy-ethyl.

The term "cycloalkyl", as used herein, alone or in any combination, refers to a saturated cyclic hydrocarbon moiety containing 3 to 7 carbon atoms which may be substituted once by hydroxy, hydroxymethyl, alkoxymethyl (preferably methoxymethyl or ethoxymethyl and more preferably methoxymethyl) or alkoxy (preferably methoxy or ethoxy and more preferably methoxy). Representative examples of cycloalkyl groups include, but are not limited to, cyclopropyl, cyclobutyl, cyclopentyl, cyclohexyl, 4-hydroxy-cyclohexyl, 2-hydroxy-cyclohexyl, 2-hydroxymethyl-cyclopropyl and 2-methoxymethyl-cyclopropyl (in particular cyclopropyl, 2-hydroxymethyl-cyclopropyl and 2-methoxymethyl-cyclopropyl).

The term "carboxyalkyl" refers to an alkyl group as previously defined wherein one hydrogen atom has been replaced by a carboxy group (that is, by a —COOH group). Representative examples of carboxyalkyl groups include, but are not limited to, 2-carboxy-ethyl and 3-carboxy-propyl.

The term "aryl" refers to an aromatic cyclic group with one, two or three rings, having from 6 to 14 carbon ring-atoms and preferably from 6 to 10 carbon ring-atoms, for example to phenyl or naphthyl groups (and notably to phenyl groups). Any aryl group (and in particular any phenyl group) as defined herein may be substituted with one, two or more substituents (preferably with one to three substituents, more preferably with one or two substituents and notably with one substituent), each independently selected from the group consisting of halogen, alkyl and alkoxy. Specific examples of aryl groups are phenyl, 2-fluorophenyl, 3-fluorophenyl, 4-fluorophenyl, 2-chlorophenyl, 3-chlorophenyl, 4-chlorophenyl, 2-methoxyphenyl, 3-methoxyphenyl, 4-methoxyphenyl, 2-methylphenyl, 3-methylphenyl, 4-methylphenyl, 2,4-difluorophenyl, 3,4-difluorophenyl, 2,4-dimethoxyphenyl and 2,4-dimethylphenyl. Preferred examples are phenyl and 4-methoxyphenyl.

The term "aralkyl", as used herein, alone or in any combination, refers to an aryl group appended to the parent molecular moiety through an alkyl group wherein however the aryl group may be unsubstituted or substituted with 1 to 3 substituents selected independently from the group consisting of halogen, alkyl and alkoxy. Representative examples of aralkyl groups include, but are not limited to, benzyl, 2-phenylethyl, 3-phenylpropyl and 2-naphth-2-ylethyl. Preferred aralkyl groups are the phenylalkyl groups.

The term "phenylalkyl", as used herein, alone or in any combination, refers to an unsubstituted phenyl group appended to the parent molecular moiety through an alkyl group. Representative examples of phenylalkyl groups include, but are not limited to, benzyl, 2-phenylethyl and 3-phenylpropyl.

The term "heteroaryl", as used herein, alone or in combination, refers to a mono-, bi- or tricyclic aromatic ring system containing up to 14 ring atoms wherein at least one of the rings contains at least one heteroatom independently selected from the group consisting of nitrogen, oxygen and sulfur; in addition, the term "heteroaryl" may also refer to 1-oxy-pyridinyl groups. The heteroaryl group can be unsubstituted or substituted with 1 to 3 substituents (preferably 1 to 2 substituents and more preferably 1 substituent) selected independently from the group consisting of halogen, alkyl, alkoxy, trifluoromethyl and trifluoromethoxy. Representative examples of heteroaryl groups include, but are not limited to, thienyl, furanyl, pyrrolyl, pyrazolyl, thiazolyl, imidazolyl, oxazolyl, pyridinyl, 1-oxy-4-pyridinyl, 1-oxy-3-pyridinyl, 1-oxy-2-pyridinyl, pyrimidinyl, quinolinyl, benzimidazolyl, benzothiazolyl, benzothienyl, benzoxazolyl, benzofuranyl, indolyl, carbazolyl, phenothiazinyl and phenoxazinyl.

The term "monocyclic heteroaryl", as used herein, refers to a monocyclic aromatic ring system containing 5 or 6 ring atoms among which 1 or 2 may be heteroatoms selected from O, N and S. The monocyclic heteroaryl group can be unsubstituted or substituted with 1 to 2 substituents (preferably 1 substituent) selected independently from the group consisting of halogen, alkyl, alkoxy, trifluoromethyl and trifluoromethoxy. Representative examples of monocyclic heteroaryl groups include, but are not limited to, thienyl, furanyl, pyrrolyl, pyrazolyl, thiazolyl, imidazolyl, oxazolyl, pyridinyl and pyrimidinyl.

The term "heterocyclyl", as used herein, alone or in any combination, refers to an unsubstituted saturated monocyclic moiety of 3 to 7 ring members (and preferably 4 to 6 ring members) containing 1 to 2 heteroatoms selected from nitrogen, oxygen and sulfur, it being however understood that (i) a heterocyclyl group is not attached to the rest of the molecule by a nitrogen atom, (ii) a heterocyclyl group of 3 or 4 ring members contains only one heteroatom which is a nitrogen atom and (iii) a heterocyclyl group does not contain 2 sulfur atoms. The sulfur atom of a heterocyclyl group may be in an oxidised form, i.e. as a sulfoxide or sulfonyl. Representative examples of heterocyclyl groups include, but are not limited to, azetidinyl, pyrrolidinyl, tetrahydrofuranyl, piperidinyl, piperazinyl, morpholinyl and thiomorpholinyl.

Further definitions of additional chemical moieties for the compounds according to the invention are given below. Said definitions are intended to apply uniformly throughout the specification and claims unless an otherwise expressly set out definition provides a broader or narrower definition.

The term "alkoxymethyl", as used herein, refers to a methyl group wherein one hydrogen atom has been replaced by an alkoxy group as previously defined. Examples of alkoxymethyl groups include, but are not limited to, methoxymethyl and ethoxy-methyl.

The term "$R^7$-alkyl-NH—", as used herein, refers to an amino group wherein one hydrogen atom has been replaced by an alkyl group as previously defined (and preferably a ($C_1$-$C_4$)alkyl group), wherein the alkyl group is substituted with $R^7$. Preferably the substituent $R^7$ and the nitrogen atom of the amino group are attached to the same carbon atom of the alkyl group. Examples of $R^7$-alkyl-NH— groups include, but are not limited to, 1-alkoxycarbonyl-ethylamino and notably 1-ethoxycarbonyl-ethylamino.

The term "alkylcarbonyl", as used herein, refers to a carbonyl group which is substituted with an alkyl group as previously defined. Examples of alkylcarbonyl groups include, but are not limited to, methylcarbonyl(acetyl) and ethylcarbonyl. Preferred is acetyl.

The term "alkoxycarbonyl", as used herein, refers to a carbonyl group which is substituted with an alkoxy group as previously defined. Examples of alkoxycarbonyl groups include, but are not limited to, methoxycarbonyl and ethoxycarbonyl. Preferred is ethoxycarbonyl.

Besides, the following paragraphs provide definitions of various other terms. Said definitions are intended to apply uniformly throughout the specification and claims unless an otherwise expressly set out definition provides a broader or narrower definition.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively the term "around") placed before a temperature "Y" refers in the current application to an interval extending from the temperature Y minus 10° C. to Y plus 10° C., and preferably to an interval extending from Y minus 5° C. to Y plus 5° C.

ii) In particular, the invention relates to compounds of formula I that are also compounds of formula $I_P$

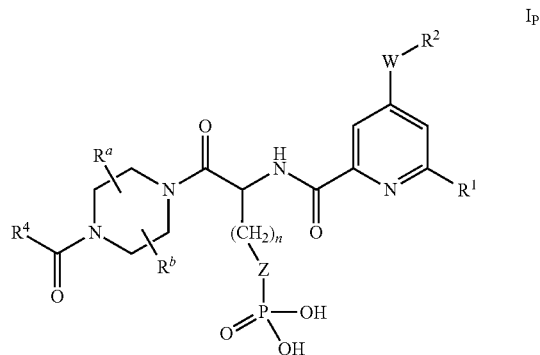

wherein $R^1$ represents phenyl optionally substituted 1 to 3 times (preferably optionally substituted once or twice and more preferably optionally substituted once) by substituents each independently selected from the group consisting of halogen, methyl, methoxy, trifluoromethyl and trifluoromethoxy;

W represents a bond and $R^2$ represents alkyl, cycloalkyl, aryl or heteroaryl; or W represents —O— and $R^2$ represents alkyl, hydroxyalkyl, alkoxyalkyl or heterocyclyl; or W represents —$NR^3$—, $R^2$ represents alkyl, carboxyalkyl, hydroxyalkyl, alkoxyalkyl, heterocyclyl, cycloalkyl, aryl or aralkyl and $R^3$ represents hydrogen or alkyl; or W represents —$NR^3$— and $R^2$ and $R^3$ form, together with the nitrogen that carries them, a heterocyclic ring of 4 to 7 members wherein the members needed to complete said heterocyclic ring are each independently selected from —$CH_2$—, —$CHR^x$—, —O—, —S—, —CO— and —$NR^y$—, it being understood however that said heterocyclic ring does not contain more than one member selected from the group consisting of —$CHR^x$—, —O—, —S—, —CO— and —$NR^y$—, $R^x$ representing hydroxy, hydroxymethyl, alkoxymethyl or alkoxy and $R^y$ representing hydrogen or alkyl;

$R^a$ represents hydrogen or methyl;

$R^b$ represents hydrogen or methyl;

$R^4$ represents alkoxy;

n represents 0, 1, 2 or 3 and Z is a bond or n is 1 and Z is phenyl (the —P(O)(OH)$_2$ group being preferably in para position in this case);

and to the salts (in particular pharmaceutically acceptable salts) of such compounds.

iii) In particular, the invention relates to compounds of formula I that are also compounds of formula $I_{CE}$

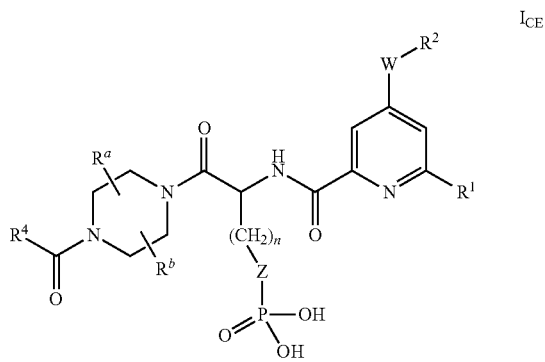

wherein
$R^1$ represents phenyl optionally substituted once by halogen, methyl, methoxy, trifluoromethyl and trifluoromethoxy (and preferably optionally substituted once by halogen, methyl or trifluoromethyl);
W represents a bond, and $R^2$ represents alkyl or a cycloalkyl group of 3 to 7 carbon atoms (preferably of 3 to 6 and more preferably of 3 to 5 carbon atoms) which may be substituted once by hydroxymethyl or alkoxymethyl (preferably methoxymethyl or ethoxymethyl and more preferably methoxymethyl), or $R^2$ represents a phenyl group optionally substituted once by alkoxy, or also $R^2$ represents an unsubstituted monocyclic heteroaryl group; or
W represents —O— and $R^2$ represents alkyl, hydroxyalkyl or alkoxyalkyl (and in particular alkyl or alkoxyalkyl); or
W represents —$NR^3$—, $R^2$ represents alkyl, carboxyalkyl, hydroxyalkyl, alkoxyalkyl, heterocyclyl, phenyl or phenylalkyl, or an unsubstituted cycloalkyl group of 3 to 7 carbon atoms (preferably of 3 to 6 and more preferably of 3 to 5 carbon atoms), and $R^3$ represents hydrogen or alkyl (and notably hydrogen or methyl); or
W represents —$NR^3$— and $R^2$ and $R^3$ form, together with the nitrogen that carries them, a heterocyclic ring of 4 to 7 (and especially 5 to 6) members wherein the members needed to complete said heterocyclic ring are each independently selected from —$CH_2$—, —$CHR^x$— and —$NR^y$—, it being understood however that said heterocyclic ring does not contain more than one member selected from the group consisting of —$CHR^x$— and —$NR^y$—, $R^x$ representing hydroxy, hydroxymethyl or alkoxy and $R^y$ representing alkyl (especially methyl);
$R^a$ represents hydrogen or methyl;
$R^b$ represents hydrogen;
$R^4$ represents alkoxy;
n represents 0, 1, 2 or 3 and Z is a bond or n is 1 and Z is phenyl (the —$PO(OH)_2$ group being preferably in para position in this case);
and to salts (in particular pharmaceutically acceptable salts) of compounds of formula $I_{CE}$.

iv) According to one preferred embodiment of this invention, the compounds of formula I as defined in embodiment i), ii) or iii) above or their salts (among which the pharmaceutically acceptable salts will be preferred) will be such that $R^4$ represents $(C_2-C_4)$alkoxy, especially linear $(C_2-C_4)$alkoxy and in particular n-butoxy.

v) According to a preferred variant of embodiment iv), the compounds of formula I (among which the pharmaceutically acceptable salts will be preferred) will be such that $R^4$ represents ethoxy.

vi) According to another preferred variant of embodiment iv), the compounds of formula I as defined in embodiment iv) above (among which the pharmaceutically acceptable salts will be preferred) will be such that $R^4$ represents n-butoxy.

vii) According to one particular embodiment of this invention, the compounds of formula I as defined in one of embodiments i) to vi) above or their salts (among which the pharmaceutically acceptable salts will be preferred) will be such that n represents 0.

viii) According to another particular embodiment of this invention, the compounds of formula I as defined in one of embodiments i) to vi) above or their salts (among which the pharmaceutically acceptable salts will be preferred) will be such that n represents 1.

ix) According to yet another particular embodiment of this invention, the compounds of formula I as defined in one of embodiments i) to vi) above or their salts (among which the pharmaceutically acceptable salts will be preferred) will be such that n represents 2.

x) According to yet a further particular embodiment of this invention, the compounds of formula I as defined in one of embodiments i) to vi) above or their salts (among which the pharmaceutically acceptable salts will be preferred) will be such that n represents 3.

xi) According to one main embodiment of this invention, the compounds of formula I as defined in one of embodiments i) to x) above (and notably as defined in embodiment viii) above) or their salts (among which the pharmaceutically acceptable salts will be preferred) will be such that Z is a bond.

xii) According to one sub-embodiment of this invention, the compounds of formula I as defined in embodiment xi) above or their salts (among which the pharmaceutically acceptable salts will be preferred) will be such that they have the stereochemistry drawn below

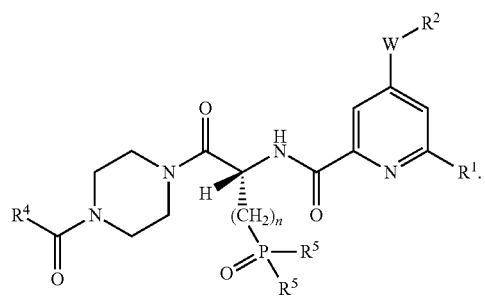

xiii) According to another sub-embodiment of this invention, the compounds of formula I as defined in embodiment xi) above or their salts (among which the pharmaceutically acceptable salts will be preferred) will be such that they have the stereochemistry drawn below

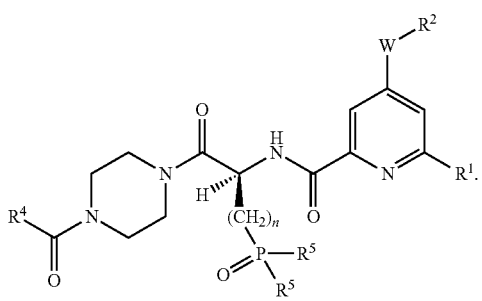

xiv) According to another main embodiment of this invention, the compounds of formula I as defined in one of embodiments i) to vi) and viii) above or their salts (among which the pharmaceutically acceptable salts will be preferred) will be such that Z is phenyl, and preferably such said compounds of formula I or their salts have the stereochemistry drawn below

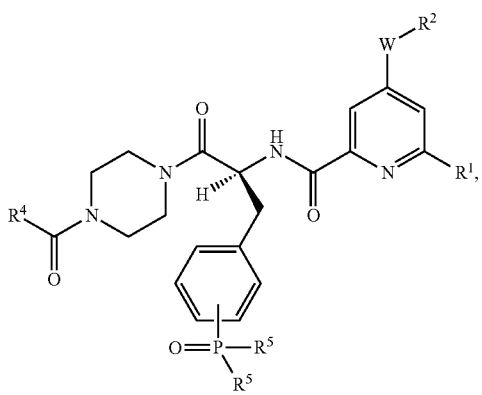

said compounds of formula I corresponding preferably to the formula below

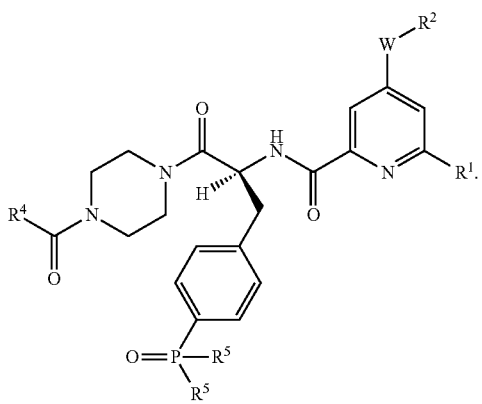

xv) Preferably, the compounds of formula I as defined in one of embodiments i) to xiv) above or their salts (among which the pharmaceutically acceptable salts will be preferred) will be such that $R^1$ represents phenyl optionally substituted once by halogen, methyl, methoxy, trifluoromethyl or trifluoromethoxy (notably phenyl optionally substituted once by halogen, methyl or trifluoromethyl and especially phenyl optionally substituted once by fluorine, methyl or trifluoromethyl).

xvi) Also preferably, the compounds of formula I as defined in one of embodiments i) to xv) above or their salts (among which the pharmaceutically acceptable salts will be preferred) will be such that $R^a$ represents hydrogen or methyl and $R^b$ represents hydrogen, and in particular such that each of $R^a$ and $R^b$ represents hydrogen.

xvii) According to one variant of this invention, the compounds of formula I as defined in one of embodiments i) to xvi) above or their salts (among which the pharmaceutically acceptable salts will be preferred) will be such that W represents a bond.

xviii) Preferably, the compounds of formula I as defined in embodiment xvii) above or their salts (among which the pharmaceutically acceptable salts will be preferred) will be such that $R^2$ represents cycloalkyl (especially cyclopropyl optionally substituted once by hydroxymethyl or alkoxymethyl), a phenyl group optionally substituted once by alkoxy, or also an unsubstituted monocyclic heteroaryl group (especially thiophen-3-yl).

xix) More preferably, the compounds of formula I as defined in embodiment xviii) above or their salts (among which the pharmaceutically acceptable salts will be preferred) will be such that $R^2$ represents a phenyl group optionally substituted once by alkoxy (especially 4-methoxy-phenyl), or also an unsubstituted monocyclic heteroaryl group (especially thiophen-3-yl).

xx) According to another variant of this invention, the compounds of formula I as defined in one of embodiments i) to xvi) above or their salts (among which the pharmaceutically acceptable salts will be preferred) will be such that W represents —O—.

xxi) Preferably, the compounds of formula I as defined in embodiment xx) above or their salts (among which the pharmaceutically acceptable salts will be preferred) will be such that $R^2$ represents alkyl (e.g. methyl) or alkoxyalkyl (e.g. 2-methoxy-ethyl).

xxii) According to a further variant of this invention, the compounds of formula I as defined in one of embodiments i) to xvi) above or their salts (among which the pharmaceutically acceptable salts will be preferred) will be such that W represents —$NR^3$—, $R^2$ represents alkyl, carboxyalkyl, hydroxyalkyl, alkoxyalkyl, heterocyclyl, cycloalkyl, aryl or aralkyl and $R^3$ represents hydrogen or alkyl, or such that W represents —$NR^3$— and $R^2$ and $R^3$ form, together with the nitrogen that carries them, a heterocyclic ring of 4 to 7 members wherein the members needed to complete said heterocyclic ring are each independently selected from —$CH_2$—, —$CHR^x$—, —O—, —S—, —CO— and —$NR^y$—, it being understood however that said heterocyclic ring does not contain more than one member selected from the group consisting of —$CHR^x$—, —O—, —S—, —CO— and —$NR^y$—, $R^x$ representing hydroxy, hydroxymethyl, alkoxymethyl or alkoxy and $R^y$ representing hydrogen or alkyl.

xxiii) According to one subvariant of said further variant, the compounds of formula I as defined in embodiment xxii) above or their salts (among which the pharmaceutically acceptable salts will be preferred) will be such that W represents —$NR^3$—, $R^2$ represents alkyl, carboxyalkyl, hydroxyalkyl, alkoxyalkyl, heterocyclyl, cycloalkyl, aryl or aralkyl and $R^3$ represents hydrogen or alkyl (notably hydrogen or methyl).

xxiv) Preferably, the compounds of formula I as defined in embodiment xxiii) above or their salts (among which the pharmaceutically acceptable salts will be preferred) will be such that $R^2$ represents alkyl, hydroxyalkyl, alkoxyalkyl, heterocyclyl, cycloalkyl, aryl or aralkyl and $R^3$ represents hydrogen or alkyl (notably hydrogen or methyl).

xxv) More preferably, the compounds of formula I as defined in embodiment xxiii) above or their salts (among which the pharmaceutically acceptable salts will be preferred) will be such that $R^2$ represents alkyl, hydroxyalkyl, alkoxyalkyl or heterocyclyl and $R^3$ represents hydrogen or methyl (and notably hydrogen).

xxvi) According to another subvariant of said further variant, the compounds of formula I as defined in embodiment xxii) above or their salts (among which the pharmaceutically acceptable salts will be preferred) will be such that W represents —$NR^3$— and $R^2$ and $R^3$ form, together with the nitrogen that carries them, a heterocyclic ring of 4 to 7 members wherein the members needed to complete said heterocyclic ring are each independently selected from —$CH_2$—, —$CHR^x$—, —O—, —S—, —CO— and —$NR^y$—, it being understood however that said heterocyclic ring does not contain more than one member selected from the group consisting of —$CHR^x$—, —O—, —S—, —CO— and —$NR^y$—, $R^x$ representing hydroxy, hydroxymethyl, alkoxymethyl or alkoxy and $R^y$ representing hydrogen or alkyl (notably hydrogen or methyl).

xxvii) Preferably, the compounds of formula I as defined in embodiment xxvi) above or their salts (among which the pharmaceutically acceptable salts will be preferred) will be such that $R^2$ and $R^3$ form, together with the nitrogen that carries them, a heterocyclic ring of 4 to 7 members (and notably of 5 to 6 members) wherein the members needed to complete said heterocyclic ring are each independently selected from —$CH_2$—, —$CHR^x$—, —O— and —$NR^y$—, it being understood however that said heterocyclic ring does not contain more than one member selected from the group consisting of —$CHR^x$—, —O— and —$NR^y$—, $R^x$ representing hydroxy, hydroxymethyl or alkoxy and $R^y$ representing alkyl (especially methyl).

xxviii) More preferably, the compounds of formula I as defined in embodiment xxvi) above or their salts (among which the pharmaceutically acceptable salts will be preferred) will be such that $R^2$ and $R^3$ form, together with the nitrogen that carries them, a heterocyclic ring of 5 to 6 members wherein the members needed to complete said heterocyclic ring are each independently selected from —$CH_2$—, —$CHR^x$—, —O— and —$NR^y$—, it being understood however that said heterocyclic ring does not contain more than one member selected from the group consisting of —$CHR^x$—, —O— and $NR^y$—, $R^x$ representing hydroxy, hydroxymethyl or methoxy and $R^y$ representing methyl (in particular such that $R^2$ and $R^3$ form, together with the nitrogen that carries them, pyrrolidin-1-yl, morpholin-4-yl, 4-methyl-piperazin-1-yl, 3-methoxy-pyrrolidin-1-yl, 3-hydroxy-pyrrolidin-1-yl or 2-hydroxymethyl-piperidin-1-yl and notably such that $R^2$ and $R^3$ form, together with the nitrogen that carries them, 4-methyl-piperazin-1-yl, 3-methoxy-pyrrolidin-1-yl or 2-hydroxymethyl-piperidin-1-yl).

xxix) According to another variant of this invention, the compounds of formula I as defined in one of embodiments i), ii), iv) to xvi) or xx) above or their salts (among which the pharmaceutically acceptable salts will be preferred) will be such that W represents —O— and $R^2$ represents heterocyclyl (notably tetrahydrofuran-3-yl).

xxx) According to a preferred variant of this invention, the compounds of formula I as defined in one of embodiments i) to xxix) above or their salts (among which the pharmaceutically acceptable salts will be preferred) will be such that $R^5$ represents hydroxy.

xxxi) According to another variant of this invention, the compounds of formula I as defined in one of embodiments i) or iv) to xxix) above or their salts (among which the pharmaceutically acceptable salts will be preferred) will be such that $R^5$ represents $R^6$—$OCH_2O$— or $R^7$-alkyl-NH—.

xxxii) According to a preferred variant of this invention, the compounds of formula I as defined in embodiment xxxi) above or their salts (among which the pharmaceutically acceptable salts will be preferred) will be such that $R^5$ represents $R^6$—$OCH_2O$—.

xxxiii) Preferably, the compounds of formula I as defined in one of embodiments xxxi) or xxxii) above or their salts (among which the pharmaceutically acceptable salts will be preferred) will be such that $R^6$ represents alkylcarbonyl or alkoxycarbonyl (and preferably methylcarbonyl or ethoxycarbonyl).

xxxiv) According to another preferred variant of this invention, the compounds of formula I as defined in embodiment xxxi) above or their salts (among which the pharmaceutically acceptable salts will be preferred) will be such that $R^5$ represents $R^7$-alkyl-NH— (and preferably 1-alkoxycarbonylethylamino).

xxxv) Preferably, the compounds of formula I as defined in one of embodiments xxxi) or xxxiv) above or their salts (among which the pharmaceutically acceptable salts will be preferred) will be such that $R^7$ represents ethoxycarbonyl.

xxxvi) According to another variant of this invention, the compounds of formula I as defined in embodiment i) above or their salts (among which the pharmaceutically acceptable salts will be preferred) will be such that $R^1$ represents phenyl which is unsubstituted (preferred) or monosubstituted with halogen, methyl, methoxy, trifluoromethyl or trifluoromethoxy;

W represents —$NR^3$— and $R^2$ and $R^3$ form, together with the nitrogen that carries them, a heterocyclic ring of 5 or 6 members (preferably 5 members) wherein the members needed to complete said heterocyclic ring are each independently selected from —$CH_2$—, —$CHR^x$— and —$NR^y$— (preferably —$CH_2$— and —$CHR^x$—), it being understood however that said heterocyclic ring does not contain more than one member selected from the group consisting of —$CHR^x$— and —$NR^y$—, $R^x$ representing alkoxy (preferably methoxy) and $R^y$ representing alkyl;

$R^a$ represents hydrogen;

$R^b$ represents hydrogen;

$R^4$ represents alkoxy;

$R^5$ represents $R^6$—$OCH_2O$— or $R^7$-alkyl-NH—;

$R^6$ represents alkylcarbonyl or alkoxycarbonyl;

$R^7$ represents alkoxycarbonyl; and n represents 1, 2 or 3 (preferably 1) and Z is a bond.

xxxvii) The following compounds of formula I as defined in embodiment i), ii) or iii) are particularly preferred:

4-((R)-2-{[4-((S)-3-methoxy-pyrrolidin-1-yl)-6-phenyl-pyridine-2-carbonyl]-amino}-4-phosphono-butyryl)-piperazine-1-carboxylic acid ethyl ester;

4-((R)-2-{[4-((S)-3-methoxy-pyrrolidin-1-yl)-6-phenyl-pyridine-2-carbonyl]-amino}-4-phosphono-butyryl)-piperazine-1-carboxylic acid butyl ester;

4-((R)-2-{[4-(4-methoxy-phenyl)-6-phenyl-pyridine-2-carbonyl]-amino}-3-phosphono-propionyl)-piperazine-1-carboxylic acid ethyl ester;

4-{(R)-2-[(6-phenyl-4-thiophen-3-yl-pyridine-2-carbonyl)-amino]-3-phosphono-propionyl}-piperazine-1-carboxylic acid ethyl ester;

4-{(R)-2-[(4,6-diphenyl-pyridine-2-carbonyl)-amino]-3-phosphono-propionyl}-piperazine-1-carboxylic acid ethyl ester;

4-{(R)-2-[(4-cyclopropyl-6-phenyl-pyridine-2-carbonyl)-amino]-3-phosphono-propionyl}-piperazine-1-carboxylic acid ethyl ester;

4-((R)-2-{[4-((R)-3-hydroxy-pyrrolidin-1-yl)-6-phenyl-pyridine-2-carbonyl]-amino}-3-phosphono-propionyl)-piperazine-1-carboxylic acid ethyl ester;

4-((R)-2-{[4-(2-methoxy-ethylamino)-6-phenyl-pyridine-2-carbonyl]-amino}-3-phosphono-propionyl)-piperazine-1-carboxylic acid ethyl ester;

4-((R)-2-{[4-(2-hydroxy-ethylamino)-6-phenyl-pyridine-2-carbonyl]-amino}-3-phosphono-propionyl)-piperazine-1-carboxylic acid ethyl ester;

4-[(R)-2-({4-[(2-methoxy-ethyl)-methyl-amino]-6-phenyl-pyridine-2-carbonyl}-amino)-3-phosphono-propionyl]-piperazine-1-carboxylic acid ethyl ester;

4-{(R)-2-[(4-benzylamino-6-phenyl-pyridine-2-carbonyl)-amino]-3-phosphono-propionyl}-piperazine-1-carboxylic acid ethyl ester;

4-(-2-{[4-((S)-3-methoxy-pyrrolidin-1-yl)-6-phenyl-pyridine-2-carbonyl]-amino}-2-phosphono-acetyl)-piperazine-1-carboxylic acid butyl ester;

4-((S)-2-{[4-((S)-3-methoxy-pyrrolidin-1-yl)-6-phenyl-pyridine-2-carbonyl]-amino}-5-phosphono-pentanoyl)-piperazine-1-carboxylic acid butyl ester;

4-((R)-2-{[4-((S)-3-methoxy-pyrrolidin-1-yl)-6-phenyl-pyridine-2-carbonyl]-amino}-5-phosphono-pentanoyl)-piperazine-1-carboxylic acid butyl ester;

4-((R)-2-{[6-(2-fluoro-phenyl)-4-phenyl-pyridine-2-carbonyl]-amino}-3-phosphono-propionyl)-piperazine-1-carboxylic acid butyl ester;

4-((R)-2-{[4-phenyl-6-(3-trifluoromethyl-phenyl)-pyridine-2-carbonyl]-amino}-3-phosphono-propionyl)-piperazine-1-carboxylic acid butyl ester;

4-((R)-2-{[6-(4-fluoro-phenyl)-4-phenyl-pyridine-2-carbonyl]-amino}-3-phosphono-propionyl)-piperazine-1-carboxylic acid butyl ester;

4-{(R)-2-[(4-phenyl-6-phenyl-pyridine-2-carbonyl)-amino]-3-phosphono-propionyl}-piperazine-1-carboxylic acid butyl ester;

4-((R)-2-{[4-((1S,2S)-2-methoxymethyl-cyclopropyl)-6-phenyl-pyridine-2-carbonyl]-amino}-3-phosphono-propionyl)-piperazine-1-carboxylic acid butyl ester;

4-((R)-2-{[4-((1S,2S)-2-hydroxymethyl-cyclopropyl)-6-phenyl-pyridine-2-carbonyl]-amino}-3-phosphono-propionyl)-piperazine-1-carboxylic acid butyl ester;

4-((R)-2-{[4-((S)-3-methoxy-pyrrolidin-1-yl)-6-phenyl-pyridine-2-carbonyl]-amino}-3-phosphono-propionyl)-piperazine-1-carboxylic acid ethyl ester;

4-((R)-2-{[4-((S)-3-methoxy-pyrrolidin-1-yl)-6-phenyl-pyridine-2-carbonyl]-amino}-3-phosphono-propionyl)-piperazine-1-carboxylic acid butyl ester;

4-((S)-2-{[4-((S)-3-methoxy-pyrrolidin-1-yl)-6-phenyl-pyridine-2-carbonyl]-amino}-3-phosphono-propionyl)-piperazine-1-carboxylic acid ethyl ester;

4-[(S)-2-{[4-((S)-3-methoxy-pyrrolidin-1-yl)-6-phenyl-pyridine-2-carbonyl]-amino}-3-(4-phosphono-phenyl)-propionyl]-piperazine-1-carboxylic acid ethyl ester;

4-{(R)-2-[(4-isopropyl-6-phenyl-pyridine-2-carbonyl)-amino]-3-phosphono-propionyl}-piperazine-1-carboxylic acid butyl ester;

4-{(R)-2-[(4-methoxy-6-phenyl-pyridine-2-carbonyl)-amino]-3-phosphono-propionyl}-piperazine-1-carboxylic acid butyl ester;

4-{(R)-2-[(6-phenyl-4-pyrrolidin-1-yl-pyridine-2-carbonyl)-amino]-3-phosphono-propionyl}-piperazine-1-carboxylic acid butyl ester;

4-((R)-2-{[4-(4-methyl-piperazin-1-yl)-6-phenyl-pyridine-2-carbonyl]-phosphonomethyl-amino}-acetyl)-piperazine-1-carboxylic acid butyl ester;

4-((R)-2-{[6-phenyl-(R)-4-(tetrahydro-furan-3-ylamino)-pyridine-2-carbonyl]-amino}-3-phosphono-propionyl)-piperazine-1-carboxylic acid butyl ester;

4-{(R)-2-[(2-hydroxymethyl-6'-phenyl-3,4,5,6-tetrahydro-2H-[1,4']bipyridinyl-2'-carbonyl)-amino]-3-phosphono-propionyl}-piperazine-1-carboxylic acid butyl ester;

4-{(R)-2-[(4-cyclopropylamino-6-phenyl-pyridine-2-carbonyl)-amino]-3-phosphono-propionyl}-piperazine-1-carboxylic acid butyl ester;

4-{(R)-2-[(6-phenyl-4-phenylamino-pyridine-2-carbonyl)-amino]-3-phosphono-propionyl}-piperazine-1-carboxylic acid butyl ester;

4-{(R)-2-[(6-phenyl-4-propylamino-pyridine-2-carbonyl)-amino]-3-phosphono-propionyl}-piperazine-1-carboxylic acid butyl ester;

4-((R)-2-{[4-(2-carboxy-ethylamino)-6-phenyl-pyridine-2-carbonyl]-amino}-3-phosphono-propionyl)-piperazine-1-carboxylic acid butyl ester;

4-((R)-2-{[4-(3-methoxy-pyrrolidin-1-yl)-6-phenyl-pyridine-2-carbonyl]-amino}-3-phosphono-propionyl)-3-methyl-piperazine-1-carboxylic acid ethyl ester (notably 4-((R)-2-{[4-((S)-3-methoxy-pyrrolidin-1-yl)-6-phenyl-pyridine-2-carbonyl]-amino}-3-phosphono-propionyl)-3-methyl-piperazine-1-carboxylic acid ethyl ester);

4-((R)-2-{[4-(2-methoxy-ethoxy)-6-phenyl-pyridine-2-carbonyl]-amino}-3-phosphono-propionyl)-piperazine-1-carboxylic acid butyl ester;

4-{(R)-2-[(4-methyl-6-phenyl-pyridine-2-carbonyl)-amino]-3-phosphono-propionyl}-piperazine-1-carboxylic acid butyl ester;

4-((S)-2-{[4-((S)-3-methoxy-pyrrolidin-1-yl)-6-phenyl-pyridine-2-carbonyl]-amino}-4-phosphono-butyryl)-piperazine-1-carboxylic acid butyl ester;

as well as the salts (in particular pharmaceutically acceptable salts) thereof.

xxxviii) Further preferred compounds of formula I as defined in embodiment i) are selected from the group consisting of:

4-((R)-3-(Bis-acetoxymethoxy-phosphoryl)-2-{[4-((S)-3-methoxy-pyrrolidin-1-yl)-6-phenyl-pyridine-2-carbonyl]-amino}-propionyl)-piperazine-1-carboxylic acid butyl ester;

4-((R)-3-(Bis-ethoxycarbonyloxymethoxy-phosphoryl)-2-{[4-((S)-3-methoxy-pyrrolidin-1-yl)-6-phenyl-pyridine-2-carbonyl]-amino}-propionyl)-piperazine-1-carboxylic acid butyl ester;

N,N'-Bis-((S)-1-ethoxycarbonylethyl)-2-{(R)-[4-((S)-3-methoxy-pyrrolidin-1-yl)-6-phenyl-pyridine-2-carbonyl]-amino}-3-oxo-3-(4-butoxy-carbonyl-piperazin-1-yl)-propyl-phosphonic acid diamide; and 4-[(R)-2-({6-Phenyl-4-[(tetrahydro-furan-3-yl)oxy]-pyridine-2-carbonyl}-amino)-3-phosphono-propionyl]-piperazine-1-carboxylic acid butyl ester;

as well as the salts (in particular pharmaceutically acceptable salts) thereof.

It is well understood that any stereogenic center of any compound listed in embodiment xxxvii) or xxxviii), which is not explicitly assigned, may be in absolute (R)- or (S)-configuration.

xxxix) A further object of the invention is the compounds of formula I (or of formula $I_P$ or $I_{CE}$), as defined in one of embodiments i) to xxxviii) above, or their pharmaceutically acceptable salts, as medicaments.

The compounds of formula I and their pharmaceutically acceptable salts can be used as medicaments, e.g. in the form of pharmaceutical compositions for enteral or parenteral administration.

xl) The invention thus also relates to pharmaceutical compositions containing at least one compound according to one of embodiments i) to xxxviii) above, or a pharmaceutically acceptable salt thereof, and a pharmaceutically acceptable carrier, diluent or excipient. In particular, the invention relates to pharmaceutical compositions containing at least one compound of formula I (or of formula $I_P$ or $I_{CE}$) and one or more pharmaceutically acceptable carriers, diluents or excipients.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

xli) The compounds according to formula I as defined in embodiments i) to xxxviii) above and the pharmaceutically acceptable salts thereof may be used for the preparation of a medicament, and are suitable:

for the treatment or prophylaxis of diseases including stable angina, unstable angina, myocardial infarction, embolism (including complications of atherosclerosis, notably embolic stroke), arterial thrombosis (including primary arterial thrombotic complications of atherosclerosis, notably thrombotic stroke), venous thrombosis (notably deep vein thrombosis), thrombosis secondary to vascular damage or to inflammation (including vasculitis, arteritis and glomerulonephritis), venoocclusive diseases, transient ischaemic attacks, peripheral vascular diseases, myocardial infarction with or without thrombolysis, myeloproliferative disease, thrombocythaemia, sickle cell disease, inflammatory bowel disease, thrombotic thrombocytopaenic purpura, haemolytic uraemic syndrome;

for preventing thrombotic complications of septicaemia, adult respiratory distress syndrome, anti-phospholipid syndrome, heparin-induced thrombocytopaenia and pre-eclampsia/eclampsia;

for preventing cardiovascular complications after certain surgery procedures (notably coronary revascularisation like angioplasty (PTCA), other vascular graft surgery, endarterectomy or stent placement) or after accidental trauma;

for preventing organ graft rejection.

xlii) In another embodiment, the compounds of formula I as defined in embodiments i) to xxxviii) above and the pharmaceutically acceptable salts thereof may be used for the preparation of a medicament, and are suitable for preventing complications in conditions in which vasospasms lead to vasoconstriction and thus tissue-ischemia or tissue-death (necrosis).

xliii) Therefore, a particular object of this invention is the use of a compound of formula I (or of formula $I_P$ or $I_{CE}$) as defined in one of embodiments i) to xxxviii) above, or of a pharmaceutically acceptable salt thereof, for the manufacture of a medicament for the uses listed in embodiments xli) and/or xlii) (and in particular in embodiment xli)) above, and for the manufacture of a medicament for the treatment of occlusive vascular disorders in general.

xliv) More generally, the invention relates to the use of a compound of formula I (or of formula $I_P$ or $I_{CE}$) as defined in one of embodiments i) to xxxviii) above, or of a pharmaceutically acceptable salt thereof, for the manufacture of a medicament for the treatment and/or prevention of occlusive vascular disorders as well as to the use of a compound of formula I (or of formula $I_P$ or $I_{CE}$) for the manufacture of a medicament for the treatment and/or prevention of peripheral vascular, of visceral-, hepatic- and renal-vascular, of cardiovascular and of cerebrovascular diseases or conditions associated with platelet aggregation, including thrombosis in humans and other mammals.

xlv) Among the above-mentioned uses of compounds of formula I (or of formula $I_P$ or $I_{CE}$) or of pharmaceutically acceptable salts thereof for the manufacture of medicaments according to embodiment xliii) above, the uses for manufacturing medicaments for the treatment or prophylaxis of myocardial infarction, arterial thrombosis (notably thrombotic stroke), transient ischaemic attacks, peripheral vascular disease and stable and unstable angina will be preferred.

xlvi) The invention further relates to the use of a compound of formula I (or of formula $I_P$ or $I_{CE}$) according to one of embodiments i) to xxxviii) above, or of a pharmaceutically acceptable salt thereof, for the preservation of blood products in vitro (e.g. the preservation of platelet concentrates), or for the prevention of occlusion in extra-corporeal blood or blood product treatment machines (such as renal dialysis machines or plasmapheresis machines).

xlvii) The invention also relates to methods of treatment for the disorders mentioned in embodiments xli) and/or xlii) (and in particular in embodiment xli)) above, said methods comprising the administration to a patient in need thereof of an effective amount of a compound of formula I (or of formula $I_P$ or $I_{CE}$) according to one of embodiments i) to xxxviii), or of a pharmaceutically acceptable salt of such a compound.

Any reference to a compound of formula I, $I_P$ or $I_{CE}$ in this text is to be understood as referring also to the salts (and especially the pharmaceutically acceptable salts) of such compounds, as appropriate and expedient. The preferences indicated for the compounds of formula I of course apply mutatis mutandis to the compounds of formula $I_P$ or $I_{CE}$, as well as to the salts and pharmaceutically acceptable salts of the compounds of formula I, of formula $I_P$ or of formula $I_{CE}$. The same applies to these compounds as medicaments, to pharmaceutical compositions containing these compounds as active principles, to the uses of these compounds for the manufacture of a medicament for the treatment of the diseases according to this invention or to the compounds for the treatment of the diseases according to this invention.

According to the invention, the compounds of formula I (or of formula $I_P$ or $I_{CE}$) can be prepared by the process described below.

Preparation of the Compounds of Formula I

Abbreviations:

The following abbreviations are used throughout the specification and the examples:

abs. absolute
Ac acetyl
ADP adenosine diphosphate
anh. anhydrous
aq. aqueous
Boc tert-butoxycarbonyl
BSA bovine serum albumin
Cbz benzyloxycarbonyl
CC column chromatography
conc. concentrated
DCM dichloromethane
DIPEA diisopropylethylamine
DME 1,2-dimethoxyethane
DMF N,N-dimethylformamide DMPU N,N'-dimethylpropylene urea
dpm decays per minute
EA ethyl acetate
EDCI N-(3-dimethylaminopropyl)-N'-ethylcarbodiimide
EDTA ethylenediaminetetraacetic acid
Et ethyl
eq. equivalent(s)
HATU 2-(7-aza-1H-benzotriazole-1-yl)-1,1,3,3-tetramethyluronium hexafluorophosphate
Hept heptane
HOBT 1-hydroxybenzotriazole
HPLC High-performance liquid chromatography
Hse L-homoserine
HV high vacuum
LC-MS Liquid Chromatography-Mass Spectrometry
MCPBA meta-chloroperbenzoic acid
Me methyl
NMP N-methylpyrrolidone
org. organic
Pd/C palladium on carbon
Ph phenyl
PyBOP benzotriazole-1-yl-oxy-tris-pyrrolidino-phosphonium hexafluorophosphate
Rf retention factor
RT room temperature
sat. saturated
SDS sodium dodecyl sulfate
tBu tert-butyl
TBME tert-butylmethylether
TFA trifluoroacetic acid
THF tetrahydrofuran
TLC thin layer chromatography
$t_R$ retention time
Tris tris(hydroxymethyl)aminomethane General Preparation Route:

The various compounds of formula I can be prepared using the general routes summarized in Scheme 1 and Scheme 1a hereafter.

Scheme 1

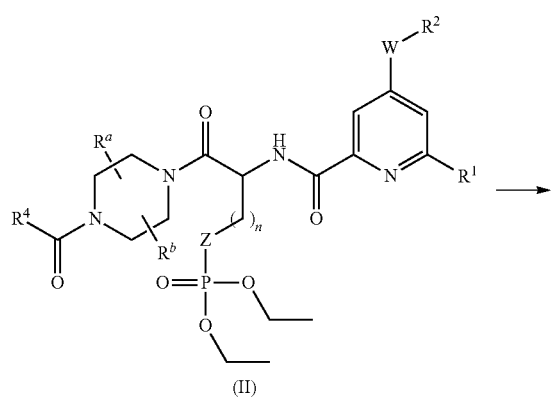

(II)

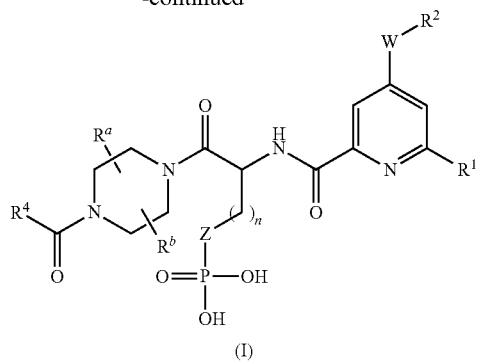

(I)

The compounds of formula I, wherein $R^5$ represents hydroxy, can be prepared by treating the compounds of formula II with HCl optionally in the presence of water, in a suitable organic solvent such as THF, EA, dioxane or $Et_2O$ and preferably at a temperature around RT, or with trimethylsilyl bromide or trimethylsilyl iodide in a suitable solvent such as DCM or MeCN and preferably at a temperature around RT (scheme 1).

Scheme 1a

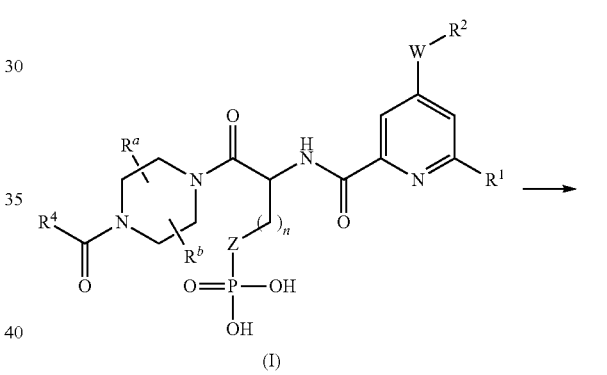

(I)

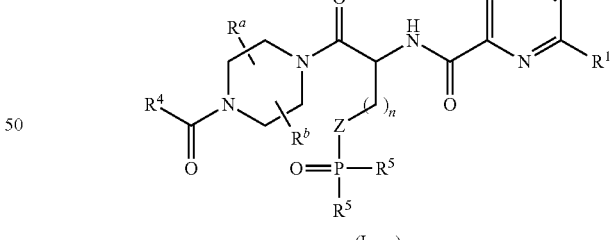

$(I_{PDG})$

The compounds of formula $I_{PDG}$, wherein $R^5$ represents $R^6$—$OCH_2O$—, can be prepared by the reaction between a phosphonic acid of formula I, wherein $R^5$ represents hydroxy, and an appropriate halide derivative of formula $R^6$—$OCH_2$—X, X being chloride, bromide or iodide, in the presence of a suitable base (e.g. $NEt_3$, DIPEA) in a suitable solvent such as DMF, NMP or DMPU, optionally in the presence of NaI and preferably at a temperature between 45 and 90° C. (scheme 1a).

The compounds of formula $I_{PDG}$, wherein $R^5$ represents $R^7$-alkyl-NH—, can be prepared by the reaction between a phosphonic acid of formula I, wherein $R^5$ represents hydroxy, and an appropriate amino acid alkyl ester (preferably an α-amino acid alkyl ester) of formula $R^7$-alkyl-$NH_2$ in the presence of a suitable base (e.g. $NEt_3$) and an activating mixture of reagents such as a combination of 2,2'-dipyridyl disulfide and $PPh_3$ in a suitable solvent such as anhydrous pyridine and preferably at a temperature of about 60° C. (scheme 1a).

Preparation of the Various Synthesis Intermediates:
Preparation of the Compounds of Formula II The compounds of formula II can be prepared using the routes summarized in Schemes 2, 2a and 2b hereafter.

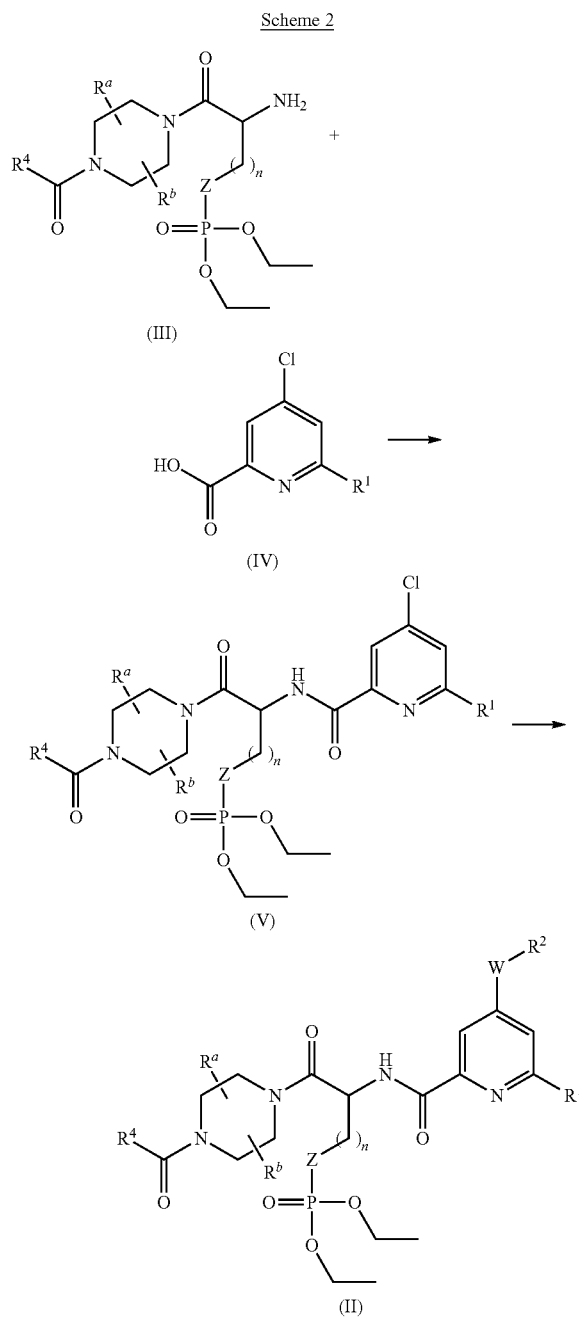

The compounds of formula V can be obtained (Scheme 2) by coupling a compound of formula III with a compound of formula IV using standard peptide coupling methods such as PyBOP, in the presence of a suitable base such as $NEt_3$, DIPEA or N-methylmorpholine and in a suitable solvent such as DCM, THF or DMF, preferably at a temperature around RT.

The resulting intermediates of formula V can then be converted into compounds of formula II wherein W is —$NR^3$— by aromatic substitution reaction with an amine of formula $HNR^2R^3$ optionally in the presence of a suitable base such as $NEt_3$, DIPEA or N-methylmorpholine, the reaction being carried out in a suitable solvent such as THF, MeCN, DMF or NMP and preferably between 80° C. and 160° C. in a microwave oven. Alternatively, the compounds of formula II wherein W is —$NR^3$— can be obtained by a Buchwald-Hartwig type of reaction, using an amine of formula $HNR^2R^3$, in the presence of a suitable palladium catalyst such as acetato(2'-di-tert-butylphosphino-1,1'-biphenyl-2-yl)palladium, in the presence of a suitable base such as sodium tert-butoxide and heating in toluene at about 90° C.

The intermediates of formula V can furthermore be converted into compounds of formula II wherein W is a bond, using reagents of formula $R^2$—$B(OR)_2$ wherein R is hydrogen or alkyl with standard conditions for a Suzuki reaction, and preferably boronic acid or ester derivatives in the presence of a suitable base such as $K_3PO_4$, $Na_2CO_3$ or $K_2CO_3$, in the presence of a suitable palladium catalyst such as tetrakis(triphenylphosphine) palladium in a suitable solvent such as DME/water or dioxane, and preferably heating between 80° C. and 110° C. Alternatively, the intermediates of formula V can also be converted into compounds of formula II wherein W is a bond, using magnesium derivatives of formula $R^2$—MgBr, in the presence of a suitable iron catalyst such as iron(III)acetylacetonate, in a suitable solvent such as THF and at a temperature preferably around RT (see A. Fürstner et al. in J. Am. Chem. Soc. (2002), 13856-13863). Besides, the intermediates of formula V can also be converted into compounds of formula II wherein W is a bond, using reagents of formula $R^2$—$SnBu_3$ with standard conditions for a Stille reaction, and preferably a tributylstannane derivative in a suitable solvent such as toluene, and preferably heating at about 130° C.

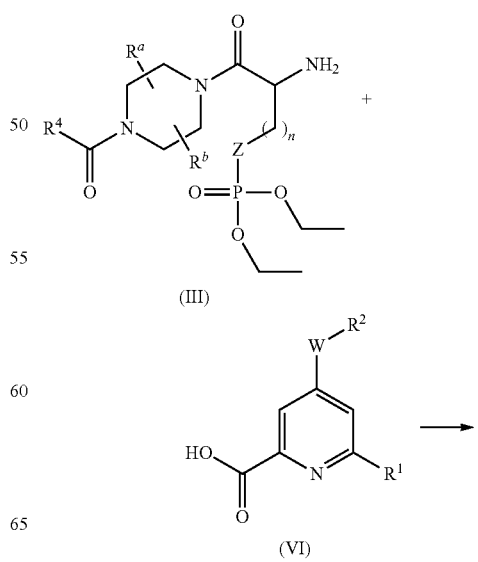

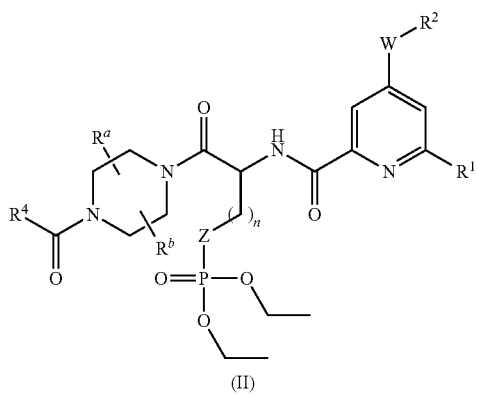

(II)

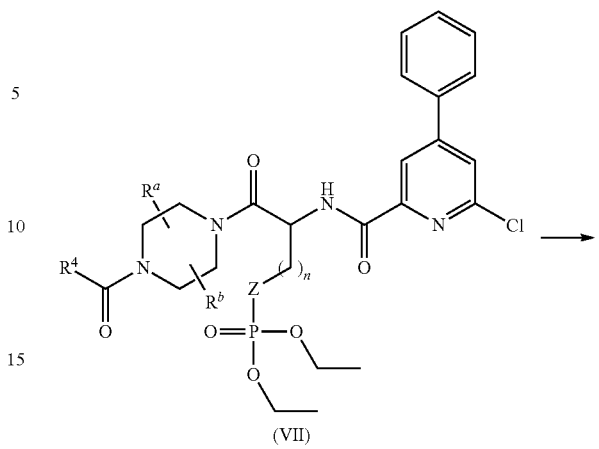

(VII)

Alternatively, the compounds of formula II can be prepared as described in Scheme 2a by coupling compounds of formula III with compounds of formula VI using standard peptide coupling methods such as PyBOP, HOBT, EDCI hydrochloride, 1,3-dicyclohexylcarbodiimide, HATU, optionally in the presence of a suitable base such as $NEt_3$, DIPEA or N-methylmorpholine and in a suitable solvent such as DCM, THF or DMF, preferably at a temperature around RT.

Besides, the compounds of formula II wherein W is a bond and $R^2$ is phenyl can be prepared as described in Scheme 2b hereafter.

Scheme 2b

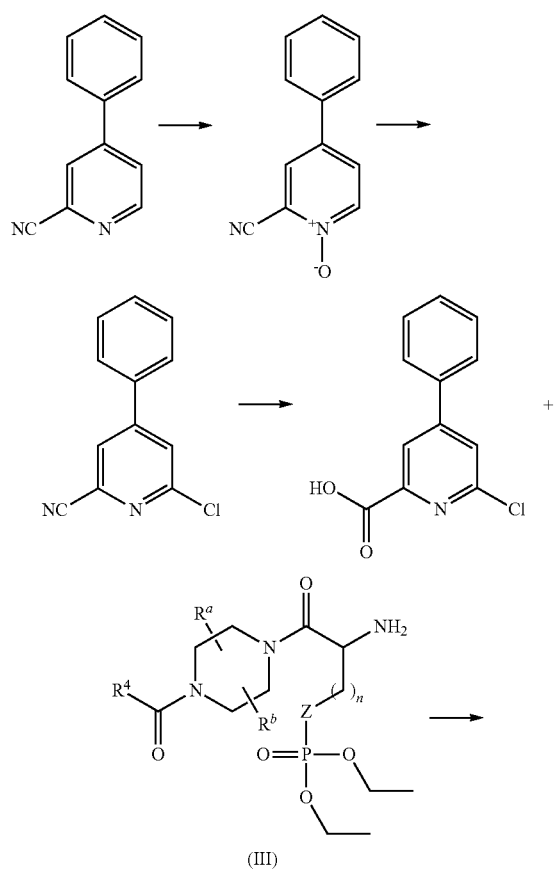

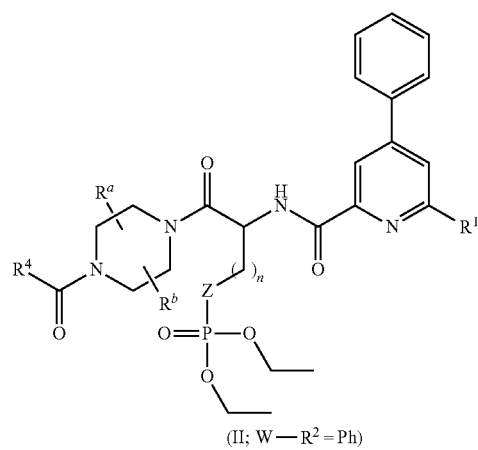

(II; W—$R^2$=Ph)

4-phenyl-pyridine-2-carbonitrile is easily accessible using a literature procedure (*J. Org. Chem.* (1992), 57, 6020-6025). It can be oxidized using standard conditions for the oxidation of a pyridine, using standard oxidizing agents such as MCPBA, in a suitable solvent such as DCM, and at a temperature between room temperature and 40° C. The pyridine oxide derivative thus obtained can be chlorinated using standard conditions (e.g. phosphoryl chloride at reflux). The cyano group can be further hydrolyzed using standard conditions (e.g. conc. hydrochloric acid at reflux). The chloropyridine derivative can be coupled to compounds of formula III by preparing the acid chloride using standard reagents such as thionyl chloride or oxalyl chloride, or as defined earlier, using the same standard coupling methods as those described above for the coupling reaction involving compounds of formulae III and VI (Scheme 2a). The intermediates of formula VII can finally be converted into compounds of formula II using reagents of formula $R^1$—$B(OR)_2$ wherein R is hydrogen or alkyl, using the same standard conditions for a Suzuki reaction as those described with the intermediates of formula V (see Scheme 2).

Similar procedures can be used to obtain compounds of formula II wherein W is a bond and $R^2$ is a substituted phenyl group.

Preparation of the Compounds of Formula III

The compounds of formula III wherein Z is a bond and n is 1 (hereafter "the compounds of formula $III_{B1}$") can be prepared using the route shown in Scheme 3 hereafter.

Scheme 3

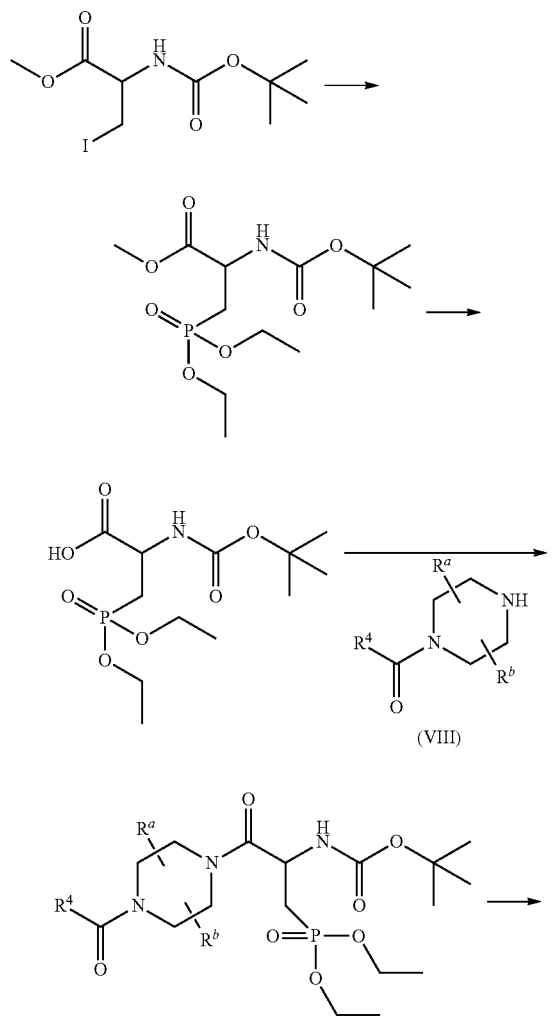

(VIII)

(IX)

(III$_{B1}$)

The compounds of formula IX can be obtained in three steps starting from Boc-3-iodo-L-Ala-OMe or Boc-3-iodo-D-Ala-OMe: an Arbuzov reaction is performed (e.g. using P(OEt)$_3$ at reflux) followed by a saponification reaction using standard conditions such as NaOH or LiOH in a mixture of water and a suitable organic solvent such as THF, MeOH or EtOH; finally the resulting acid intermediate is coupled with a compound of formula VIII using standard peptide coupling methods such as those described for the synthesis of compounds of formula II (see Scheme 2a). The compounds of formula III$_{B1}$ can then be obtained from the compounds of formula IX by standard acidic conditions for the removal of a Boc group that are well known to one skilled in the art, e.g. HCl or TFA.

The compounds of formula III wherein Z is a bond and n is 2 (hereafter "the compounds of formula III$_{B2}$") can be prepared using the routes summarized in Schemes 3a and 3b hereafter.

The compounds of formula III$_{B2}$ wherein the carbon bearing the amino group has the "R" configuration (hereafter "the compounds of formula III$_{B2R}$") can thus be prepared as shown in Scheme 3a hereafter.

Scheme 3a

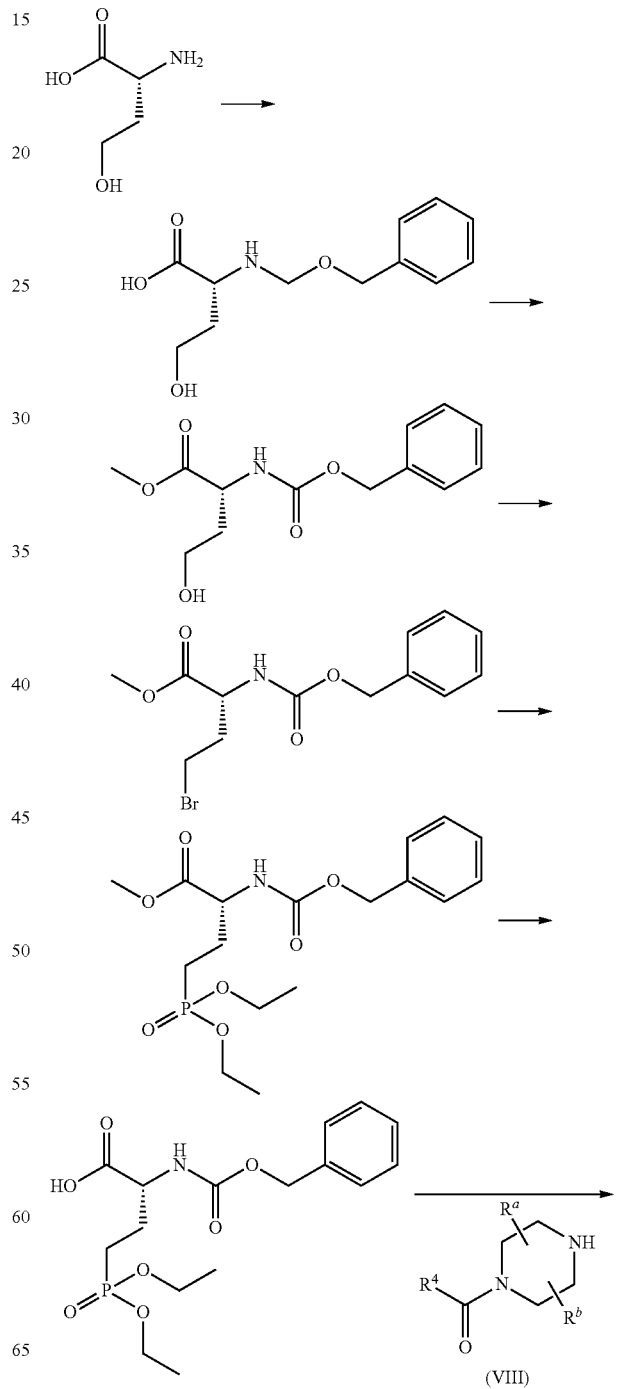

(VIII)

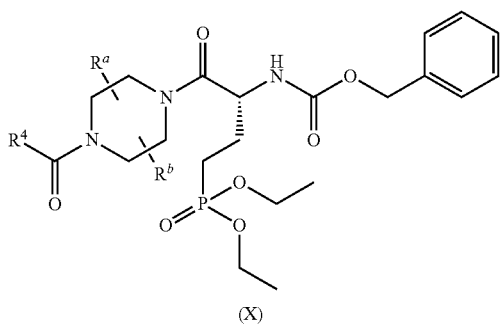

(X)

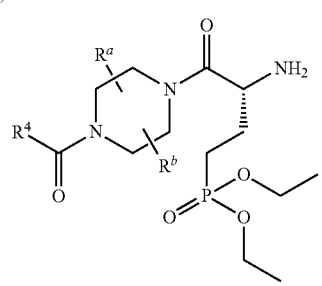

(III$_{B2R}$)

D-Homoserine can first be protected on the nitrogen with a Cbz group using standard conditions known to one skilled in the art. The corresponding dicyclohexylamine salt of the resulting intermediate can be prepared and the methyl ester can be formed using MeI in DMF at a temperature around RT. The hydroxy function can then be substituted by a bromide using standard conditions such as PPh$_3$ and CBr$_4$, in a suitable solvent such as DCM, preferably between 0° C. and RT. The next three steps leading to the compounds of formula X can be performed using conditions such as those already described for the synthesis of the compounds of formula IX (see Scheme 3). The compounds of formula III$_{B2R}$ can then be obtained by cleaving the Cbz protecting group using standard conditions known to one skilled in the art.

The compounds of formula III$_{B2}$ wherein the carbon bearing the amino group has the "S" configuration (hereafter "the compounds of formula III$_{B2S}$") can thus be prepared as shown in Scheme 3b hereafter.

Scheme 3b

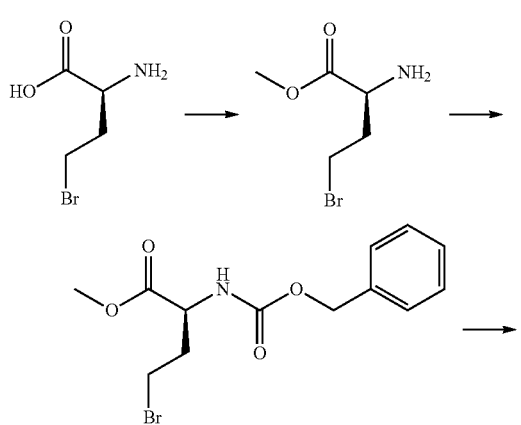

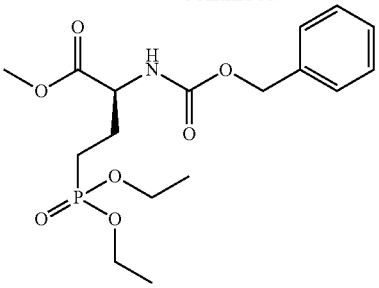

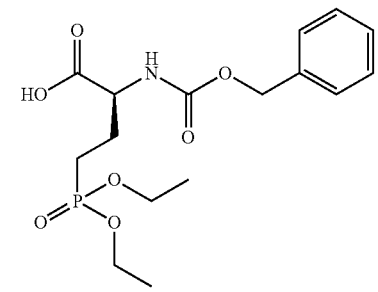

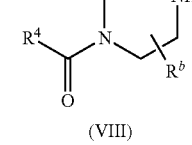

(VIII)

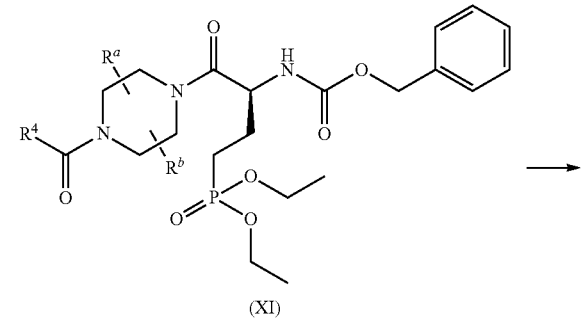

(XI)

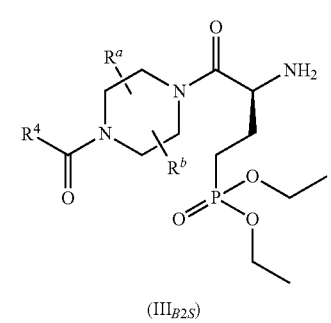

(III$_{B2S}$)

To obtain the compounds of formula III$_{B2S}$, one can start the synthesis with (S)-(+)-2-amino-4-bromobutyric acid hydrobromide salt, which is first protected on the acid by forming a methyl ester using standard conditions known to one skilled in the art (e.g. HCl in MeOH). A Cbz group can then be introduced on the nitrogen using standard conditions known to one skilled in the art. The next three steps leading to the compounds of formula XI can be performed using conditions such as those already described for the synthesis of the compounds of formula IX (see Scheme 3). The Cbz cleavage can be performed using standard conditions known to one skilled in the art (e.g. Pd/C in MeOH).

The compounds of formula III wherein Z is a bond and n is 0 (hereafter "the compounds of formula III$_{B0}$") can be prepared using the route summarized in Scheme 3c hereafter.

Scheme 3c

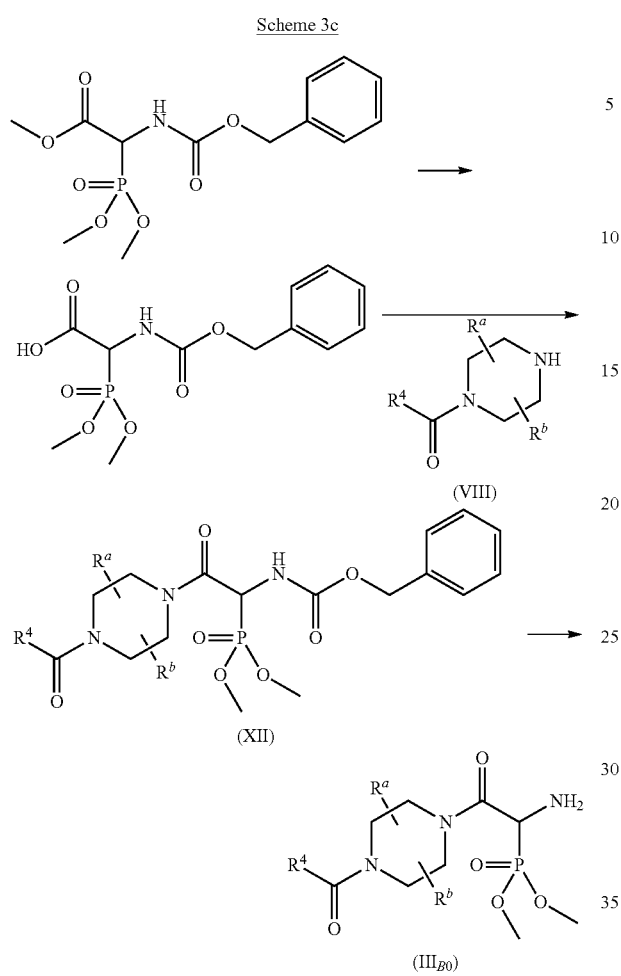

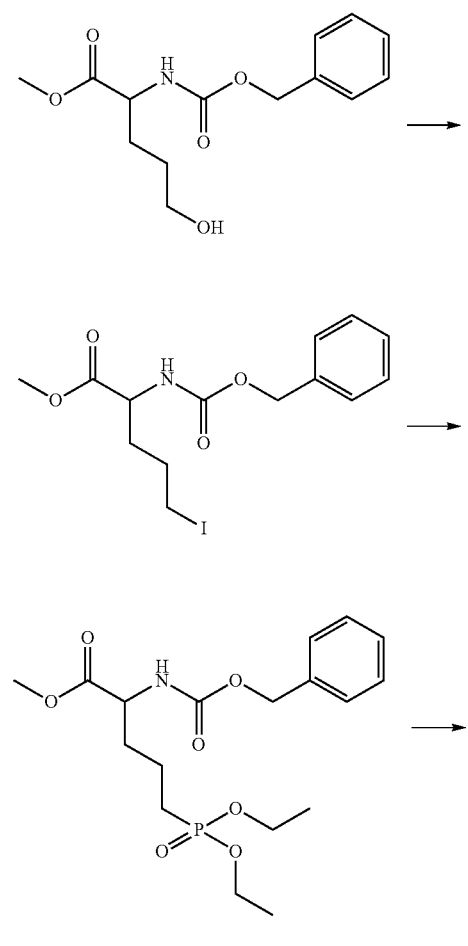

The compounds of formula XII can be obtained in two steps starting from Cbz-α-phosphinoglycine trimethyl ester: a saponification reaction is performed using standard conditions such as NaOH or LiOH in a mixture of water and a suitable organic solvent such as THF, MeOH or EtOH; the obtained acid intermediate is coupled with a compound of formula VIII using standard peptide coupling methods such as those described for the synthesis of compounds of formula II (see Scheme 2a). The compounds of formula III$_{B0}$ can then be obtained by standard conditions for the removal of a Cbz group that are well known to one skilled in the art (e.g. Pd/C in EtOH).

The compounds of formula III wherein Z is a bond and n is 3 (hereafter "the compounds of formula III$_{B3}$") can be prepared using the route summarized in Scheme 3d hereafter.

Scheme 3d

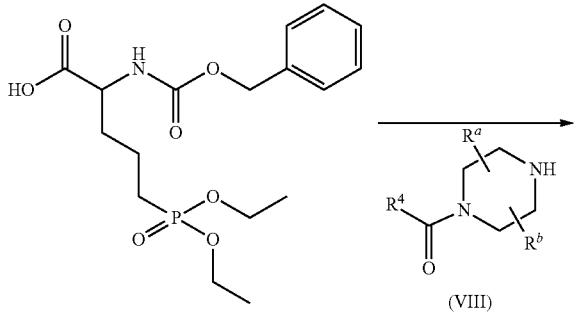

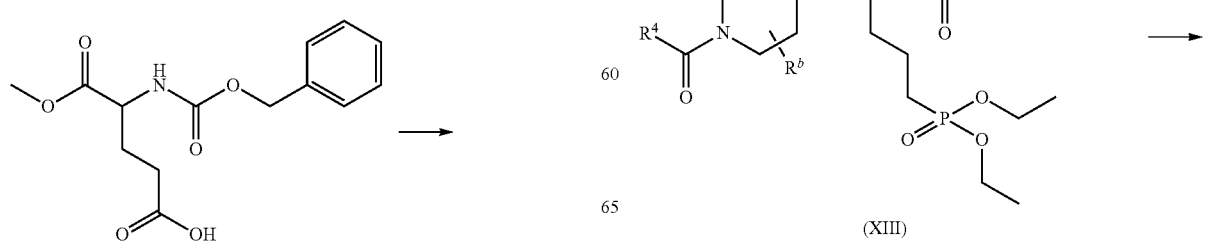

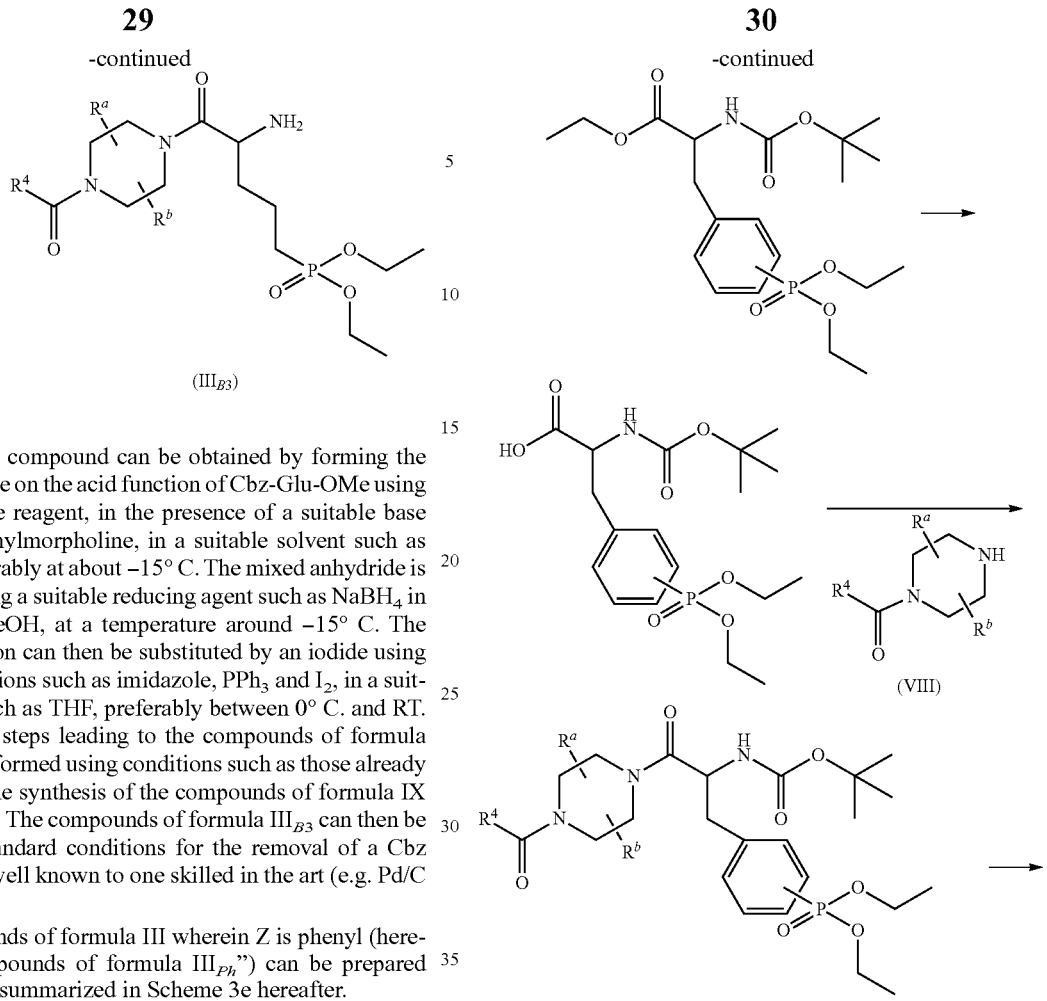

(III$_{B3}$)

The hydroxy compound can be obtained by forming the mixed anhydride on the acid function of Cbz-Glu-OMe using a chloroformate reagent, in the presence of a suitable base such as N-methylmorpholine, in a suitable solvent such as THF, and preferably at about −15° C. The mixed anhydride is reduced by using a suitable reducing agent such as NaBH$_4$ in presence of MeOH, at a temperature around −15° C. The hydroxy function can then be substituted by an iodide using standard conditions such as imidazole, PPh$_3$ and I$_2$, in a suitable solvent such as THF, preferably between 0° C. and RT. The next three steps leading to the compounds of formula XIII can be performed using conditions such as those already described for the synthesis of the compounds of formula IX (see Scheme 3). The compounds of formula III$_{B3}$ can then be obtained by standard conditions for the removal of a Cbz group that are well known to one skilled in the art (e.g. Pd/C in MeOH).

The compounds of formula III wherein Z is phenyl (hereafter "the compounds of formula III$_{Ph}$") can be prepared using the route summarized in Scheme 3e hereafter.

Scheme 3e

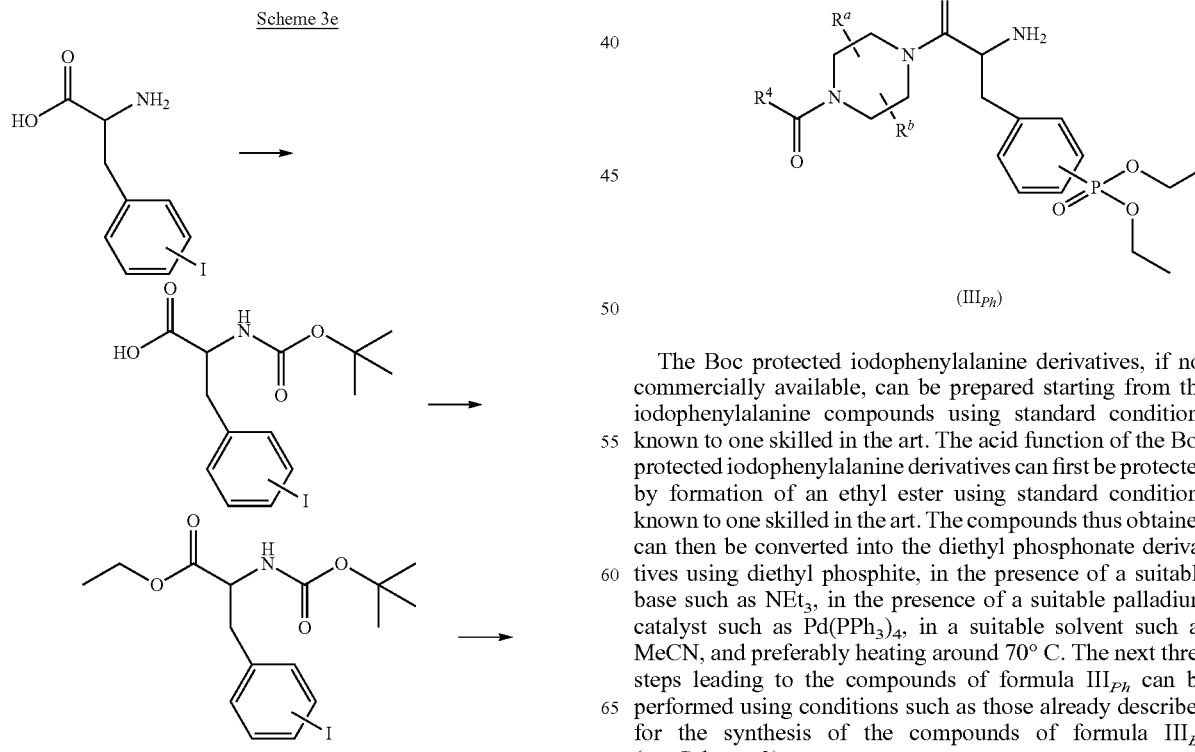

The Boc protected iodophenylalanine derivatives, if not commercially available, can be prepared starting from the iodophenylalanine compounds using standard conditions known to one skilled in the art. The acid function of the Boc protected iodophenylalanine derivatives can first be protected by formation of an ethyl ester using standard conditions known to one skilled in the art. The compounds thus obtained can then be converted into the diethyl phosphonate derivatives using diethyl phosphite, in the presence of a suitable base such as NEt$_3$, in the presence of a suitable palladium catalyst such as Pd(PPh$_3$)$_4$, in a suitable solvent such as MeCN, and preferably heating around 70° C. The next three steps leading to the compounds of formula III$_{Ph}$ can be performed using conditions such as those already described for the synthesis of the compounds of formula III$_{B1}$ (see Scheme 3).

Preparation of the Compounds of Formula IV

The compounds of formula IV wherein R¹ is phenyl can be prepared using the reaction shown in Scheme 4 hereafter.

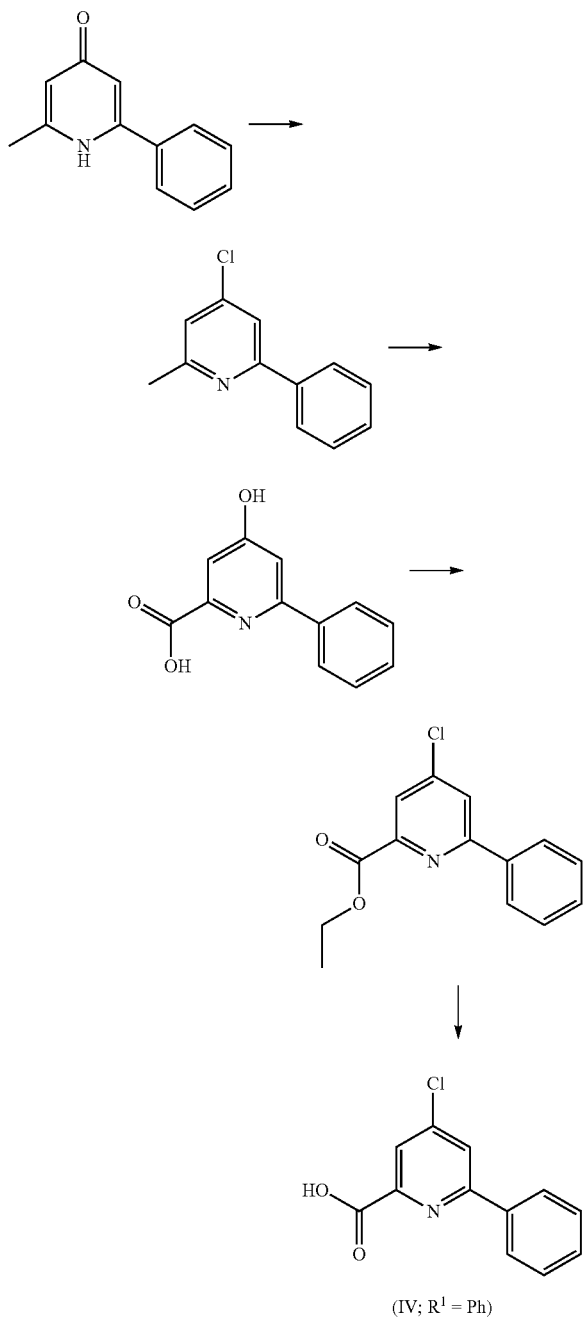

The starting material 2-methyl-6-phenyl-1H-pyridin-4-one is easily accessible using a literature procedure (*J. Med. Chem.* (2004), 47, 4277-4285). It can be chlorinated to yield 4-chloro-2-methyl-6-phenyl-pyridine using standard conditions (e.g. phosphoryl chloride at reflux). 4-chloro-2-methyl-6-phenyl-pyridine can then be oxidized into 4-hydroxy-6-phenyl-pyridine-2-carboxylic acid, preferably by refluxing it in dioxane/water in the presence of selenium dioxide. The resulting compound, when containing EtOH as impurity, can then be chlorinated and esterified by refluxing in POCl₃. Finally, the compound of formula IV wherein R¹ is phenyl can be obtained by standard saponification methods such as those described in Scheme 3.

Similar procedures can be used to obtain compounds of formula IV wherein W is a bond and R¹ is a substituted phenyl group.

Preparation of the Compounds of Formula VI

The compounds of formula VI can be prepared using the reaction shown in Scheme 5 hereafter.

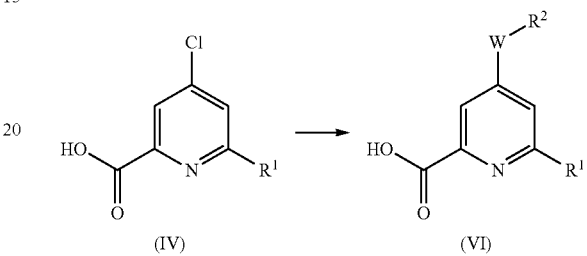

The compounds of formula VI wherein W is —NR³— can thus be obtained by aromatic substitution reaction of the intermediates of formula IV with an amine of formula HNR²R³ using conditions such as those described for the synthesis of compounds of formula II wherein W is —NR³— (see Scheme 2).

Besides, the compounds of formula VI wherein W is —O— can be obtained by aromatic substitution reaction of the intermediates of formula IV with sodium alkoxides of formula NaOR², the reaction being carried in a suitable solvent such as the corresponding alcohol of formula HOR² or THF, and preferably at reflux temperature.

Preparation of the Compounds of Formula VIII

The compounds of formula VIII can be prepared using the route described in WO 2006/114774 (see general preparation routes, preparation of the compounds of formula V, Schemes 5 and 5a).

Particular embodiments of the invention are described in the following Examples, which serve to illustrate the invention in more detail without limiting its scope in any way.

EXAMPLES

Characterisation Methods Used

¹H-NMR (400 MHz) was carried out on a Bruker Avance 400 device. Chemical shifts are given in ppm relative to the solvent used; multiplicities: s=singlet, d=doublet, t=triplet, q=quadruplet, p=pentuplet, hex=hexet, hept=heptet, m=multiplet, br.=broad.

The LC-MS retention times have been obtained using the following elution conditions:

A X-terra® column (MS C18 5 μm, 2.1×50 mm) was used. The two elution solvents were as follows: solvent A=water+ 0.06% formic acid; solvent B=MeCN+0.06% formic acid. The eluent flow rate was 3 ml/min and the characteristics of the eluting mixture proportion in function of the time t from start of the elution are summarized in the table below (a linear gradient being used between two consecutive time points):

|  | t (min) | | | | |
|---|---|---|---|---|---|
|  | 0 | 1 | 1.25 | 1.30 | 1.80 |
| Solvent A (%) | 95 | 5 | 5 | 95 | 95 |
| Solvent B (%) | 5 | 95 | 95 | 5 | 5 |

Preparative LC-MS Methods Used:

The purifications by preparative LC-MS have been performed using either a Phenomenex® column (preparative LC-MS methods (I) to (IV)) or a X-Terra® column (preparative LC-MS method (V)) unless otherwise specified in the relevant Example description, with the general conditions described hereafter.

Preparative LC-MS Methods (I) to (IV)

A Phenomenex® column (Gemini 10u C18 110A Ax 50×21.2 mm) was used. The two elution solvents were as follows: solvent A=water+1% formic acid; solvent B=MeCN+1% formic acid. The eluent flow rate was 50 mL/min. The characteristics of the eluting mixture proportion in function of the time t from start of the elution are summarized in the tables below (a linear gradient being used between two consecutive time points):

I) Preparative LC-MS (I):

|  | t (min) | | | | | | | |
|---|---|---|---|---|---|---|---|---|
|  | 0 | 0.4 | 2.6 | 3 | 3.4 | 3.8 | 3.9 | 5 |
| Solvent A (%) | 75 | 75 | 55 | 55 | 4.5 | 4.5 | 75 | 75 |
| Solvent B (%) | 25 | 25 | 45 | 45 | 95.5 | 95.5 | 25 | 25 |

II) Preparative LC-MS (II):

|  | t (min) | | | | | | | |
|---|---|---|---|---|---|---|---|---|
|  | 0 | 0.4 | 2.6 | 3 | 3.4 | 3.8 | 3.9 | 5 |
| Solvent A (%) | 65 | 65 | 45 | 45 | 4.5 | 4.5 | 65 | 65 |
| Solvent B (%) | 35 | 35 | 55 | 55 | 95.5 | 95.5 | 35 | 35 |

III) Preparative LC-MS (III):

|  | t (min) | | | | | | | |
|---|---|---|---|---|---|---|---|---|
|  | 0 | 0.4 | 2.6 | 3 | 3.4 | 3.8 | 3.9 | 5 |
| Solvent A (%) | 70 | 70 | 50 | 50 | 4.5 | 4.5 | 70 | 70 |
| Solvent B (%) | 30 | 30 | 50 | 50 | 95.5 | 95.5 | 30 | 30 |

IV) Preparative LC-MS (IV):

|  | t (min) | | | | | | | |
|---|---|---|---|---|---|---|---|---|
|  | 0 | 0.4 | 2.6 | 3 | 3.4 | 3.8 | 3.9 | 5 |
| Solvent A (%) | 85 | 85 | 65 | 65 | 4.5 | 4.5 | 85 | 85 |
| Solvent B (%) | 15 | 15 | 35 | 35 | 95.5 | 95.5 | 15 | 15 |

Preparative LC-MS Method (V)

A X-Terra® column (Prep MS C18 OBD™ 10u 30×75 mm) was used. The two elution solvents were as described for the Phenomenex® column. The eluent flow rate was 100 mL. The characteristics of the eluting mixture proportion in function of the time t from start of the elution are summarized in the table below (a linear gradient being used between two consecutive time points):

|  | t (min) | | | | | | | |
|---|---|---|---|---|---|---|---|---|
|  | 0 | 0.6 | 3.3 | 3.9 | 4.5 | 5.1 | 5.2 | 6 |
| Solvent A (%) | 85 | 85 | 65 | 65 | 4.5 | 4.5 | 85 | 85 |
| Solvent B (%) | 15 | 15 | 35 | 35 | 95.5 | 95.5 | 15 | 15 |

Stationary Phases Used for CC:

The purifications by CC have been performed using silica gel unless otherwise specified. The reverse phase used is ISOLUTE® C18 from Biotage. RP 18 is the abbreviation for LiChroprep® RP-18 (15-25 µM), Merck.

Example 1

4-((R)-2-{[4-((S)-3-methoxy-pyrrolidin-1-yl)-6-phenyl-pyridine-2-carbonyl]-amino}-4-phosphono-butyryl)-piperazine-1-carboxylic acid ethyl ester 1.1. (S)-3-hydroxypyrrolidine-1-carboxylic acid tert-butyl ester Di-tert-butyl-dicarbonate (27.5 g) was added portionwise to a solution of (S)-3-hydroxypyrrolidine (10 g) and NEt$_3$ (32 ml) in DCM (240 mL). The reaction mixture was stirred overnight at RT. Water was added and the org. phase was separated. It was washed with sat. aq. NH$_4$Cl, sat. aq. NaHCO$_3$ and brine. The org. phase was dried (Na$_2$SO$_4$) and evaporated off to afford the desired compound (21.4 g).

$^1$H-NMR (CDCl$_3$): 4.43 (br. s, 1H); 3.40 (m, 4H); 2.70 (m, 1H); 1.93 (m, 2H); 1.46 (s, 9H).

1.2. (S)-3-methoxy-pyrrolidine-1-carboxylic acid tert-butyl ester

To an ice-cold solution of intermediate 1.1 (22 g) in THF (300 mL) was added NaH (7.7 g, 55% dispersion in mineral oil) portionwise. The reaction mixture was stirred for 30 min at RT, cooled down to 0° C. and MeI (11 mL) was added dropwise. Stirring was continued for additional 2 h at RT. Water and ethanolamine (14 mL) were added to the reaction mixture that was stirred for 15 min. The org. phase was separated and the aq. phase was extracted with DCM three times. The combined org. phases were washed with brine, dried (Na$_2$SO$_4$) and evaporated off to afford a yellow oil (27.5 g).

$^1$H-NMR (CDCl$_3$): 3.94 (br. s, 1H); 3.44 (m, 4H); 3.35 (s, 3H); 1.99 (m, 2H); 1.48 (s, 9H).

1.3. (S)-3-methoxy-pyrrolidine hydrochloride salt

Intermediate 1.2 (27.5 g) was dissolved in 1M HCl in EA (300 mL) and 3M HCl in EA (50 mL) was added. The reaction mixture was stirred overnight at RT and the solvent was evaporated off. The residue was taken up in Et$_2$O (500 mL)

and the compound precipitated out. The suspension was stirred for 1 h, filtered off and the powder washed with Et₂O. HV drying afforded the desired hydrochloride salt (13.9 g).

¹H-NMR (CDCl₃): 9.84 (br. s, 1H); 4.10 (br s, 1H); 3.43 (m, 4H); 3.33 (s, 3H); 2.19 (m, 1H); 2.04 (m, 1H).

1.4. (Z)-4-phenylamino-pent-3-en-2-one

A solution of 2,4-pentanedione (51.5 mL), aniline (45.6 mL) and a catalytic amount of para-toluenesulfonic acid monohydrate (0.95 g) in toluene (500 ml) was refluxed for 3.5 h in a round bottom flask equipped with a Dean-Stark apparatus and condenser. The solution was concentrated to dryness to give the desired compound as an orange oil (89.3 g).

LC-MS: $t_R$=0.90 min; [M+H]⁺: 176.14.

1.5. 2-methyl-6-phenyl-1H-pyridin-4-one

To a −78° C. cooled solution of 2,2,6,6-tetramethylpiperidine (157 g) in THF (830 mL) was added n-butyllithium (1.6 M in hexane, 697 mL) over 45 min. After 25 min stirring at −78° C. a solution of intermediate 1.4 (63 g) in THF (200 mL) was added to the mixture over 25 min, followed by a solution of benzonitrile (47.9 mL) in THF (200 mL) over 30 min. The cooling bath was removed and the mixture was allowed to warm to −56° C. over 1.5 h. HCl (32%, 186.5 g) was added, followed by water (400 mL) and THF (200 mL). The phases were separated. The org. phase was washed with water and HCl (32%, 150 mL) was added, followed by water (200 mL). The phases were separated and the aq. phase was evaporated off. The residue was taken up in toluene and evaporated to dryness to afford 249 g of the desired compound with 13% purity. No further purification was performed.

LC-MS: $t_R$=0.64 min; [M+H]⁺: 186.25.

1.6. 4-chloro-2-methyl-6-phenyl-pyridine

Intermediate 1.5 (233 g) was dissolved in POCl₃ (83 mL) and DMF was added (0.15 mL). The mixture was refluxed for 4 h and cooled down. Toluene was added and the mixture was evaporated off. The residue was taken up in EA/water, and 32% NaOH was added until pH 7. The phases were separated and the aq. phase was washed with EA. The combined org. layers were evaporated to dryness. The crude was purified by CC (EA/Hept 1/9) and the obtained oil was taken up in TBME. The org. layer was washed with 0.5 M HCl, sat. NaHCO₃, water and was evaporated to dryness to afford the desired compound as an orange oil (31.2 g).

LC-MS: $t_R$=0.83 min; [M+H]⁺: 203.92.

1.7. 4-hydroxy-6-phenyl-pyridine-2-carboxylic acid

To selenium dioxide (33.8 g) was added intermediate 1.6 (31 g) followed by dioxane (165 mL). The mixture was heated up to reflux. After 4.5 h, water (0.274 mL) was added and the heating was continued overnight. Water (2.5 mL) was added and the mixture was further refluxed for 7 h. The mixture was cooled down to 0° C., selenium dioxide (16.9 g) was added and the mixture was stirred at RT for 90 h. Celite was added and the resulting mixture was filtered over a pad of Celite. The filter cake was washed with MeOH and the solvents were evaporated off. The crude was suspended in isopropylacetate (400 mL) and heated up to reflux for 1 h. Isopropylacetate was removed and EtOH (400 mL) was added and heated again to reflux for 1 h. EtOH was removed and EtOH (400 mL) and HCl (32%, 30 mL) were added. The mixture was heated at reflux for 3 h and evaporated off to afford the desired compound still containing EtOH (52 g).

LC-MS: $t_R$=0.60 min; [M+H]⁺: 216.11.

1.8. 4-chloro-6-phenyl-pyridine-2-carboxylic acid ethyl ester

Intermediate 1.7 (34 g, containing EtOH) was dissolved in POCl₃ (72 mL) and the mixture was heated up to reflux for 3 h. POCl₃ was distilled off, the remaining residue was diluted with DCM and water was added. The layers were filtered and separated. The aq. layer was washed with DCM. The combined org. layers were evaporated off. The crude was purified by CC (isopropylacetate/methylcyclohexane 1/3) to give the desired ethyl ester compound as a brownish solid (29.11 g).

LC-MS: $t_R$=1.04 min; [M+H]⁺: 262.10.

1.9. Sodium 4-chloro-6-phenyl-pyridine-2-carboxylate

NaOH (32% in water, 50 mL) was added to a solution of intermediate 1.8 (20.1 g) in EtOH/water (2/1, 150 ml). The mixture was stirred for 1 h at RT and EtOH was evaporated off. The suspension was filtered off. The aqueous mother liquor was washed with isopropylacetate, acidified with 32% HCl solution and extracted with DCM. The filtered solid was added to a mixture of 32% HCl solution and DCM. The layers were separated and the aqueous layer was washed with DCM. All organic layers were combined and evaporated to dryness to give 20 g of black oil. The oil was taken up in MeOH (150 mL) and NaOH (32% in water, 10 mL) was added. Water (150 mL) was added giving a suspension. MeOH was evaporated off, the suspension was filtered off and the solid washed with water. After HV drying, the desired compound were obtained as a white powder (17 g).

LC-MS: $t_R$=0.91 min; [M+H]⁺: 234.09.

1.10. 4-((S)-3-methoxy-pyrrolidin-1-yl)-6-phenyl-pyridine-2-carboxylic acid

A solution of intermediate 1.3 (963 mg), intermediate 1.9 (1.49 g) and DIPEA (2.2 mL) in THF (2 mL) was heated in a microwave oven at 110° C. for 10 h and at 140° C. for 6 h. Water was added and the mixture was extracted with EA. The aq. phase was acidified to pH 5 with 1M HCl and extracted with DCM. The combined org. phases were dried (Na₂SO₄) and evaporated off. The crude was purified by CC (eluant A: EA; eluant B: MeOH; gradient: 20% to 40% B) to afford the desired compound as a brownish foam (1.06 g).

LC-MS: $t_R$=0.70 min; [M+H]⁺: 299.08.

1.11. (R)-2-benzyloxycarbonylamino-4-hydroxy-butyric acid

To an ice-cooled solution of H-Hse-OH (5 g) in dioxane/2M NaOH (168 mL/42 mL) was added benzyl chloroformate (6.7 mL) dropwise over 15 min. The reaction mixture was allowed to warm to RT and was stirred overnight at RT. The solvent was evaporated off and the aq. residue was extracted with Et₂O and acidified with a 2M HCl solution. The aq. phase was extracted with DCM. The DCM layers were combined, washed with water, dried (Na₂SO₄) and evaporated off to give the desired product as a white powder (6.2 g).

LC-MS: $t_R$=0.71 min; [M+H]⁺: 254.37.

1.12. (R)-2-benzyloxycarbonylamino-4-hydroxy-butyric acid dicyclohexylamine salt To a solution of intermediate 1.11 (6.2 g) in EtOH (41 mL) was added dropwise dicyclohexylamine (3.7 mL). The solvent was removed and the white powder was suspended in Et$_2$O. The suspension was filtered off and the white solid (7.38 g) was dried in vacuo.

LC-MS: $t_R$=0.66 min; [M+H]$^+$: 254.07.

1.13. (R)-2-benzyloxycarbonylamino-4-hydroxy-butyric acid methyl ester

MeI (3 mL) was added dropwise to a suspension of intermediate 1.12 (7.38 g) in anhydrous DMF (112 mL). The reaction mixture was stirred for 48 h at RT. MeI (3 mL) was added, and the reaction mixture was stirred overnight. The solvent was removed. The residue was taken up in EA/water and the org. phase was washed with a sodium thiosulfate solution, dried (Na$_2$SO$_4$) and evaporated off. The crude was purified by CC (Et$_2$O) to give the desired compound as white powder (3.1 g).

LC-MS: $t_R$=0.79 min; [M+H]$^+$: 268.12.

1.14. (R)-2-benzyloxycarbonylamino-4-bromo-butyric acid methyl ester

PPh$_3$ on resin (1.6 mmol/g, 16 g) was added to an ice-cooled solution of intermediate 1.13 (3.1 g) and CBr$_4$ (8.7 g) in anhydrous DCM (150 mL). The reaction mixture was stirred at 0° C. for 2 h and was allowed to warm to RT. The resin was filtered off and the solution evaporated off. The crude was purified by CC (EA/Hept 0/1 to 1/0) to give the desired compound as a colourless oil (968 mg).

LC-MS: $t_R$=0.99 min; [M+H]$^+$: 330.02.

1.15. (R)-2-benzyloxycarbonylamino-4-(diethoxy-phosphoryl)-butyric acid methyl ester Intermediate 1.14 (1.39 g) was dissolved in triethyl phosphite (9.9 mL). The mixture was heated at 130° C. overnight and evaporated to dryness. The crude was purified by CC (Hept/EA 1/3 to 0/1 followed by EA/MeOH 9/1) to give a colourless oil (1.24 g).

LC-MS: $t_R$=0.91 min; [M+H]$^+$: 387.93.

1.16. (R)-2-benzyloxycarbonylamino-4-(diethoxy-phosphoryl)-butyric acid

An aq. solution of lithium hydroxide hydrate (268 mg in 3.2 mL) was added to a solution of intermediate 1.15 (1.24 g) in THF (13 mL). The reaction mixture was stirred at RT overnight and DCM and a 1M HCl solution (60 mL) were added. The phases were separated and the aq. phase was extracted three times with DCM. The org. phases were combined, dried (Na$_2$SO$_4$) and evaporated off to give the desired product as a colourless resin (1.19 g).

LC-MS: $t_R$=0.83 min; [M+H]$^+$: 374.07.

1.17. 4-[(R)-2-benzyloxycarbonylamino-4-(diethoxy-phosphoryl)-butyryl]-piperazine-1-carboxylic acid ethyl ester To a solution of intermediate 1.16 (310 mg) in THF/DCM (1 mL/4 mL) were added EDCI hydrochloride (191 mg), HOBT hydrate (152 mg) and DIPEA (0.156 mL). After stirring at RT for 5 min, 1-ethoxycarbonylpiperazine (134 mg) was added and the stirring was continued overnight at RT. DCM and water were added. The phases were separated. The org. phase was washed with sat. aq. Na$_2$CO$_3$, with aq. 1M NaHSO$_4$, with brine, was dried (Na$_2$SO$_4$) and evaporated off to afford the desired compound as a yellow oil (229 mg).

LC-MS: $t_R$=0.90 min; [M+H]$^+$: 514.09.

1.18. 4-[(R)-2-amino-4-(diethoxy-phosphoryl)-butyryl]-piperazine-1-carboxylic acid ethyl ester Intermediate 1.17 (200 mg) was hydrogenated in MeOH (3 mL) with Pd/C (wet, 5%, 25 mg) for 24 h. The mixture was filtered through Celite and evaporated off. HV drying afforded the desired compound as a pale yellow oil (138 mg).

LC-MS: $t_R$=0.65 min; [M+H]$^+$: 380.59.

1.19. 4-((R)-4-(diethoxy-phosphoryl)-2-{[4-((S)-3-methoxy-pyrrolidin-1-yl)-6-phenyl-pyridine-2-carbonyl]-amino}-butyryl)-piperazine-1-carboxylic acid ethyl ester To a solution of intermediate 1.10 (78 mg) and intermediate 1.18 (100 mg) in DCM (1 mL) was added PyBOP (151 mg) and DIPEA (0.05 mL). The solution was stirred at RT until completion. It was diluted with DCM and washed with water and brine. The org. phase was dried (Na$_2$SO$_4$) and evaporated off. The crude was purified by preparative LC-MS (I) to afford the desired product as a yellow oil (113 mg).

LC-MS: $t_R$=0.84 min; [M+H]$^+$: 660.66.

1.20. 4-((R)-2-{[4-((S)-3-methoxy-pyrrolidin-1-yl)-6-phenyl-pyridine-2-carbonyl]-amino}-4-phosphono-butyryl)-piperazine-1-carboxylic acid ethyl ester To a solution of intermediate 1.19 (55 mg) in anhydrous MeCN (1 mL) was added trimethylsilyl bromide (0.225 mL) dropwise. The reaction mixture was allowed to warm to RT and was stirred at RT until completion. Water (1 mL) was added, the mixture was stirred until complete hydrolysis and evaporated off. The crude was purified by preparative LC-MS (IV) to afford a white powder (8 mg).

LC-MS: $t_R$=0.75 min; [M+H]$^+$: 604.47.

Example 2

4-((R)-2-{[4-((S)-3-methoxy-pyrrolidin-1-yl)-6-phenyl-pyridine-2-carbonyl]-amino}-4-phosphono-butyryl)-piperazine-1-carboxylic acid butyl ester

2.1. Piperazine-1,4-dicarboxylic acid butyl ester tert-butyl ester

To a solution of piperazine-1-carboxylic acid tert-butyl ester (150 g) in DCM (1.05 L) cooled at 4° C. was added NEt$_3$ (123.6 mL) followed by n-butyl chloroformate (107 mL) dropwise over 30 min. The cooling bath was removed and the reaction mixture was allowed to warm to RT over 2.5 h. Water was added, the phases were separated and the aq. phase was extracted with DCM. The combined org. phases were dried (Na$_2$SO$_4$) and evaporated off to give 242.8 g of oil. The compound was engaged directly in the next step.

TLC: (EA/Hept 1/1) Rf=0.7.

2.2. Piperazine-1-carboxylic acid butyl ester hydrochloride salt

To a cooled (15° C.) solution of intermediate 2.1 (230.5 g) in MeOH (1 L) was added 4M HCl in dioxane (604 mL). The mixture was stirred overnight at RT and evaporated to dryness. The residue was suspended in TBME (800 mL) and the mixture was stirred for 30 min and filtered off. The solid was dried under HV to afford a white solid (176 g).
$^1$H-NMR (CDCl$_3$): 6.12 (br. s, 1H); 5.71 (br. s, 1H); 4.11 (m, 4H); 3.77 (s, 3H); 2.33 (m, 2H); 1.41 (s, 9H); 1.33 (m, 6H).

2.3. 4-[(R)-2-benzyloxycarbonylamino-4-(diethoxy-phosphoryl)-butyryl]-piperazine-1-carboxylic acid butyl ester This compound was prepared using a method analogous to that of Example 1, step 1.17, intermediate 2.2 replacing 1-ethoxycarbonylpiperazine.
LC-MS: $t_R$=0.97 min; [M+H]$^+$: 542.05.

2.4. 4-[(R)-2-amino-4-(diethoxy-phosphoryl)-butyryl]-piperazine-1-carboxylic acid butyl ester This compound was prepared using a method analogous to that of Example 1, step 1.18, intermediate 2.3 replacing intermediate 1.17.
LC-MS: $t_R$=0.73 min; [M+H]$^+$: 408.61.

2.5. 4-((R)-4-(diethoxy-phosphoryl)-2-{[4-((S)-3-methoxy-pyrrolidin-1-yl)-6-phenyl-pyridine-2-carbonyl]-1-amino}-butyryl)-piperazine-1-carboxylic acid butyl ester This compound was prepared using a method analogous to that of Example 1, step 1.19, intermediate 2.4 replacing intermediate 1.18. The compound was purified by preparative LC-MS (I).
LC-MS: $t_R$=0.90 min; [M+H]$^+$: 688.74.

2.6. 4-((R)-2-{[4-((S)-3-methoxy-pyrrolidin-1-yl)-6-phenyl-pyridine-2-carbonyl]-amino}-4-phosphono-butyryl)-piperazine-1-carboxylic acid butyl ester This compound was prepared using a method analogous to that of Example 1, step 1.20, intermediate 2.5 replacing intermediate 1.19. The compound was purified by preparative LC-MS (IV).
LC-MS: $t_R$=0.80 min; [M+H]$^+$: 632.11.

Example 3

4-((R)-2-{[4-(4-methoxy-phenyl)-6-phenyl-pyridine-2-carbonyl]-amino}-3-phosphono-propionyl)-piperazine-1-carboxylic acid ethyl ester

3.1. (R)-2-tert-butoxycarbonylamino-3-(diethoxy-phosphoryl)-propionic acid methyl ester Boc-3-iodo-L-Ala-OMe (10 g) was dissolved in triethyl phosphite (79.7 mL). The mixture was heated at 140° C. for 15 h and evaporated to dryness to give the desired compound (9.37 g). It was used in the next step without further purification.
$^1$H-NMR (CDCl$_3$): 6.12 (br. s, 1H); 5.71 (br. s, 1H); 4.11 (m, 4H); 3.77 (s, 3H); 2.33 (m, 2H); 1.41 (s, 9H); 1.33 (m, 6H).

3.2. (R)-2-tert-butoxycarbonylamino-3-(diethoxy phosphoryl)propionic acid

This compound was prepared using a method analogous to that of Example 1, step 1.16, intermediate 3.1 replacing intermediate 1.15. The compound was however purified by recrystallization with isopropanol.
LC-MS: $t_R$=0.72 min; [M+H]$^+$: 326.08.

3.3. 4-[(R)-2-tert-butoxycarbonylamino-3-(diethoxy-phosphoryl)-propionyl]-piperazine-1-carboxylic acid ethyl ester This compound was prepared using a method analogous to that of Example 1, step 1.17, intermediate 3.2 replacing intermediate 1.16.
LC-MS: $t_R$=0.86 min; [M+H]$^+$: 466.46.

3.4. 4-[(R)-2-amino-3-(diethoxy-phosphoryl)-propionyl]-piperazine-1-carboxylic acid ethyl ester To a solution of intermediate 3.3 (1.520 g) in DCM (1.38 mL) cooled at 10° C. was added TFA (2.29 mL) over 15 min. After completion of the addition, the cooling bath was removed and the mixture was stirred overnight at RT. The mixture was cooled down to 0° C., quenched by the addition of 2M NaOH until pH 12 and diluted with DCM. The phases were separated. The org. phase was extracted with DCM, dried (Na$_2$SO$_4$) and evaporated off to afford the desired compound (807 mg).
LC-MS: $t_R$=0.64 min; [M+H]$^+$: 366.43.

3.5. 4-[(R)-2-[(6-chloro-2-phenyl-pyrimidine-4-carbonyl)-amino]-3-(diethoxy-phosphoryl)-propionyl]-piperazine-1-carboxylic acid ethyl ester This compound was prepared using a method analogous to that of Example 1, step 1.19, intermediate 3.4 replacing intermediate 1.18 and intermediate 1.9 replacing intermediate 1.10. The compound was purified by CC (eluent A: DCM; eluent B: MeOH; first CC: 1% to 10% B; second CC: 2% B).
LC-MS: $t_R$=1.01 min; [M+H]$^+$: 581.44.

3.6. 4-((R)-3-(diethoxy-phosphoryl)-2-{[4-(4-methoxy-phenyl)-6-phenyl-pyridine-2-carbonyl]-amino}-propionyl)-piperazine-1-carboxylic acid ethyl ester A mixture of intermediate 3.5 (100 mg), 4-methoxyphenylboronic acid (32 mg) and Pd(PPh$_3$)$_4$ (6 mg) in DME (1 mL) and 2M Na$_2$CO$_3$ (0.173 mL) was stirred at 80° C. under argon overnight. The mixture was filtered through Celite, the cake was washed with EA and the solvents were evaporated off. The crude was purified by CC (eluent A: DCM; eluent B: MeOH; gradient: 2% to 20% B) to afford the desired compound (80 mg).
LC-MS: $t_R$=1.07 min; [M+H]$^+$: 653.68.

3.7. 4-((R)-2-{[4-(4-methoxy-phenyl)-6-phenyl-pyridine-2-carbonyl]-amino}-3 phosphono-propionyl)-piperazine-1-carboxylic acid ethyl ester A solution of intermediate 3.6 (80 mg) in 4M HCl in dioxane (2.5 mL) and water (0.25 mL) was stirred at RT until completion of the reaction. Toluene was added and the mixture was evaporated off. The crude was purified by preparative LC-MS (II) to afford of the desired compound (32 mg).
LC-MS: $t_R$=0.93 min; [M+H]$^+$: 597.71.

Example 4

4-[(R)-2-[(6-phenyl-4-thiophen-3-yl-pyridine-2-carbonyl)-amino]-3-phosphono-propionyl]-piperazine-1-carboxylic acid ethyl ester

4.1. 4-{(R)-3-(diethoxy-phosphoryl)-2-[(6-phenyl-4-thiophen-3-yl-pyridine-2-carbonyl)-amino]-propionyl}-piperazine-1-carboxylic acid ethyl ester This compound was prepared using a method analogous to that of Example 3, step 3.6, thiophene-3-boronic acid replacing 4-methoxyphenylboronic acid.
LC-MS: $t_R$=1.05 min; [M+H]$^+$: 629.67.

4.2. 4-{(R)-2-[(6-phenyl-4-thiophen-3-yl-pyridine-2-carbonyl)-amino]-3 phosphono-propionyl}-piperazine-1-carboxylic acid ethyl ester This compound was prepared using a method analogous to that of Example 3, step 3.7, intermediate 4.1 replacing intermediate 3.6. The compound was purified by preparative LC-MS (II).
LC-MS: $t_R$=0.91 min; [M+H]$^+$: 573.50.

Example 5

4-[(R)-2-[(4,6-diphenyl-pyridine-2-carbonyl)-amino]-3-phosphono-propionyl]-piperazine-1-carboxylic acid ethyl ester

5.1. 4-{(R)-3-(diethoxy-phosphoryl)-2-[(4,6-diphenyl-pyridine-2-carbonyl)-amino]-propionyl}-piperazine-1-carboxylic acid ethyl ester This compound was prepared using a method analogous to that of Example 3, step 3.6, phenylboronic acid replacing 4-methoxyphenylboronic acid.
LC-MS: $t_R$=1.06 min; [M+H]$^+$: 623.57.

5.2. 4-{(R)-2-[(4,6-diphenyl-pyridine-2-carbonyl)-amino]-3-phosphono-propionyl}-piperazine-1-carboxylic acid ethyl ester This compound was prepared using a method analogous to that of Example 3, step 3.7, intermediate 5.1 replacing intermediate 3.6. The compound was purified by preparative LC-MS (II), followed by CC (reverse phase; eluent A: water/TFA 100/1; eluent B: MeCN/TFA 100/1; gradient: 5% to 90% B).
LC-MS: $t_R$=0.92 min; [M+H]$^+$: 567.51.

Example 6

4-[(R)-2-[(4-cyclopropyl-6-phenyl-pyridine-2-carbonyl)-amino]-3-phosphono-propionyl]-piperazine-1-carboxylic acid ethyl ester

6.1. 4-[(R)-2-[(4-cyclopropyl-6-phenyl-pyridine-2-carbonyl)-amino]-3-(diethoxy-phosphoryl)-propionyl]-piperazine-1-carboxylic acid ethyl ester This compound was prepared using a method analogous to that of Example 3, step 3.6, cyclopropylboronic acid replacing 4-methoxyphenylboronic acid.
LC-MS: $t_R$=1.01 min; [M+H]$^+$: 587.69.

6.2. 4-{(R)-2-[(4-cyclopropyl-6-phenyl-pyridine-2-carbonyl)-amino]-3 phosphono-propionyl}-piperazine-1-carboxylic acid ethyl ester This compound was prepared using a method analogous to that of Example 3, step 3.7, intermediate 6.1 replacing intermediate 3.6. The compound was purified by preparative LC-MS (III), followed by CC (reverse phase; eluent A: water/TFA 100/1; eluant B: MeCN/TFA 100/1; gradient: 5% to 90% B).
LC-MS: $t_R$=0.87 min; [M+H]$^+$: 531.46.

Example 7

4-((R)-2-{[4-((R)-3-hydroxy-pyrrolidin-1-yl)-6-phenyl-pyridine-2-carbonyl]-amino}-3-phosphono-propionyl)-piperazine-1-carboxylic acid ethyl ester

7.1. 4-((R)-3-(ethoxy-hydroxy-phosphoryl)-2-{[4-((R)-3-hydroxy-pyrrolidin-1-yl)-6-phenyl-pyridine-2-carbonyl]-amino}-propionyl)-piperazine-1-carboxylic acid ethyl ester A solution of intermediate 3.5 (50 mg) and (R)-3-pyrrolidinol (31 mg) in THF (1 mL) was heated in a microwave oven at 160° C. for 30 min. The solvent was evaporated off and the crude was used directly in the next step.
LC-MS: $t_R$=0.70 min; [M+H]$^+$: 604.40.

7.2. 4-((R)-2-{[4-((R)-3-hydroxy-pyrrolidin-1-yl)-6-phenyl-pyridine-2-carbonyl]-amino}-3-phosphono-propionyl)-piperazine-1-carboxylic acid ethyl ester This compound was prepared using a method analogous to that of Example 1, step 1.20, intermediate 7.1 replacing intermediate 1.19. The compound was however purified by preparative LC-MS (IV).
LC-MS: $t_R$=0.68 min; [M+H]$^+$: 576.20.

Example 8

4-((R)-2-{[4-(2-methoxy-ethylamino)-6-phenyl-pyridine-2-carbonyl]-amino}-3-phosphono-propionyl)-piperazine-1-carboxylic acid ethyl ester

8.1. 4-((R)-3-(ethoxy-hydroxy-phosphoryl)-2-{[4-(2-methoxy-ethylamino)-6-phenyl-pyridine-2-carbonyl]-amino}-propionyl)-piperazine-1-carboxylic acid ethyl ester A solution of intermediate 3.5 (50 mg) and 2-methoxy-ethylamine (0.5 mL) in THF (1 mL) was heated in a microwave oven at 160° C. for 5 h. The solvent was evaporated off and the crude was used directly in the next step.

LC-MS: $t_R$=0.73 min; [M+H]$^+$: 592.50.

8.2. 4-((R)-2-{[4-(2-methoxy-ethylamino)-6-phenyl-pyridine-2-carbonyl]-amino}-3-phosphono-propionyl)-piperazine-1-carboxylic acid ethyl ester This compound was prepared using a method analogous to that of Example 1, step 1.20, intermediate 8.1 replacing intermediate 1.19. The compound was however purified by preparative LC-MS (IV).

LC-MS: $t_R$=0.71 min; [M+H]$^+$: 564.30.

Example 9

4-((R)-2-{[4-(2-hydroxy-ethylamino)-6-phenyl-pyridine-2-carbonyl]-amino}-3-phosphono-propionyl)-piperazine-1-carboxylic acid ethyl ester 9.1. 4-((R)-3-(ethoxy-hydroxy-phosphoryl)-2-{[4-(2-hydroxy-ethylamino)-6-phenyl-pyridine-2-carbonyl]-amino}-propionyl)-piperazine-1-carboxylic acid ethyl ester This compound was prepared using a method analogous to that of Example 8, step 8.1, ethanolamine replacing 2-methoxy-ethylamine.

LC-MS: $t_R$=0.69 min; [M+H]$^+$: 578.58.

9.2. 4-((R)-2-{[4-(2-hydroxy-ethylamino)-6-phenyl-pyridine-2-carbonyl]-amino}-3-phosphono-propionyl)-piperazine-1-carboxylic acid ethyl ester This compound was prepared using a method analogous to that of Example 1, step 1.20, intermediate 9.1 replacing intermediate 1.19. The compound was however purified by preparative LC-MS (IV).

LC-MS: $t_R$=0.67 min; [M+H]$^+$: 550.37.

Example 10

4-[(R)-2-({4-[(2-methoxy-ethyl)-methyl-amino]-6-phenyl-pyridine-2-carbonyl}-amino)-3-phosphono-propionyl]-piperazine-1-carboxylic acid ethyl ester 10.1. 4-[(R)-3-(ethoxy-hydroxy-phosphoryl)-2-({4-[(2-methoxy-ethyl)-methyl-amino]-6-phenyl-pyridine-2-carbonyl}-amino)-propionyl]-piperazine-1-carboxylic acid ethyl ester A solution of intermediate 3.5 (50 mg) and N-(2-methoxyethyl)methylamine (39 µL) in NMP (1 mL) was heated in a microwave oven at 120° C. for 1 h. 10 eq. of N-(2-methoxyethyl)methylamine were added and the mixture was heated at 120° C. for 8 h. 10 more eq. of N-(2-methoxyethyl)methylamine were added and the mixture was heated at 120° C. for 6 h. The solvent was removed and the crude was used directly in the next step.

LC-MS: $t_R$=0.74 min; [M+H]$^+$: 606.40.

10.2. 4-[(R)-2-({4-[(2-methoxy-ethyl)-methyl-amino]-6-phenyl-pyridine-2 carbonyl}-amino)-3-phosphono-propionyl]-piperazine-1-carboxylic acid ethyl ester This compound was prepared using a method analogous to that of Example 1 step 1.20, intermediate 10.1 replacing intermediate 1.19. The compound was however purified by preparative LC-MS (IV).

LC-MS: $t_R$=0.71 min; [M+H]$^+$: 578.58.

Example 11

4-[(R)-2-[(4-benzylamino-6-phenyl-pyridine-2-carbonyl)-amino]-3-phosphono-propionyl]-piperazine-1-carboxylic acid ethyl ester 11.1. 4-[(R)-2-[(4-benzylamino-6-phenyl-pyridine-2-carbonyl)-amino]-3-(ethoxy-hydroxy-phosphoryl)-propionyl]-piperazine-1-carboxylic acid ethyl ester A solution of intermediate 3.5 (50 mg) and benzylamine (192 µL) in NMP (1 mL) was heated in a microwave oven at 120° C. for 12 h. 20 eq. of benzylamine were added and the mixture was heated at 120° C. for 6 h. The solvent was removed and the crude was used directly in the next step.

LC-MS: $t_R$=0.89 min; [M+H]$^+$: 624.66.

11.2. 4-{(R)-2-[(4-benzylamino-6-phenyl-pyridine-2-carbonyl)-amino]-3-phosphono-propionyl}-piperazine-1-carboxylic acid ethyl ester This compound was prepared using a method analogous to that of Example 1, step 1.20, intermediate 11.1 replacing intermediate 1.19. The compound was however purified by preparative LC-MS (IV).

LC-MS: $t_R$=0.78 min; [M+H]$^+$: 596.06.

Example 12

4-(-2-{[4-((S)-3-methoxy-pyrrolidin-1-yl)-6-phenyl-pyridine-2-carbonyl]-amino}-2-phosphono-acetyl)-piperazine-1-carboxylic acid butyl ester 12.1. Benzyloxycarbonylamino-(dimethoxy-phosphoryl)-acetate lithium salt Cbz-α-phosphinoglycine trimethyl ester (1.6 g) was dissolved in EtOH (5 mL) and treated with a solution of LiOH.H$_2$O (408 mg) in MeOH/H$_2$O (5 mL/2 mL). The mixture was stirred at 0° C. for 30 min and the solvent was removed. The crude (1.5 g) was used directly in the next step.

LC-MS: $t_R$=0.75 min; [M+H]$^+$: 318.06.

12.2. 4-[2-benzyloxycarbonylamino-2-(dimethoxy-phosphoryl)-acetyl]-piperazine-1-carboxylic acid butyl ester To a solution of intermediate 12.1 (1.5 g) in DCM (5 mL) was added DIPEA (3.4 mL) and HATU (2.2 g). After stirring at RT for 10 min, intermediate 2.2 (1.1 g) was added. The reaction mixture was stirred overnight at RT and H$_2$O was added. The phases were separated, the org. phase was washed with brine, dried (MgSO$_4$) and evaporated off. The crude was purified by CC (Hept/EA 2/8) to afford the desired compound (1.1 g).

LC-MS: $t_R$=0.95 min; [M+H]$^+$: 486.01.

12.3. 4-[2-amino-2-(dimethoxy-phosphoryl)-acetyl]-piperazine-1-carboxylic acid butyl ester This compound was prepared using a method analogous to that of Example 1, step 1.18, intermediate 12.2 replacing intermediate 1.17.

LC-MS: $t_R$=0.67 min; [M+H]$^+$: 352.55.

12.4. 4-(2-(dimethoxy-phosphoryl)-2-{[4-((S)-3-methoxy-pyrrolidin-1-yl)-6-phenyl-pyridine-2-carbonyl]-amino}-acetyl)-piperazine-1-carboxylic acid butyl ester This compound was prepared using a method analogous to that of Example 1, step 1.19, intermediate 12.3 replacing intermediate 1.18. The crude was purified by CC (EA/MeOH 1/0 to 1/9).

LC-MS: $t_R$=0.90 min; [M+H]$^+$: 632.31.

12.5. 4-(-2-{[4-((S)-3-methoxy-pyrrolidin-1-yl)-6-phenyl-pyridine-2-carbonyl]-amino}-2-phosphono-acetyl)-piperazine-1-carboxylic acid butyl ester This compound was prepared using a method analogous to that of Example 1, step 1.20, intermediate 12.4 replacing intermediate 1.19. The crude was purified by CC (reverse phase; eluant A: H$_2$O/TFA 100/1; eluant B: MeCN/TFA 100/1; gradient: 5 to 90% B).

LC-MS: $t_R$=0.77 min; [M+H]$^+$: 604.47.

Example 13

4-((S)-2-{[4-((S)-3-methoxy-pyrrolidin-1-yl)-6-phenyl-pyridine-2-carbonyl]-amino}-5-phosphono-pentanoyl)-piperazine-1-carboxylic acid butyl ester

13.1. (S)-2-benzyloxycarbonylamino-5-hydroxy-pentanoic acid methyl ester

To a cold (−15° C.) solution of Cbz-Glu-OMe (1.5 g) in THF (70 mL) was added N-methylmorpholine (0.616 mL) followed by isobutyl chloroformate (0.731 mL) dropwise. After 30 min stirring at −15° C., NaBH$_4$ (576 mg) was added, followed MeOH dropwise. The reaction mixture was stirred at −10° C. for 15 min and quenched by the addition of 1M KHSO$_4$ solution. The mixture was extracted with EA. The org. phase was washed with water, dried (Na$_2$SO$_4$) and evaporated off to give the crude product as a colourless oil (1.5 g).

LC-MS: $t_R$=0.82 min; [M+H]$^+$: 282.11.

13.2. (S)-2-benzyloxycarbonylamino-5-iodo-pentanoic acid methyl ester

To a solution of intermediate 13.1 (1.4 g) in THF (40 mL) were added imidazole (545 mg) and PPh$_3$ (1.97 g). The mixture was cooled down to 0° C. and iodine (1.9 g) was added portion wise. After 10 min, the reaction mixture was allowed to warm to RT and was stirred at RT for 4 h. An aq. solution of Na$_2$S$_2$O$_3$ was added to the mixture that was further diluted with Et$_2$O. The phases were separated and the org. phase was washed with water, dried (MgSO$_4$) and evaporated off to afford the crude compound as a yellow oil (3.5 g).

LC-MS: $t_R$=1.04 min; [M+H]$^+$: 391.87.

13.3. (S)-2-benzyloxycarbonylamino-5-(diethoxy-phosphoryl)-pentanoic acid methyl ester This compound was prepared using a method analogous to that of Example 1, step 1.15, intermediate 13.2 replacing intermediate 1.14.

LC-MS: $t_R$=0.92 min; [M+H]$^+$: 402.02.

13.4. (S)-2-benzyloxycarbonylamino-5-(diethoxy-phosphoryl)-pentanoic acid

This compound was prepared using a method analogous to that of Example 1, step 1.16, intermediate 13.3 replacing intermediate 1.15.

LC-MS: $t_R$=0.80 min; [M+H]$^+$: 388.19.

13.5. 4-[(S)-2-benzyloxycarbonylamino-5-(diethoxy-phosphoryl)-pentanoyl]-piperazine-1-carboxylic acid butyl ester This compound was prepared using a method analogous to that of Example 1, step 1.17, intermediate 13.4 replacing intermediate 1.16 and intermediate 2.2 replacing 1-ethoxycarbonylpiperazine.

LC-MS: $t_R$=0.97 min; [M+H]$^+$: 555.98.

13.6. 4-[(S)-2-amino-5-(diethoxy-phosphoryl)-pentanoyl]-piperazine-1-carboxylic acid butyl ester This compound was prepared using a method analogous to that of Example 1 step 1.18, intermediate 13.5 replacing intermediate 1.17.

LC-MS: $t_R$=0.74 min; [M+H]$^+$: 422.12.

13.7. 4-((S)-5-(diethoxy-phosphoryl)-2-{[4-((S)-3-methoxy-pyrrolidin-1-yl)-6-phenyl-pyridine-2-carbonyl]-amino}-pentanoyl)-piperazine-1-carboxylic acid butyl ester This compound was prepared using a method analogous to that of Example 1, step 1.19, intermediate 13.6 replacing intermediate 1.18. The compound was purified by CC (EA/MeOH 10/1 to 9/1).

LC-MS: $t_R$=0.91 min; [M+H]$^+$: 702.13.

13.8. 4-((S)-2-{[4-((S)-3-methoxy-pyrrolidin-1-yl)-6-phenyl-pyridine-2-carbonyl]-amino}-5-phosphono-pentanoyl)-piperazine-1-carboxylic acid butyl ester This compound was prepared using a method analogous to that of Example 1, step 1.20, intermediate 13.7 replacing intermediate 1.19. The compound was purified by CC (reverse phase, water/MeCN 1/0 to 0/1) and then by preparative TLC (EA/MeOH 2/1).

LC-MS: $t_R$=0.80 min; [M+H]$^+$: 646.10.

Example 14

4-((R)-2-{[4-((S)-3-methoxy-pyrrolidin-1-yl)-6-phenyl-pyridine-2-carbonyl]-amino}-5-phosphono-pentanoyl)-piperazine-1-carboxylic acid butyl ester

14.1. (R)-2-benzyloxycarbonylamino-5-hydroxy-pentanoic acid methyl ester

This compound was prepared using a method analogous to that of Example 13, step 13.1, Cbz-D-Glu-OMe replacing Cbz-Glu-OMe.

LC-MS: $t_R$=0.82 min; [M+H]$^+$: 282.11.

14.2. (R)-2-benzyloxycarbonylamino-5-iodo-pentanoic acid methyl ester

This compound was prepared using a method analogous to that of Example 13, step 13.2, intermediate 14.1 replacing intermediate 13.1.

LC-MS: $t_R$=1.04 min; [M+H]$^+$: 391.84.

14.3. (R)-2-benzyloxycarbonylamino-5-(diethoxy-phosphoryl)-pentanoic acid methyl ester This compound was prepared using a method analogous to that of Example 1, step 1.15, intermediate 14.2 replacing intermediate 1.14.

LC-MS: $t_R$=0.92 min; [M+H]$^+$: 402.02.

14.4. (R)-2-benzyloxycarbonylamino-5-(diethoxy-phosphoryl)-pentanoic acid

This compound was prepared using a method analogous to that of Example 1, step 1.16, intermediate 14.3 replacing intermediate 1.15.

LC-MS: $t_R$=0.80 min; [M+H]$^+$: 388.09.

14.5. 4-[(R)-2-benzyloxycarbonylamino-5-(diethoxy-phosphoryl)-pentanoyl]-piperazine-1-carboxylic acid butyl ester This compound was prepared using a method analogous to that of Example 1, step 1.17, intermediate 14.4 replacing intermediate 1.16 and intermediate 2.2 replacing 1-ethoxycarbonylpiperazine. The compound was purified by CC (Hept/EA 2/8, then EA/MeOH 10/1).

LC-MS: $t_R$=0.98 min; [M+H]$^+$: 556.02.

14.6. 4-[(R)-2-amino-5-(diethoxy-phosphoryl)-pentanoyl]-piperazine-1-carboxylic acid butyl ester This compound was prepared using a method analogous to that of Example 1, step 1.18, intermediate 14.5 replacing intermediate 1.17.

LC-MS: $t_R$=0.74 min; [M+H]$^+$: 422.13.

14.7. 4-((R)-5-(diethoxy-phosphoryl)-2-{[4-((S)-3-methoxy-pyrrolidin-1-yl)-6-phenyl-pyridine-2-carbonyl]-amino}-pentanoyl)-piperazine-1-carboxylic acid butyl ester This compound was prepared using a method analogous to that of Example 1, step 1.19, intermediate 13.6 replacing intermediate 1.18. The compound was purified by CC (EA/MeOH 8/2, then EA/MeOH 9/1).

LC-MS: $t_R$=0.91 min; [M+H]$^+$: 702.42.

14.8. 4-((R)-2-{[4-((S)-3-methoxy-pyrrolidin-1-yl)-6-phenyl-pyridine-2-carbonyl]-amino}-5-phosphono-pentanoyl)-piperazine-1-carboxylic acid butyl ester This compound was prepared using a method analogous to that of Example 1, step 1.20, intermediate 14.7 replacing intermediate 1.19. The compound was purified by CC (reverse phase, water/MeCN 1/0 to 0/1) and then by preparative TLC (EA/MeOH 2/1).

LC-MS: $t_R$=0.80 min; [M+H]$^+$: 646.12.

Example 15

4-((R)-2-{[6-(2-fluoro-phenyl)-4-phenyl-pyridine-2-carbonyl]-amino}-3-phosphono-propionyl)-piperazine-1-carboxylic acid butyl ester

15.1. 4-[(R)-2-tert-butoxycarbonylamino-3-(diethoxy-phosphoryl)-propionyl]-piperazine-1-carboxylic acid butyl ester This compound was prepared using a method analogous to that of Example 1, step 1.17, intermediate 3.2 replacing intermediate 1.16 and intermediate 2.2 replacing 1-ethoxycarbonylpiperazine. The compound was however purified twice by CC (first CC: Hept/EA 88/12 to 0/100, followed by EA/MeOH 9/1, followed by EA/MeOH/NEt$_3$ 8/2/0.1; second CC: Hept/EA 1/1 to 0/1).

LC-MS: $t_R$=0.94 min; [M+H]$^+$: 494.54.

15.2. 4-[(R)-2-amino-3-(diethoxy-phosphoryl)-propionyl]-piperazine-1-carboxylic acid butyl ester This compound was prepared using a method analogous to that of Example 3, step 3.4, intermediate 15.1 replacing intermediate 3.3.

LC-MS: $t_R$=0.73 min; [M+H]$^+$: 394.37.

15.3. 4-phenyl-pyridine-2-carbonitrile

To a solution of 4-phenylpyridine N-oxide (5 g) in DCM (50 mL) was added at RT trimethylsilylcyanide (11 mL), followed by acetyl chloride (3.1 mL) over 10 min. The reaction mixture was stirred overnight at RT. A solution of aq. 10% Na$_2$CO$_3$ was added and the mixture was extracted with EA. The combined org. phases were washed with brine, dried (Na$_2$SO$_4$) and evaporated off. Filtration over a plug of silica gel (Hept/EA 1/1) gave the desired compound (450 mg).

LC-MS: $t_R$=0.97 min; [M+H]$^+$: 181.52.

15.4. 1-oxy-4-phenyl-pyridine-2-carbonitrile

MCPBA (766 mg) was added to a solution of intermediate 15.3 (400 mg) in DCM (10 mL) at RT. The reaction mixture was heated to 40-45° C. for 48 h. The reaction mixture was filtered off and the solid was washed with DCM. The solution was concentrated and Et$_2$O was added to the residue. The suspension thus obtained was filtered off and the white solid combined to the first batch to give the desired compound (410 mg).

LC-MS: $t_R$=0.83 min; [M+H]$^+$: 197.48.

15.5. 6-chloro-4-phenyl-pyridine-2-carbonitrile

To intermediate 15.4 (400 mg) was added, at RT, POCl$_3$ (5.3 ml) and the suspension stirred at reflux for 2 h. The reaction mixture was added carefully to an ice-cold NaOH solution. The resulting suspension was filtered off and the white solid washed with water and dried under HV to yield the desired product (350 mg).

LC-MS: $t_R$=1.06 min; [M+H+CH$_3$CN]$^+$: 257.30.

15.6. 6-chloro-4-phenyl-pyridine-2-carboxylic acid

Intermediate 15.5 (350 mg) in conc. HCl (37%, 12 mL) was heated to reflux for 2 h. The reaction mixture was added to ice-cold water (100 mL) and a conc. NaOH solution (32%, 10 mL). The aq. phase was extracted twice with EA. The combined org. phases were washed with conc. HCl and brine, dried (Na$_2$SO$_4$) and evaporated off to give the desired compound (330 mg).

LC-MS: $t_R$=0.90 min; [M+H]$^+$: 234.13.

15.7. 4-[(R)-2-[(6-chloro-4-phenyl-pyridine-2-carbonyl)-amino]-3-(diethoxy-phosphoryl)-propionyl]-piperazine-1-carboxylic acid butyl ester To an ice-cold solution of intermediate 15.6 (300 mg) in MeCN (6 mL) was added oxalyl chloride (0.109 mL). The mixture was allowed to warm to RT, cooled again down to 0° C. and NEt$_3$ (0.357 mL) was added slowly, followed by a solution of intermediate 15.2 (505 mg) in MeCN (4 mL). The mixture was allowed to warm to RT and was stirred at RT for 20 h. Intermediate 15.2 (150 mg) was added and the mixture was stirred for 2 h at RT. Intermediate 15.2 (150 mg) was again added and the mixture was stirred for 3 h at RT. EA and water were added to the mixture. The org. phase was washed with a Na$_2$CO$_3$ solution and with brine. The aq. phases were extracted with EA and the combined org. phases were dried (Na$_2$SO$_4$) and evaporated off to give the desired product as a brown oil (950 mg).

LC-MS: $t_R$=1.06 min; [M+H]$^+$: 609.04.

15.8. 4-((R)-3-(diethoxy-phosphoryl)-2-{[6-(2-fluoro-phenyl)-4-phenyl-pyridine-2-carbonyl]-amino}-propionyl)-piperazine-1-carboxylic acid butyl ester A mixture of intermediate 15.7 (100 mg), 2-fluorobenzeneboronic acid (30 mg), K$_3$PO$_4$ (70 mg) and Pd(PPh$_3$)$_4$ (9.5 mg) in dioxane (0.5 mL) was stirred at 110° C. under argon overnight. The solvent was evaporated off. The crude was purified by preparative TLC (DCM/acetone 5/3) to afford the desired compound as a colourless oil (35 mg).

LC-MS: $t_R$=1.12 min; [M+H]$^+$: 669.59.

15.9. 4-((R)-2-{[6-(2-fluoro-phenyl)-4-phenylpyridine-2-carbonyl]-amino}-3 phosphono-propionyl)-piperazine-1-carboxylic acid butyl ester This compound was prepared using a method analogous to that of Example 3, step 3.7, intermediate 15.8 replacing intermediate 3.6. The compound was however purified by preparative LC-MS (III).

LC-MS: $t_R$=0.98 min; [M+H]$^+$: 613.20.

Example 16

4-((R)-2-{[4-phenyl-6-(3-trifluoromethyl-phenyl)-pyridine-2-carbonyl]-amino}-3-phosphono-propionyl)-piperazine-1-carboxylic acid butyl ester

16.1. 4-((R)-3-(diethoxy-phosphoryl)-2-{[4-phenyl-6-(3-trifluoromethyl-phenyl)-pyridine-2-carbonyl]-amino}-propionyl)-piperazine-1-carboxylic acid butyl ester This compound was prepared using a method analogous to that of Example 15, step 15.8, 3-trifluoromethylphenylboronic acid replacing 2-fluorobenzeneboronic acid.

LC-MS: $t_R$=1.15 min; [M+H]$^+$: 719.72.

16.2. 4-((R)-2-{[4-phenyl-6-(3-trifluoromethyl-phenyl)-pyridine-2-carbonyl]-amino}-3-phosphono-propionyl)-piperazine-1-carboxylic acid butyl ester This compound was prepared using a method analogous to that of Example 15, step 15.9, intermediate 16.1 replacing intermediate 15.8.

LC-MS: $t_R$=1.02 min; [M+H]$^+$: 663.55.

Example 17

4-((R)-2-{[6-(4-fluoro-phenyl)-4-phenyl-pyridine-2-carbonyl]-amino}-3-phosphono-propionyl)-piperazine-1-carboxylic acid butyl ester

17.1. 4-((R)-3-(diethoxy-phosphoryl)-2-{[6-(4-fluoro-phenyl)-4-phenyl-pyridine-2-carbonyl]-amino}-propionyl)-piperazine-1-carboxylic acid butyl ester This compound was prepared using a method analogous to that of Example 15, step 15.8, 4-fluorobenzeneboronic acid replacing 2-fluorobenzeneboronic acid.

LC-MS: $t_R$=1.12 min; [M+H]$^+$: 669.97.

17.2. 4-((R)-2-{[6-(4-fluoro-phenyl)-4-phenylpyridine-2-carbonyl]-amino}-3 phosphono-propionyl)-piperazine-1-carboxylic acid butyl ester This compound was prepared using a method analogous to that of Example 15 step 15.9, intermediate 17.1 replacing intermediate 15.8.

LC-MS: $t_R$=0.98 min; [M+H]$^+$: 613.67.

Example 18

4-{(R)-2-[(4-phenyl-6-p-tolyl-pyridine-2-carbonyl)-amino]-3-phosphono-propionyl}-piperazine-1-carboxylic acid butyl ester

18.1. 4-{(R)-3-(diethoxy-phosphoryl)-2-[(4-phenyl-6-p-tolyl-pyridine-2-carbonyl)-amino]-propionyl}-piperazine-1-carboxylic acid butyl ester This compound was prepared using a method analogous to that of Example 15, step 15.8, 4-tolylboronic acid replacing 2-fluorobenzeneboronic acid.

LC-MS: $t_R$=1.13 min; [M+H]$^+$: 665.73.

18.2. 4-{(R)-2-[(4-phenyl-6-p-tolyl-pyridine-2-carbonyl)-amino]-3-phosphono-propionyl}-piperazine-1-carboxylic acid butyl ester This compound was prepared using a method analogous to that of Example 15, step 15.9, intermediate 18.1 replacing intermediate 15.8.

LC-MS: $t_R$=1.00 min; [M+H]$^+$: 609.18.

Example 19

4-((R)-2-{[4-((1S,2S)-2-methoxymethyl-cyclopropyl)-6-phenyl-pyridine-2-carbonyl]-amino}-3-phosphono-propionyl)-piperazine-1-carboxylic acid butyl ester

19.1. (E)-3-tributylstannanyl-prop-2-en-1-ol

To neat propargyl alcohol (1.77 mL) were added tributyltin hydride (10.3 mL) followed by 1,1'-azobis(cyclohexanecarbonitrile) (378 mg). The mixture was heated for 2.5 h at 80° C., cooled to RT and directly purified by CC (EA/Hept 5/95) to afford the desired compound (5.4 g).

$^1$H-NMR (CDCl$_3$): 6.22 (m, 2H); 4.20 (m, 2H); 1.57-1.28 (m, 18H); 0.92 (t, 9H).

19.2. ((1R,2S)-2-tributylstannanyl-cyclopropyl)-methanol

To a solution of dimethoxyethane (1.8 mL) in anhydrous DCM (70 mL) cooled at −13° C. under argon was slowly added diethylzinc (18.5 mL), followed by diiodomethane (3 mL) in DCM (20 mL) over a 30 min period while keeping the internal temperature around −12.5° C. After completion of the addition, the resulting solution was stirred for 30 min at −10° C. A solution of (4R,5R)-2-butyl-N,N,N',N'-tetramethyl-1,3,2-dioxaborolane-4,5-dicarboxamide in DCM (25 mL) was added slowly to keep internal temperature below −10° C., immediately followed by a solution of intermediate 19.1 (3.2 g) in DCM (25 mL) dropwise (internal temperature between −10° C. and −8° C.). The cooling bath was removed, and the reaction mixture was allowed to warm to RT and was stirred overnight at RT. The reaction was quenched with an aq. NH$_4$Cl solution (10 mL), and a 1M aq. HCl solution (10 mL). The mixture was diluted with H$_2$O, the org. phase separated and the aq. phase was extracted with DCM and Et$_2$O. The combined org. phases were dried over MgSO$_4$ and evaporated off. CC (Hept/EA 100/0 to 95:5) gave 3.18 g of the desired compound.

$^1$H-NMR (CDCl$_3$): 3.55 (m, 1H); 3.39 (m, 1H); 1.54-1.44 (m, 6H); 1.36-1.24 (m, 6H); 1.14-1.03 (m, 1H); 0.90 (t, 9H); 0.83-0.78 (m, 6H); 0.75-0.69 (m, 1H); 0.55-0.50 (m, 2H); −0.20-−0.30 (m, 1H).

Optical rotation (589 nm, CHCl$_3$, 26.6° C., l=10 cm, 99.6 mg in 10 mL, c=1.0): specific optical rotation=+14.74.

19.3. Tributyl-((1S,2R)-2-methoxymethyl-cyclopropyl)-stannane

To a solution of intermediate 19.2 (9.5 g) in THF (200 mL) was added NaH (2.27 g, 60% in mineral oil) at RT, and the mixture stirred 30 min at RT. MeI (7.55 mL) was added and stirring was continued at RT overnight. The reaction mixture was diluted with H$_2$O and extracted with DCM. The combined org. phases were dried over MgSO$_4$ and evaporated off to afford the desired compound as a pale yellow oil (10.49 g).

$^1$H-NMR (CDCl$_3$): 3.45 (dd, 1H); 3.38 (s, 3H); 3.12 (dd, 1H); 1.55-1.47 (m, 6H); 1.37-1.28 (m, 6H); 1.05 (m, 1H); 0.91 (t, 9H); 0.83 (m, 6H); 0.56 (m, 2H); −0.30 (m, 1H).

19.4. 4-[(R)-2-[(4-chloro-6-phenyl-pyridine-2-carbonyl)-amino]-3-(diethoxy-phosphoryl)-propionyl]-piperazine-1-carboxylic acid butyl ester This compound was prepared using a method analogous to that of Example 1, step 1.17, intermediate 1.9 replacing intermediate 1.16 and intermediate 15.2 replacing 1-ethoxycarbonylpiperazine. The compound was however purified by CC (Hept/EA 1/1 to 0/1).

LC-MS: t$_R$=1.07 min; [M+H]$^+$: 609.29.

19.5. 4-((R)-3-(diethoxy-phosphoryl)-2-{[4-((1S,2S)-2-methoxymethyl-cyclopropyl)-6-phenyl-pyridine-2-carbonyl]-amino}-propionyl)-piperazine-1-carboxylic acid butyl ester A solution of intermediate 19.3 (90 mg), intermediate 19.4 (95 mg) and Pd(PPh$_3$)$_4$ (10 mg) in toluene (1.5 mL) was degassed and heated at 130° C. for 16 h under argon. The same quantities of intermediate 19.3 and Pd(PPh$_3$)$_4$ were added and the mixture was further heated at 130° C. for 20 h. Water and EA were added and the phases were separated. The org. phase was dried (Na$_2$SO$_4$) and evaporated off. The crude was purified by CC (EA/MeOH 1/0 to 1/1) to afford the desired compound as a yellow oil (45 mg).

LC-MS: t$_R$=1.05 min; [M+H]$^+$: 659.75.

19.6. 4-((R)-2-{[4-((1S,2S)-2-methoxymethyl-cyclopropyl)-6-phenyl-pyridine-2-carbonyl]-amino}-3-phosphono-propionyl)-piperazine-1-carboxylic acid butyl ester This compound was prepared using a method analogous to that of Example 3, step 3.7, intermediate 19.5 replacing intermediate 3.6.

LC-MS: t$_R$=0.90 min; [M+H]$^+$: 603.71.

Example 20

4-((R)-2-{[4-((1S,2S)-2-hydroxymethyl-cyclopropyl)-6-phenyl-pyridine-2-carbonyl]-amino}-3-phosphono-propionyl)-piperazine-1-carboxylic acid butyl ester

20.1. 4-((R)-3-(diethoxy-phosphoryl)-2-{[4-((1S,2S)-2-hydroxymethyl-cyclopropyl)-6-phenyl-pyridine-2-carbonyl]-amino}-propionyl)-piperazine-1-carboxylic acid butyl ester This compound was prepared using a method analogous to that of Example 19, step 19.5, intermediate 19.2 replacing intermediate 19.3. The compound was however purified by CC (Hept/EA 1/1 to 0/1, then EA/MeOH 1/1).

LC-MS: t$_R$=0.97 min; [M+H]$^+$: 645.57.

20.2. 4-((R)-2-{[4-((1S,2S)-2-hydroxymethyl-cyclopropyl)-6-phenyl-pyridine-2-carbonyl]-amino}-3-phosphono-propionyl)-piperazine-1-carboxylic acid butyl ester This compound was prepared using a method analogous to that of Example 3, step 3.7, intermediate 20.1 replacing intermediate 3.6.

LC-MS: t$_R$=0.84 min; [M+H]$^+$: 589.61.

Example 21

4-((R)-2-{[4-((S)-3-methoxy-pyrrolidin-1-yl)-6-phenyl-pyridine-2-carbonyl]-amino}-3-phosphono-propionyl)-piperazine-1-carboxylic acid ethyl ester

21.1. 4-((R)-3-(diethoxy-phosphoryl)-2-{[4-((S)-3-methoxy-pyrrolidin-1-yl)-6-phenyl-pyridine-2-carbonyl]-amino}-propionyl)-piperazine-1-carboxylic acid ethyl ester This compound was prepared using a method analogous to that of Example 1, step 1.17, intermediate 1.10 replacing intermediate 1.16 and intermediate 3.4 replacing 1-ethoxy-carbonylpiperazine.

LC-MS: $t_R$=0.84 min; [M+H]$^+$: 647.05.

21.2. 4-((R)-2-{[4-((S)-3-methoxy-pyrrolidin-1-yl)-6-phenyl-pyridine-2-carbonyl]-amino}-3-phosphono-propionyl)-piperazine-1-carboxylic acid ethyl ester This compound was prepared using a method analogous to that of Example 1, step 1.20, intermediate 21.1 replacing intermediate 1.19. However no work-up was performed, the reaction mixture was evaporated off and the residue was purified by preparative LC-MS (IV) followed by preparative LC-MS (V).

LC-MS: $t_R$=0.72 min; [M+H]$^+$: 590.44.

Example 22

4-((R)-2-{[4-((S)-3-methoxy-pyrrolidin-1-yl)-6-phenyl-pyridine-2-carbonyl]-amino}-3-phosphono-propionyl)-piperazine-1-carboxylic acid butyl ester

22.1. 4-((R)-3-(diethoxy-phosphoryl)-2-{[4-((S)-3-methoxy-pyrrolidin-1-yl)-6-phenyl-pyridine-2-carbonyl]-amino}-propionyl)-piperazine-1-carboxylic acid butyl ester This compound was prepared using a method analogous to that of Example 1, step 1.17, intermediate 1.10 replacing intermediate 1.16 and intermediate 15.2 replacing 1-ethoxy-carbonylpiperazine. The compound was purified by CC (EA/MeOH 1/0 to 9/1).

LC-MS: $t_R$=0.90 min; [M+H]$^+$: 674.72.

22.2. 4-((R)-2-{[4-((S)-3-methoxy-pyrrolidin-1-yl)-6-phenyl-pyridine-2-carbonyl]-amino}-3-phosphono-propionyl)-piperazine-1-carboxylic acid butyl ester This compound was prepared using a method analogous to that of Example 1, step 1.20, intermediate 22.1 replacing intermediate 1.19. The compound was purified by CC (reverse phase, water/MeCN 95/5 to 10/90).

LC-MS: $t_R$=0.78 min; [M+H]$^+$: 618.22.

Example 23

4-((S)-2-{[4-((S)-3-methoxy-pyrrolidin-1-yl)-6-phenyl-pyridine-2-carbonyl]-amino}-3-phosphono-propionyl)-piperazine-1-carboxylic acid ethyl ester

23.1. (S)-2-tert-butoxycarbonylamino-3-(diethoxy phosphoryl)propionic acid methyl ester This compound was prepared using a method analogous to that of Example 3, step 3.1, Boc-3-iodo-D-Ala-OMe replacing Boc-3-iodo-L-Ala-OMe.

$^1$H-NMR (CDCl$_3$): 6.12 (br. s, 1H); 5.71 (br. s, 1H); 4.11 (m, 4H); 3.77 (s, 3H); 2.33 (m, 2H); 1.41 (s, 9H); 1.33 (m, 6H).

23.2. (S)-2-tert-butoxycarbonylamino-3-(diethoxy phosphoryl)propionic acid

This compound was prepared using a method analogous to that of Example 1, step 1.16, intermediate 23.1 replacing intermediate 1.15.

LC-MS: $t_R$=0.77 min; [M+H]$^+$: 326.29.

23.3. 4-[(S)-2-tert-butoxycarbonylamino-3-(di-ethoxy-phosphoryl)-propionyl]-piperazine-1-carboxylic acid ethyl ester This compound was prepared using a method analogous to that of Example 1, step 1.17, intermediate 23.2 replacing intermediate 1.16.

LC-MS: $t_R$=0.85 min; [M+H]$^+$: 466.21.

23.4. 4-[(S)-2-amino-3-(diethoxy-phosphoryl)-propionyl]-piperazine-1-carboxylic acid ethyl ester hydrochloride salt This compound was prepared using a method analogous to that of Example 2, step 2.2, intermediate 23.3 replacing intermediate 2.1 and EA replacing MeOH.

LC-MS: $t_R$=0.66 min; [M+H]$^+$: 366.12.

23.5. 4-((S)-3-(diethoxy-phosphoryl)-2-{[4-((S)-3-methoxy-pyrrolidin-1-yl)-6-phenyl-pyridine-2-carbonyl]-amino}-propionyl)-piperazine-1-carboxylic acid ethyl ester This compound was prepared using a method analogous to that of Example 12, step 12.2, intermediate 1.10 replacing intermediate 12.1 and intermediate 23.4 replacing intermediate 2.2. The compound was purified by CC (EA/Hept/MeOH 1/1/0 to 9/0/1).

LC-MS: $t_R$=0.84 min; [M+H]$^+$: 646.85.

23.6. 4-((S)-2-{[4-((S)-3-methoxy-pyrrolidin-1-yl)-6-phenyl-pyridine-2-carbonyl]-amino}-3-phosphono-propionyl)-piperazine-1-carboxylic acid ethyl ester This compound was prepared using a method analogous to that of Example 1, step 1.20, intermediate 23.5 replacing intermediate 1.19. The compound was purified by CC (reverse phase, water/MeCN 95/5 to 50/50).

LC-MS: $t_R$=0.71 min; [M+H]$^+$: 590.23.

Example 24

4-[(S)-2-{[4-((S)-3-methoxy-pyrrolidin-1-yl)-6-phenyl-pyridine-2-carbonyl]-amino}-3-(4-phosphono-phenyl)-propionyl]-piperazine-1-carboxylic acid ethyl ester

24.1. (S)-2-tert-butoxycarbonylamino-3-(4-iodo-phenyl)-propionic acid ethyl ester To a solution of (S)-2-tert-butoxycarbonylamino-3-(4-iodo-phenyl)-propionic acid (3 g) in anh. EtOH (38 mL) was added DMAP (187 mg) and PyBOP (6 g). The reaction mixture was stirred on at RT and partitioned between EA and water. The org. phase was separated, washed with 10% aq. citric acid and sat. aq. NaHCO$_3$, dried (Na$_2$SO$_4$) and evaporated off. The resulting crude material was purified by CC (Hept/EA 1/0 to 0/1) to afford the title compound as a white solid (3 g).
LC-MS: $t_R$=1.10 min; [M+H]$^+$: 419.78.

24.2. (S)-2-tert-butoxycarbonylamino-3-[4-(diethoxy phosphoryl)phenyl]-propionic acid ethyl ester To a solution of intermediate 24.1 (3 g) in MeCN (128 mL) was added tetrakis(triphenylphosphine)palladium (0) (254 mg), diethyl phosphite (1.4 mL) and NEt$_3$ (2 mL). The mixture was stirred on at 70° C., an additional amount of tetrakis (triphenylphosphine)palladium (0) (846 mg) was added and the mixture refluxed on. MeCN was evaporated off and the residue taken up in EA. The org. phase was washed with 10% aq. citric acid, sat. aq. NaHCO$_3$ and brine, dried (Na$_2$SO$_4$) and evaporated off. The crude material was purified twice by CC (Hept/EA 9/1 to 0/1; then DCM/MeOH 1/0 to 20/1) to afford the title compound as a colourless resin (2.79 g).
LC-MS: $t_R$=0.98 min; [M+H]$^+$: 430.05.

24.3. (S)-2-tert-butoxycarbonylamino-3-[4-(diethoxy-phosphoryl)-phenyl]-propionic acid This compound was prepared using a method analogous to that of Example 1, step 1.16, intermediate 24.2 replacing intermediate 1.15.
LC-MS: $t_R$=0.86 min; [M+H]$^+$: 402.01.

24.4. 4-{(S)-2-tert-butoxycarbonylamino-3-[4-(diethoxy-phosphoryl)-phenyl]-propionyl}-piperazine-1-carboxylic acid ethyl ester This compound was prepared using a method analogous to that of Example 12, step 12.2, intermediate 24.3 replacing intermediate 12.1 and 1-ethoxycarbonylpiperazine replacing intermediate 2.2. The compound was purified by CC (EA/MeOH 1/0 to 40/1).
LC-MS: $t_R$=0.93 min; [M+H]$^+$: 542.01.

24.5. 4-{(S)-2-amino-3-[4-(diethoxy-phosphoryl)-phenyl]-propionyl}-piperazine-1-carboxylic acid ethyl ester hydrochloride salt This compound was prepared using a method analogous to that of Example 2, step 2.2, intermediate 24.4 replacing intermediate 2.1 and EA replacing MeOH.
LC-MS: $t_R$=0.69 min; [M+H]$^+$: 442.11.

24.6. 4-((S)-3-[4-(diethoxy-phosphoryl)-phenyl]-2-{[4-((S)-3-methoxy-pyrrolidin-1-yl)-6-phenyl-pyridine-2-carbonyl]-amino}-propionyl)-piperazine-1-carboxylic acid ethyl ester This compound was prepared using a method analogous to that of Example 12, step 12.2, intermediate 1.10 replacing intermediate 12.1 and intermediate 24.5 replacing intermediate 2.2. The compound was purified by CC (EA/MeOH 1/0 to 98/2).
LC-MS: $t_R$=0.89 min; [M+H]$^+$: 722.87.

24.7. 4-[(S)-2-{[4-((S)-3-methoxy-pyrrolidin-1-yl)-6-phenyl-pyridine-2-carbonyl]-amino}-3-(4-phosphono-phenyl)-propionyl]-piperazine-1-carboxylic acid ethyl ester This compound was prepared using a method analogous to that of Example 1, step 1.20, intermediate 24.6 replacing intermediate 1.19. The crude was purified by CC (reverse phase, water/MeCN 95/5 to 20/80).
LC-MS: $t_R$=0.75 min; [M+H]$^+$: 666.03.

Example 25

4-[(R)-2-[(4-isopropyl-6-phenyl-pyridine-2-carbonyl)-amino]-3-phosphono-propionyl]-piperazine-1-carboxylic acid butyl ester 25.1. 4-[(R)-2-[(4-chloro-6-phenyl-pyridine-2-carbonyl)-amino]-3-(diethoxy-phosphoryl)-propionyl]-piperazine-1-carboxylic acid butyl ester This compound was prepared using a method analogous to that of Example 1, step 1.17, intermediate 1.9 replacing intermediate 1.16 and intermediate 15.2 replacing 1-ethoxycarbonylpiperazine. The compound was purified by CC (EA/Hept 1/1 to 1/0).
LC-MS: $t_R$=1.07 min; [M+H]$^+$: 609.71.

25.2. 4-{(R)-3-(diethoxy-phosphoryl)-2-[(4-isopropyl-6-phenyl-pyridine-2-carbonyl)-amino]-propionyl}-piperazine-1-carboxylic acid butyl ester To a solution of intermediate 25.1 (26 mg) in THF (0.4 mL) was added at RT, iron(III) acetylacetonate (0.8 mg) and a 1M solution of isopropylmagnesium bromide in THF (0.13 mL). The mixture was stirred for 2 h at RT and an additional amount of a 1M solution of isopropylmagnesium bromide in THF (0.21 mL) was added at RT. The mixture was further stirred for 15 min, quenched with a 1M solution of aq. HCl and extracted twice with EA. The org. phase was dried (Na$_2$SO$_4$), evaporated off and the crude material was purified by CC (EA/MeOH 1/0 to 25/1) to afford the title compound as a yellowish resin (14 mg).
LC-MS: $t_R$=1.09 min; [M+H]$^+$: 617.63.

25.3. 4-{(R)-2-[(4-isopropyl-6-phenyl-pyridine-2-carbonyl)-amino]-3-phosphono-propionyl}-piperazine-1-carboxylic acid butyl ester This compound was prepared using a method analogous to that of Example 1, step 1.20, intermediate 25.2 replacing intermediate 1.19. The crude was purified by CC (reverse phase, water/MeCN 95/5 to 20/80).
LC-MS: $t_R$=0.94 min; [M+H]$^+$: 561.54.

Example 26

4-[(R)-2-[(4-methoxy-6-phenyl-pyridine-2-carbonyl)-amino]-3-phosphono-propionyl]-piperazine-1-carboxylic acid butyl ester 26.1. 4-methoxy-6-phenyl-pyridine-2-carboxylic acid To a solution of intermediate 1.9 (1 g) in anh. DMF (5 mL) and anh. MeOH (3 mL) was added dropwise at RT a 5.4 M solution of sodium methoxide in MeOH (3.2 mL). The resulting suspension was stirred on at 100° C., cooled down and concentrated in vacuo. The residue was treated with water, the insoluble material was filtered off and dried in HV to give of the crude product as a beige solid (1 g).
LC-MS: $t_R$=0.68 min; [M+H]$^+$: 230.37.

26.2. 4-{(R)-3-(diethoxy-phosphoryl)-2-[(4-methoxy-6-phenyl-pyridine-2-carbonyl)-amino]-propionyl}-piperazine-1-carboxylic acid butyl ester This compound was prepared using a method analogous to that of Example 12, step 12.2, intermediate 26.1 replacing intermediate 12.1 and intermediate 15.2 replacing intermediate 2.2. The compound was purified by CC (EA/MeOH 1/0 to 100/1).
LC-MS: $t_R$=1.04 min; [M+H]$^+$: 605.60.

26.3. 4-{(R)-2-[(4-methoxy-6-phenyl-pyridine-2-carbonyl)-amino]-3-phosphono-propionyl}-piperazine-1-carboxylic acid butyl ester This compound was prepared using a method analogous to that of Example 1, step 1.20, intermediate 26.2 replacing intermediate 1.19. The crude was purified by CC (reverse phase, water/MeCN 95/5 to 20/80).
LC-MS: $t_R$=0.88 min; [M+H]$^+$: 549.57.

Example 27

4-[(R)-2-[(6-phenyl-4-pyrrolidin-1-yl-pyridine-2-carbonyl)-amino]-3-phosphono-propionyl]-piperazine-1-carboxylic acid butyl ester 27.1. 4-{3-(ethoxy-hydroxy-phosphoryl)-2-[(6-phenyl-4-pyrrolidin-1-yl-pyridine-2-carbonyl)-amino]-propionyl}-piperazine-1-carboxylic acid butyl ester A solution of intermediate 25.1 (58 mg) and pyrrolidine (68 µL) in THF (0.5 mL) was heated in a microwave oven at 120° C. for 1 h. The solvent was evaporated and replaced by NMP (0.5 mL) and further 10 eq. of pyrrolidine were added. The mixture was heated at 120° C. for 1 h and directly purified by preparative LC-MS (I) to give a yellow oil (47 mg) consisting of a mixture of the desired compound and some corresponding diethyl phosphonate.
LC-MS: $t_R$=0.82 min; [M+H]$^+$: 616.50.

27.2. 4-{(R)-2-[(6-phenyl-4-pyrrolidin-1-yl-pyridine-2-carbonyl)-amino]-3-phosphono-propionyl}-piperazine-1-carboxylic acid butyl ester This compound was prepared using a method analogous to that of Example 1, step 1.20, intermediate 27.1 replacing intermediate 1.19. The compound was however purified by preparative LC-MS (IV).
LC-MS: $t_R$=0.79 min; [M+H]$^+$: 588.28.

Example 28

4-{(R)-2-[2-(4-butoxycarbonyl-piperazin-1-yl)-2-oxo-1-phosphonomethyl-ethylcarbamoyl]-6-phenyl-pyridin-4-yl}-1-methyl-piperazin-1-ium formate 28.1. 4-(3-(ethoxy-hydroxy-phosphoryl)-2-{[4-(4-methyl-piperazin-1-yl)-6-phenyl-pyridine-2-carbonyl]-amino}-propionyl)-piperazine-1-carboxylic acid butyl ester This compound was prepared using a method analogous to that of Example 27, step 27.1, 1-methylpiperazine replacing pyrrolidine. The compound was however purified by preparative LC-MS (IV).
LC-MS: $t_R$=0.72 min; [M+H]$^+$: 645.17.

28.2. 4-{(R)-2-[2-(4-butoxycarbonyl-piperazin-1-yl)-2-oxo-1-phosphonomethyl-ethylcarbamoyl]-6-phenyl-pyridin-4-yl}-1-methyl-piperazin-1-ium formate This compound was prepared using a method analogous to that of Example 1, step 1.20, intermediate 28.1 replacing intermediate 1.19. The compound was however purified by preparative LC-MS (IV).
LC-MS: $t_R$=0.70 min; [M+H]$^+$: 617.31.

Example 29

4-((R)-2-{[6-phenyl-(R)-4-(tetrahydro-furan-3-ylamino)-pyridine-2-carbonyl]-amino}-3-phosphono-propionyl)-piperazine-1-carboxylic acid butyl ester 29.1. 4-{3-(ethoxy-hydroxy-phosphoryl)-2-[(6-phenyl-4-pyrrolidin-1-yl-pyridine-2-carbonyl)-amino]-propionyl}-piperazine-1-carboxylic acid butyl ester A reaction mixture containing intermediate 25.1 (100 mg), (R)-(+)-3-aminotetrahydrofurane toluene-4-sulfonate (43 mg), acetato (2'-di-tert-butylphosphino-1,1'-biphenyl-2-yl) palladium (9.7 mg) and NaOtBu (46 mg) in toluene (1 mL) at 90° C. under argon until reaction completion. The solvent was evaporated in vacuo and the crude product (119 mg) used without further purification.
LC-MS: $t_R$=0.78 min; [M+H]$^+$: 632.16.

29.2. 4-((R)-2-{[6-phenyl-(R)-4-(tetrahydro-furan-3-ylamino)-pyridine-2-carbonyl]-amino}-3-phosphono-propionyl)-piperazine-1-carboxylic acid butyl ester This compound was prepared using a method analogous to that of Example 1, step 1.20, intermediate 27.1 replacing intermediate 1.19 and 10 eq. of TMSBr being added after 1 h, the reaction mixture being further stirred for 1 h. The compound was however purified by preparative LC-MS (IV).
LC-MS: $t_R$=0.71 min; [M+H]$^+$: 604.14.

Example 30

4-[(R)-2-[(2-hydroxymethyl-6'-phenyl-3,4,5,6-tetrahydro-2H-[1,4']bipyridinyl-2'-carbonyl)-amino]-3-phosphono-propionyl]-piperazine-1-carboxylic acid butyl ester A reaction mixture containing intermediate 25.1 (100 mg), 2-hydroxymethyl-piperidine (382 mg), acetato (2'-di-tert-butylphosphino-1,1'-biphenyl-2-yl)palladium (1.5 mg) and NaOtBu (46 mg) in toluene (1 mL) was heated at 90° C. under argon for 3 h. The solvent was evaporated in vacuo and the residue filtrated over RP-18 (ca. 5 g) to remove the amine. The crude product was directly engaged in the next step using a method analogous to that of Example 1, step 1.20, the crude product replacing intermediate 1.19. The compound was however purified by preparative LC-MS (IV) to give a yellow solid (6 mg).
LC-MS: $t_R$=0.77 min; [M+H]$^+$: 632.59.

Example 31

4-{(R)-2-[(4-cyclopropylamino-6-phenyl-pyridine-2-carbonyl)-amino]-3-phosphono-propionyl}-piperazine-1-carboxylic acid butyl ester This compound was prepared using a method analogous to that of Example 30, cyclopropylamine replacing 2-hydroxymethyl-piperidine. The compound was however purified by preparative LC-MS (IV).
LC-MS: $t_R$=0.78 min; [M+H]$^+$: 574.38.

Example 32

4-{(R)-2-[(6-phenyl-4-phenylamino-pyridine-2-carbonyl)-amino]-3-phosphono-propionyl}-piperazine-1-carboxylic acid butyl ester This compound was prepared using a method analogous to that of Example 30, aniline replacing 2-hydroxymethyl-piperidine. The compound was however purified by preparative LC-MS (IV).
LC-MS: $t_R$=0.81 min; [M+H]$^+$: 610.14.

Example 33

4-[(R)-2-[(6-phenyl-4-propylamino-pyridine-2-carbonyl)-amino]-3-phosphono-propionyl]-piperazine-1-carboxylic acid butyl ester This compound was prepared using a method analogous to that of Example 30, propylamine replacing 2-hydroxymethyl-piperidine. The compound was however purified by preparative LC-MS (IV).
LC-MS: $t_R$=0.75 min; [M+H]$^+$: 576.16.

Example 34

4-((R)-2-{[4-(2-carboxy-ethylamino)-6-phenyl-pyridine-2-carbonyl]-amino}-3-phosphono-propionyl)-piperazine-1-carboxylic acid butyl ester This compound was prepared using a method analogous to that of Example 30, β-alanine ethylester hydrochloride replacing 2-hydroxymethyl-piperidine. The compound was however purified by preparative LC-MS (IV).
LC-MS: $t_R$=0.74 min; [M+H]$^+$: 606.27.

Example 35

4-((R)-2-{[4-((S)-3-methoxy-pyrrolidin-1-yl)-6-phenyl-pyridine-2-carbonyl]-amino}-3-phosphono-propionyl)-3-methyl-piperazine-1-carboxylic acid ethyl ester

35.1. 3-methyl-piperazine-1-carboxylic acid ethyl ester

To a solution of 2-methylpiperazine (10.0 g) in MeOH (120 mL), H$_2$O (40 mL) and AcOH was added at −5° C. dropwise during 25 min ethyl chloroformate (10 mL) and the reaction mixture was stirred overnight at RT. Then, H$_2$O (100 mL) was added and the MeOH evaporated in vacuo. The aq. phase was diluted with toluene (70 mL), the layers were separated and the org. layer was washed with water (50 mL). The aq. phase was then basified with NaOH (2M, 80 mL) and extracted with toluene (100 mL). The combined org. phases were washed with brine (50 mL), dried over MgSO$_4$ and evaporated in vacuo to give the desired compound (8.5 g).
LC-MS: $t_R$=0.34 min; [M+H+CH$_3$CN]$^+$: 214.40.

35.2. 4-[(R)-2-tert-butoxycarbonylamino-3-(diethoxy-phosphoryl)-propionyl]-3-methyl-piperazine-1-carboxylic acid ethyl ester This compound was prepared using a method analogous to that of Example 1, step 1.17, intermediate 35.1 replacing 1-ethoxycarbonylpiperazine and intermediate 3.2 replacing intermediate 1.16.
LC-MS: $t_R$=0.88 min; [M+H]$^+$: 479.66.

35.3. 4-[(R)-2-amino-3-(diethoxy-phosphoryl)-propionyl]-3-methyl-piperazine-1-carboxylic acid ethyl ester This compound was prepared using a method analogous to that of Example 3, step 3.4, intermediate 35.2 replacing intermediate 3.3.
LC-MS: $t_R$=0.67 min; [M+H]$^+$: 380.38.

35.4. 4-((R)-3-(diethoxy-phosphoryl)-2-{[4-((S)-3-methoxy-pyrrolidin-1-yl)-6-phenyl-pyridine-2-carbonyl]-amino}-propionyl)-3-methyl-piperazine-1-carboxylic acid ethyl ester This compound was prepared using a method analogous to that of Example 1, step 1.17, intermediate 35.3 replacing 1-ethoxycarbonylpiperazine and intermediate 1.10 replacing intermediate 1.16. The compound was however purified by CC (EA/Hept 1/1 to 1/0, followed by DCM/MeOH 97/3 to 95/5).
LC-MS: $t_R$=0.86 min; [M+H]$^+$: 660.16.

35.5. 4-((R)-2-{[4-((S)-3-methoxy-pyrrolidin-1-yl)-6-phenyl-pyridine-2-carbonyl]-amino}-3-phosphono-propionyl)-3-methyl-piperazine-1-carboxylic acid ethyl ester This compound was prepared using a method analogous to that of Example 1, step 1.20, intermediate 35.4 replacing intermediate 1.19. The compound was however purified by preparative LC-MS (IV).
LC-MS: $t_R$=0.73; [M+H]$^+$: 604.30.

Example 36

4-((R)-2-{[4-(2-methoxy-ethoxy)-6-phenyl-pyridine-2-carbonyl]-amino}-3-phosphono-propionyl)-piperazine-1-carboxylic acid butyl ester

36.1. 4-(2-methoxy-ethoxy)-6-phenyl-pyridine-2-carboxylic acid

To a suspension of sodium (35 mg) in anh. THF (3 mL) was added 2-methoxy-ethanol (0.24 mL). The suspension was stirred at RT for 30 min then at 50° C. until complete disappearance of the sodium pieces. To this solution of alkoxide was added dropwise a solution of intermediate 1.9 (200 mg) in anh. THF (0.8 mL) and the resulting suspension was stirred on under reflux. An additional solution of alkoxide was prepared as described above (sodium (35 mg), 2-methoxy-ethanol (0.24 mL) and anh. THF (3 mL)) and added to the reaction mixture. The suspension was further stirred on under reflux and concentrated in vacuo. The residue was taken up in water and the aq. solution acidified to pH 2 with 25% HCl and extracted with DCM. The org. phase was dried (Na$_2$SO$_4$) and evaporated off to afford a yellow oil (204 mg).

LC-MS: $t_R$=0.71 min; [M+H]$^+$: 274.26.

36.2. 4-((R)-3-(diethoxy-phosphoryl)-2-{[4-(2-methoxy-ethoxy)-6-phenyl-pyridine-2-carbonyl]-amino}-propionyl)-piperazine-1-carboxylic acid butyl ester This compound was prepared using a method analogous to that of Example 12, step 12.2, intermediate 36.1 replacing intermediate 12.1 and intermediate 15.2 replacing intermediate 2.2. The compound was purified by CC (EA/MeOH 1/0 to 25/1).

LC-MS: $t_R$=1.03 min; [M+H]$^+$: 649.77.

36.3. 4-((R)-2-{[4-(2-methoxy-ethoxy)-6-phenyl-pyridine-2-carbonyl]-amino}-3-phosphono-propionyl)-piperazine-1-carboxylic acid butyl ester This compound was prepared using a method analogous to that of Example 1, step 1.20, intermediate 36.2 replacing intermediate 1.19. The crude was purified by CC (reverse phase, water/MeCN 95/5 to 20/80).

LC-MS: $t_R$=0.88 min; [M+H]$^+$: 593.46.

Example 37

4-[(R)-2-[(4-methyl-6-phenyl-pyridine-2-carbonyl)-amino]-3-phosphono-propionyl]-piperazine-1-carboxylic acid butyl ester

37.1. 4-{(R)-3-(diethoxy-phosphoryl)-2-[(4-methyl-6-phenyl-pyridine-2-carbonyl)-amino]-propionyl}-piperazine-1-carboxylic acid butyl ester This compound was prepared using a method analogous to that of Example 25, step 25.2, a 1M solution of methylmagnesium bromide in THF replacing the 1M solution of isopropylmagnesium bromide in THF.

LC-MS: $t_R$=1.04; [M+H]$^+$: 589.98.

37.2. 4-{(R)-2-[(4-methyl-6-phenyl-pyridine-2-carbonyl)-amino]-3-phosphono-propionyl}-piperazine-1-carboxylic acid butyl ester This compound was prepared using a method analogous to that of Example 1, step 1.20, intermediate 37.1 replacing intermediate 1.19. The crude was purified by CC (reverse phase, water/MeCN 95/5 to 20/80).

LC-MS: $t_R$=0.89; [M+H]$^+$: 533.46.

Example 38

4-((S)-2-{[4-((S)-3-methoxy-pyrrolidin-1-yl)-6-phenyl-pyridine-2-carbonyl]-amino}-4-phosphono-butyryl)-piperazine-1-carboxylic acid butyl ester

38.1. (S)-2-amino-4-bromo-butyric acid methyl ester

A solution of (S)-(+)-2-amino-4-bromobutyric acid hydrobromide salt (5 g) in a solution of 3M HCl in MeOH (57 mL) was refluxed for 20 h. The reaction mixture was evaporated off to afford after HV drying the desired compound as a brown oil (3.97 g).

LC-MS: $t_R$=0.27 min; [M+H]$^+$: 193.18.

38.2. (S)-2-benzyloxycarbonylamino-4-bromo-butyric acid methyl ester

To a suspension of intermediate 38.1 (3.95 g) in DCM/water (18 mL, 1/2) was added NaHCO$_3$ (2.6 g). The mixture was cooled to 0° C. and Cbz-Cl (2.48 mL) was added. The mixture was stirred at RT overnight. DCM/water was added and the phases were separated. The org. phase was dried (Na$_2$SO$_4$) and evaporated off to give the desired compound as a pale yellow oil (5.1 g).

LC-MS: $t_R$=0.97 min; [M+H]$^+$: 327.12.

38.3. (S)-2-benzyloxycarbonylamino-4-(diethoxy-phosphoryl)-butyric acid methyl ester This compound was prepared using a method analogous to that of Example 1, step 1.15, intermediate 38.2 replacing intermediate 1.14.

LC-MS: $t_R$=0.91 min; [M+H]$^+$: 388.44.

38.4. (S)-2-benzyloxycarbonylamino-4-(diethoxy-phosphoryl)-butyric acid

This compound was prepared using a method analogous to that of Example 1, step 1.16, intermediate 38.3 replacing intermediate 1.15.

LC-MS: $t_R$=0.84 min; [M+H]$^+$: 374.24.

38.5. 4-[(S)-2-benzyloxycarbonylamino-4-(diethoxy-phosphoryl)-butyryl]-piperazine-1-carboxylic acid butyl ester This compound was prepared using a method analogous to that of Example 1, step 1.17, intermediate 38.4 replacing intermediate 1.16 and intermediate 2.2 replacing 1-ethoxycarbonylpiperazine.

LC-MS: $t_R$=0.97 min; [M+H]$^+$: 542.40.

38.6. 4-[(S)-2-amino-4-(diethoxy-phosphoryl)-butyryl]-piperazine-1-carboxylic acid butyl ester This compound was prepared using a method analogous to that of Example 1, step 1.18, intermediate 38.5 replacing intermediate 1.17.

LC-MS: $t_R$=0.74 min; [M+H]$^+$: 408.55.

38.7. 4-((S)-4-(diethoxy-phosphoryl)-2-{[4-((S)-3-methoxy-pyrrolidin-1-yl)-6-phenyl-pyridine-2-carbonyl]-amino}-butyryl)-piperazine-1-carboxylic acid butyl ester This compound was prepared using a method analogous to that of Example 15, step 15.7, intermediate 38.6 replacing intermediate 15.2 and intermediate 1.10 replacing intermediate 15.6. The compound was however purified by preparative TLC (DCM/acetone 2/3).

LC-MS: $t_R$=0.90 min; [M+H]$^+$: 688.73.

38.8. 4-((S)-2-{[4-((S)-3-methoxy-pyrrolidin-1-yl)-6-phenyl-pyridine-2-carbonyl]-amino}-4-phosphono-butyryl)-piperazine-1-carboxylic acid butyl ester This compound was prepared using a method analogous to that of Example 1, step 1.20, intermediate 38.7 replacing intermediate 1.19.

LC-MS: $t_R$=0.79 min; [M+H]$^+$: 632.04.

Example 39

4-((R)-3-(Bis-acetoxymethoxy-phosphoryl)-2-{[4-((S)-3-methoxy-pyrrolidin-1-yl)-6-phenyl-pyridine-2-carbonyl]-amino}-propionyl)-piperazine-1-carboxylic acid butyl ester A solution of intermediate 22.2 (50 mg) and Et$_3$N (0.041 mL) in NMP (0.6 mL) was stirred 20 min at RT. Then, bromomethyl acetate (0.092 mL) was added followed by NaI (13 mg) and the reaction mixture was stirred overnight at 45° C. The reaction mixture was diluted with toluene and washed with water (5×). Each aq. layer was afterwards extracted with toluene (2×). The combined org. layers were dried over Na$_2$SO$_4$ and evaporated to dryness. CC (EA) gave 6 mg of the desired product.

LC-MS: $t_R$=0.91 min; [M+H]$^+$: 762.30.

Example 40

4-((R)-3-(Bis-ethoxycarbonyloxymethoxy-phosphoryl)-2-{[4-((S)-3-methoxy-pyrrolidin-1-yl)-6-phenyl-pyridine-2-carbonyl]-amino}-propionyl)-piperazine-1-carboxylic acid butyl ester A solution of intermediate 22.2 (100 mg) in abs. DMPU (0.3 mL) and NEt$_3$ (68 μL) was stirred for 10 min at RT. Then, chloromethyl ethyl carbonate (650 mg, prepared as described in WO2004092189) and NaI (29 mg) were added at RT, and the reaction mixture was stirred overnight at 50° C. The reaction mixture was diluted with H$_2$O and the aq. phase extracted with toluene. The combined organic layers were dried over Na$_2$SO$_4$ and concentrated to dryness. CC (EA) gave 19 mg of the desired product.

LC-MS: $t_R$=0.97 min; [M+H]$^+$: 822.32.

Example 41

N,N'-Bis-((S)-1-ethoxycarbonylethyl)-2-{(R)-[4-((S)-3-methoxy-pyrrolidin-1-yl)-6-phenyl-pyridine-2-carbonyl]-amino}-3-oxo-3-(4-butoxy-carbonyl-piperazin-1-yl)-propyl-phosphonic acid diamide A solution of intermediate 22.2 (200 mg), HCl H-Ala-OEt (149 mg) and NEt$_3$ (0.27 mL) in abs. pyridine (1 mL) was heated to 60° C. for 10 min. Then, a solution of aldrithiol-2 (2,2'-dipyridyl disulfide) (250 mg) and PPh$_3$ (297 mg) in abs. pyridine (1 mL) prestirred at RT for 10 min was added, and the reaction mixture heated at 60° C. overnight. The reaction mixture was diluted with brine 10 ml and extracted with DCM (3×). The combined organic layers were dried over Na$_2$SO$_4$ and concentrated to dryness. The residue was purified by CC (EA, then acetone) to give 48 mg of the desired product.

LC-MS: $t_R$=0.91 min; [M+H]$^+$: 816.40.

Example 42

4-[(R)-2-({6-Phenyl-4-[(tetrahydro-furan-3-yl)oxy]-pyridine-2-carbonyl}-amino)-3-phosphono-propionyl]-piperazine-1-carboxylic acid butyl ester 42.1. 6-Phenyl-4-(tetrahydro-furan-3-yloxy)-pyridine-2-carboxylic acid To sodium (118 mg) suspended in anh. THF (8 mL) was added 3-hydroxy-tetrahydrofurane (0.83 mL) at RT. The suspension was stirred for 30 min at RT, then 1 h at 65° C. A solution of intermediate 1.9 (400 mg) in anh. THF (8 mL) was added dropwise and the reaction mixture stirred for 3 d at 75° C. The solvent was then evaporated under reduced pressure and the residue taken up in H$_2$O. The aq. phase was washed with Et$_2$O (2×) and the aq. layer acidified to pH 2 with 25% HCl. The aq. phase was extracted with DCM (3×), and the combined organic phase dried over anh. Na$_2$SO$_4$, and concentrated to dryness. Purification by CC (reverse phase; eluent A: H$_2$O/TFA (1%); eluent B: MeCN/TFA (1%); gradient: 1 to 95% B) gave 80 mg of the desired product.

LC-MS: $t_R$=0.72 min; [M+H]$^+$: 286.29.

42.2. 4-[(R)-3-(Diethoxy-phosphoryl)-2-({6-phenyl-4-[(tetrahydro-furan-3-yl)oxy]-pyridine-2-carbonyl}-amino)-propionyl]-piperazine-1-carboxylic acid butyl ester To a solution of intermediate 42.1 (80 mg) and intermediate 15.2 (55 mg) in DCM/THF (0.7 mL, 4:1) was added DIPEA (48 μL) followed by HATU (106 mg), and the reaction mixture was stirred for 3.5 h at RT. Sat. aq. Na$_2$CO$_3$ was added and the aq. phase was extracted with DCM. The combined org. phases were dried over Na$_2$SO$_4$ and evaporated to dryness. Purification by CC (EA/MeOH 1:0 to 0:1) gave 39 mg of the desired product.

LC-MS: $t_R$=1.03 min; [M+H]$^+$: 661.64.

42.3. 4-[(R)-2-({6-Phenyl-4-[(tetrahydro-furan-3-yl)oxy-pyridine-2-carbonyl}-amino)-3-phosphono-propionyl]-piperazine-1-carboxylic acid butyl ester To a solution of intermediate 42.2 (36 mg) in MeCN (0.16 mL) was added trimethylsilyl bromide (0.141 mL) at 0° C. The reaction mixture was allowed to warm to RT and was stirred at RT overnight. H$_2$O (1 mL) was added and the mixture was stirred for 2 h at RT. The aq. phase was extracted 5× with DCM, the combined org. phases dried over MgSO$_4$ and concentrated to dryness. The crude was purified by CC (reverse phase; eluent A: H$_2$O; eluent B: MeCN; gradient: 5 to 80% B) and then by preparative TLC (DCM/MeOH 9:1 to 3:1) to give 2.2 mg of the desired product.

LC-MS: $t_R$=0.85 min; [M+H]$^+$: 605.15.

Biological Tests
P2Y$_{12}$ Receptor Binding Assay
Procedure

Chinese Hamster Ovary (CHO) cells with recombinant expression of the human P2Y$_{12}$ receptor were cultured in 24 well cell-culture plates. Cells were washed three times with binding buffer (50 mM Tris pH 7.4, 100 mM NaCl, 1 mM EDTA, 0.5% BSA). The cells were then incubated with 0.5 mL per well binding buffer containing tritium-labeled 2-methyl-thio-adenosine 5'-diphosphate (2-methyl-S-ADP) (between 100,000 and 300,000 dpm per well) and various concentrations of test compounds. After incubation at RT for 2 hours, cells were washed three times with binding buffer. Then, cells were solubilized by addition of 0.5 mL solubilization buffer (SDS, NaOH, EDTA). The content of each well was then transferred into beta-counter vials and 2.0 ml of Ultima Gold Scintillation liquid was added. After quantification of the cell-associated signal, extent of inhibition was calculated relative to maximal possible inhibition demonstrated by addition of excess of cold 2-methyl-S-ADP.

Results

Using the procedure described above for the $P2Y_{12}$ receptor binding assay, $IC_{50}$s ranging from 1 nM to 929 nM, with a arithmetic mean value of about 48 nM, were measured for the compounds of Examples 1 to 42.

For example, the following results could be obtained using the procedure described above for the $P2Y_{12}$ receptor binding assay:

| Example No. | $IC_{50}$ at $P2Y_{12}$ receptor binding assay (nM) |
| --- | --- |
| 12 | 186 |
| 14 | 30 |
| 17 | 19 |
| 20 | 5 |
| 24 | 1 |
| 31 | 4 |
| 36 | 2 |
| 39 | 3 |

The invention claimed is:

1. A compound of formula I

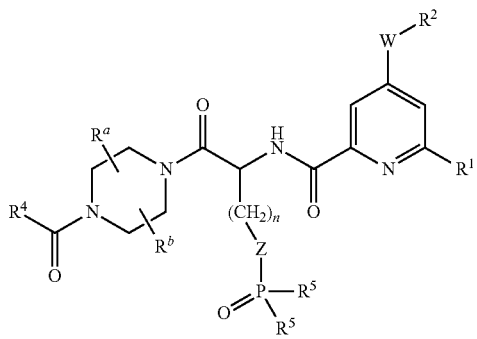

wherein
$R^1$ represents phenyl optionally substituted 1 to 3 times by substituents each independently selected from the group consisting of halogen, methyl, methoxy, trifluoromethyl and trifluoromethoxy;
W represents a bond and $R^2$ represents alkyl, cycloalkyl, aryl or heteroaryl; or
W represents —O— and $R^2$ represents alkyl, hydroxyalkyl, alkoxyalkyl or heterocyclyl; or
W represents —$NR^3$—, $R^2$ represents alkyl, carboxyalkyl, hydroxyalkyl, alkoxyalkyl, heterocyclyl, cycloalkyl, aryl or aralkyl and $R^3$ represents hydrogen or alkyl; or
W represents —$NR^3$— and $R^2$ and $R^3$ form, together with the nitrogen that carries them, a heterocyclic ring of 4 to 7 members wherein the members needed to complete said heterocyclic ring are each independently selected from —$CH_2$—, —$CHR^x$—, —O—, —S—, —CO— and —$NR^y$—, it being understood however that said heterocyclic ring does not contain more than one member selected from the group consisting of —$CHR^x$—, —O—, —S—, —CO— and —$NR^y$—, $R^x$ representing hydroxy, hydroxymethyl, alkoxymethyl or alkoxy and $R^y$ representing hydrogen or alkyl;
$R^a$ represents hydrogen or methyl;
$R^b$ represents hydrogen or methyl;
$R^4$ represents alkoxy;
$R^5$ represents hydroxy, $R^6$—$OCH_2O$— or $R^7$-alkyl-NH—;
$R^6$ represents alkylcarbonyl or alkoxycarbonyl;
$R^7$ represents alkoxycarbonyl;
n represents 0, 1, 2 or 3 and Z is a bond or n is 1 and Z is phenyl;
or a salt of such a compound.

2. The compound according to claim 1, that is also a compound of formula $I_P$

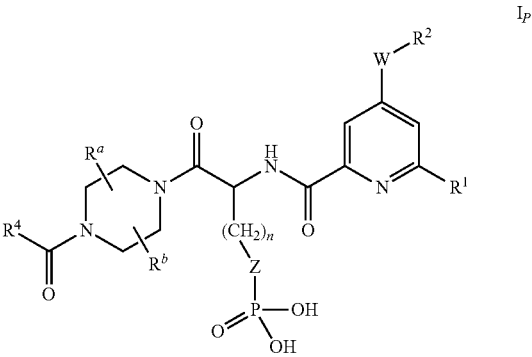

wherein
$R^1$ represents phenyl optionally substituted 1 to 3 times by substituents each independently selected from the group consisting of halogen, methyl, methoxy, trifluoromethyl and trifluoromethoxy:
W represents a bond and $R^2$ represents alkyl, cycloalkyl, aryl or heteroaryl; or
W represents —O— and $R^2$ represents alkyl, hydroxyalkyl, alkoxyalkyl or heterocyclyl; or
W represents —$NR^3$—, $R^2$ represents alkyl, carboxyalkyl, hydroxyalkyl, alkoxyalkyl, heterocyclyl, cycloalkyl, aryl or aralkyl and $R^3$ represents hydrogen or alkyl; or
W represents —$NR^3$— and $R^2$ and $R^3$ form, together with the nitrogen that carries them, a heterocyclic ring of 4 to 7 members wherein the members needed to complete said heterocyclic ring are each independently selected from —$CH_2$—, —$CHR^x$—, —O—, —S—, —CO— and —$NR^y$—, it being understood however that said heterocyclic ring does not contain more than one member selected from the group consisting of —$CHR^x$—, —O—, —S—, —CO— and —$NR^y$—, $R^x$ representing hydroxy, hydroxymethyl, alkoxymethyl or alkoxy and $R^y$ representing hydrogen or alkyl;
$R^a$ represents hydrogen or methyl;
$R^b$ represents hydrogen or methyl;
$R^4$ represents alkoxy;
n represents 0, 1, 2 or 3 and Z is a bond or n is 1 and Z is phenyl;
or a salt of such a compound.

3. The compound according to claim 1, wherein $R^1$ represents phenyl optionally substituted once by halogen, methyl, methoxy, trifluoromethyl or trifluoromethoxy;
or a salt of such a compound.

4. The compound according to claim 3, wherein each of $R^a$ and $R^b$ represents hydrogen;
or a salt of such a compound.

5. The compound according to claim 4, wherein W represents —NR$^3$— and $R^2$ and $R^3$ form, together with the nitrogen that carries them a heterocyclic ring of 5 to 6 members wherein the members needed to complete said heterocyclic ring are each independently selected from —CH$_2$—, —CHR$^x$—, —O— and —NR$^y$—, it being understood however that said heterocyclic ring does not contain more than one member selected from the group consisting of —CHR$^x$—, —O— and —NR$^y$—, R$^x$ representing hydroxy, hydroxymethyl or methoxy and R$^y$ representing methyl;
or a salt of such a compound.

6. The compound according to claim 5, wherein R$^5$ represents hydroxy;
or a salt of such a compound.

7. The compound according to claim 5, wherein R$^5$ represents R$^6$—OCH$_2$O— or R$^7$-alkyl-NH—;
or a salt of such a compound.

8. The compound according to claim 1, wherein W represents a bond;
or a salt of such a compound.

9. The compound according to claim 1, wherein W represents —O—;
or a salt of such a compound.

10. The compound according to claim 1, wherein W represents —NR$^3$—, R$^2$ represents alkyl, carboxyalkyl, hydroxyalkyl, alkoxyalkyl, heterocyclyl, cycloalkyl, aryl or aralkyl and R$^3$ represents hydrogen or alkyl, or wherein W represents —NR$^3$— and R$^2$ and R$^3$ form, together with the nitrogen that carries them, a heterocyclic ring of 4 to 7 members wherein the members needed to complete said heterocyclic ring are each independently selected from —CH$_2$—, —CHR$^x$—, —O—, —S—, —CO— and —NR$^y$—, it being understood however that said heterocyclic ring does not contain more than one member selected from the group consisting of —CHR$^x$—, —O—, —S—, —CO— and —NR$^y$—, R$^x$ representing hydroxy, hydroxymethyl, alkoxymethyl or alkoxy and R$^y$ representing hydrogen or alkyl;
or a salt of such a compound.

11. The compound according to claim 1, wherein R$^4$ represents (C$_2$-C$_4$)alkoxy;
or a salt of such a compound.

12. The compound according to claim 1, wherein R$^5$ represents R$^6$—OCH$_2$O— or R$^7$-alkyl-NH—;
or a salt of such a compound.

13. The compound according to claim 1, which is selected from the group consisting of:

4-((R)-2-{[4-((S)-3-methoxy-pyrrolidin-1-yl)-6-phenyl-pyridine-2-carbonyl]-amino}-4-phosphono-butyryl)-piperazine-1-carboxylic acid ethyl ester;

4-((R)-2-{[4-((S)-3-methoxy-pyrrolidin-1-yl)-6-phenyl-pyridine-2-carbonyl]-amino}-4-phosphono-butyryl)-piperazine-1-carboxylic acid butyl ester;

4-((R)-2-{[4-(4-methoxy-phenyl)-6-phenyl-pyridine-2-carbonyl]-amino}-3-phosphono-propionyl)-piperazine-1-carboxylic acid ethyl ester;

4-{(R)-2-[(6-phenyl-4-thiophen-3-yl-pyridine-2-carbonyl)-amino]-3-phosphono-propionyl}-piperazine-1-carboxylic acid ethyl ester;

4-{(R)-2-[(4,6-diphenyl-pyridine-2-carbonyl)-amino]-3-phosphono-propionyl}-piperazine-1-carboxylic acid ethyl ester;

4-{(R)-2-[(4-cyclopropyl-6-phenyl-pyridine-2-carbonyl)-amino]-3-phosphono-propionyl}-piperazine-1-carboxylic acid ethyl ester;

4-((R)-2-{[4-((R)-3-hydroxy-pyrrolidin-1-yl)-6-phenyl-pyridine-2-carbonyl]-amino}-3-phosphono-propionyl)-piperazine-1-carboxylic acid ethyl ester;

4-((R)-2-{[4-(2-methoxy-ethylamino)-6-phenyl-pyridine-2-carbonyl]-amino}-3-phosphono-propionyl)-piperazine-1-carboxylic acid ethyl ester;

4-((R)-2-{[4-(2-hydroxy-ethylamino)-6-phenyl-pyridine-2-carbonyl]-amino}-3-phosphono-propionyl)-piperazine-1-carboxylic acid ethyl ester;

4-[(R)-2-({4-[(2-methoxy-ethyl)-methyl-amino]-6-phenyl-pyridine-2-carbonyl}-amino)-3-phosphono-propionyl]-piperazine-1-carboxylic acid ethyl ester;

4-{(R)-2-[(4-benzylamino-6-phenyl-pyridine-2-carbonyl)-amino]-3-phosphono-propionyl}-piperazine-1-carboxylic acid ethyl ester;

4-(-2-{[4-((S)-3-methoxy-pyrrolidin-1-yl)-6-phenyl-pyridine-2-carbonyl]-amino}-2-phosphono-acetyl)-piperazine-1-carboxylic acid butyl ester;

4-((S)-2-{[4-((S)-3-methoxy-pyrrolidin-1-yl)-6-phenyl-pyridine-2-carbonyl]-amino}-5-phosphono-pentanoyl)-piperazine-1-carboxylic acid butyl ester;

4-((R)-2-{[4-((S)-3-methoxy-pyrrolidin-1-yl)-6-phenyl-pyridine-2-carbonyl]-amino}-5-phosphono-pentanoyl)-piperazine-1-carboxylic acid butyl ester;

4-((R)-2-{[6-(2-fluoro-phenyl)-4-phenyl-pyridine-2-carbonyl]-amino}-3-phosphono-propionyl)-piperazine-1-carboxylic acid butyl ester;

4-((R)-2-{[4-phenyl-6-(3-trifluoromethyl-phenyl)-pyridine-2-carbonyl]-amino}-3-phosphono-propionyl)-piperazine-1-carboxylic acid butyl ester;

4-((R)-2-{[6-(4-fluoro-phenyl)-4-phenyl-pyridine-2-carbonyl]-amino}-3-phosphono-propionyl)-piperazine-1-carboxylic acid butyl ester;

4-{(R)-2-[(4-phenyl-6-p-tolyl-pyridine-2-carbonyl)-amino]-3-phosphono-propionyl}-piperazine-1-carboxylic acid butyl ester;

4-((R)-2-{[4-((1S,2S)-2-methoxymethyl-cyclopropyl)-6-phenyl-pyridine-2-carbonyl]-amino}-3-phosphono-propionyl)-piperazine-1-carboxylic acid butyl ester;

4-((R)-2-{[4-((1S,2S)-2-hydroxymethyl-cyclopropyl)-6-phenyl-pyridine-2-carbonyl]-amino}-3-phosphono-propionyl)-piperazine-1-carboxylic acid butyl ester;

4-((R)-2-{[4-((S)-3-methoxy-pyrrolidin-1-yl)-6-phenyl-pyridine-2-carbonyl]-amino}-3-phosphono-propionyl)-piperazine-1-carboxylic acid ethyl ester;

4-((R)-2-{[4-((S)-3-methoxy-pyrrolidin-1-yl)-6-phenyl-pyridine-2-carbonyl]-amino}-3-phosphono-propionyl)-piperazine-1-carboxylic acid butyl ester;

4-((S)-2-{[4-((S)-3-methoxy-pyrrolidin-1-yl)-6-phenyl-pyridine-2-carbonyl]-amino}-3-phosphono-propionyl)-piperazine-1-carboxylic acid ethyl ester;

4-[(S)-2-{[4-((S)-3-methoxy-pyrrolidin-1-yl)-6-phenyl-pyridine-2-carbonyl]-amino}-3-(4-phosphono-phenyl)-propionyl]-piperazine-1-carboxylic acid ethyl ester;

4-{(R)-2-[(4-isopropyl-6-phenyl-pyridine-2-carbonyl)-amino]-3-phosphono-propionyl}-piperazine-1-carboxylic acid butyl ester;

4-{(R)-2-[(4-methoxy-6-phenyl-pyridine-2-carbonyl)-amino]-3-phosphono-propionyl}-piperazine-1-carboxylic acid butyl ester;

4-{(R)-2-[(6-phenyl-4-pyrrolidin-1-yl-pyridine-2-carbonyl)-amino]-3-phosphono-propionyl}-piperazine-1-carboxylic acid butyl ester;

4-((R)-2-{[4-(4-methyl-piperazin-1-yl)-6-phenyl-pyridine-2-carbonyl]-phosphonomethyl-amino}-acetyl)-piperazine-1-carboxylic acid butyl ester;

4-((R)-2-{[6-phenyl-(R)-4-(tetrahydro-furan-3-ylamino)-pyridine-2-carbonyl]-amino}-3-phosphono-propionyl)-piperazine-1-carboxylic acid butyl ester;

4-{(R)-2-[(2-hydroxymethyl-6'-phenyl-3,4,5,6-tetrahydro-2H-[1,4']bipyridinyl-2'-carbonyl)-amino]-3-phosphono-propionyl}-piperazine-1-carboxylic acid butyl ester;

4-{(R)-2-[(4-cyclopropylamino-6-phenyl-pyridine-2-carbonyl)-amino]-3-phosphono-propionyl}-piperazine-1-carboxylic acid butyl ester;

4-{(R)-2-[(6-phenyl-4-phenylamino-pyridine-2-carbonyl)-amino]-3-phosphono-propionyl}-piperazine-1-carboxylic acid butyl ester;

4-{(R)-2-[(6-phenyl-4-propylamino-pyridine-2-carbonyl)-amino]-3-phosphono-propionyl}-piperazine-1-carboxylic acid butyl ester;

4-((R)-2-{[4-(2-carboxy-ethylamino)-6-phenyl-pyridine-2-carbonyl]-amino}-3-phosphono-propionyl)-piperazine-1-carboxylic acid butyl ester;

4-((R)-2-{[4-(3-methoxy-pyrrolidin-1-yl)-6-phenyl-pyridine-2-carbonyl]-amino}-3-phosphono-propionyl)-3-methyl-piperazine-1-carboxylic acid ethyl ester;

4-((R)-2-{[4-(2-methoxy-ethoxy)-6-phenyl-pyridine-2-carbonyl]-amino}-3-phosphono-propionyl)-piperazine-1-carboxylic acid butyl ester;

4-{(R)-2-[(4-methyl-6-phenyl-pyridine-2-carbonyl)-amino]-3-phosphono-propionyl}-piperazine-1-carboxylic acid butyl ester; and 4-((5)-2-{[4-((S)-3-methoxy-pyrrolidin-1-yl)-6-phenyl-pyridine-2-carbonyl]-amino}-4-phosphono-butyryl)-piperazine-1-carboxylic acid butyl ester;

or a salt of such a compound.

14. The compound according to claim 1, which is selected from the group consisting of:

4-((R)-3-(Bis-acetoxymethoxy-phosphoryl)-2-{[4-((S)-3-methoxy-pyrrolidin-1-yl)-6-phenyl-pyridine-2-carbonyl]-amino}-propionyl)-piperazine-1-carboxylic acid butyl ester;

4-((R)-3-(Bis-ethoxycarbonyloxymethoxy-phosphoryl)-2-{[4-((S)-3-methoxy-pyrrolidin-1-yl)-6-phenyl-pyridine-2-carbonyl]-amino}-propionyl)-piperazine-1-carboxylic acid butyl ester;

N,N'-Bis-((S)-1-ethoxycarbonylethyl)-2-{(R)-[4-((S)-3-methoxy-pyrrolidin-1-yl)-6-phenyl-pyridine-2-carbonyl]-amino}-3-oxo-3-(4-butoxy-carbonyl-piperazin-1-yl)-propyl-phosphonic acid diamide; and 4-[(R)-2-({6-Phenyl-4-[(tetrahydro-furan-3-yl)oxy]-pyridine-2-carbonyl}-amino)-3-phosphono-propionyl]-piperazine-1-carboxylic acid butyl ester;

or a salt of such a compound.

15. A pharmaceutical composition containing at least one compound according to claim 1, or a pharmaceutically acceptable salt thereof, and one or more pharmaceutically acceptable carriers, diluents or excipients.

16. A method for treating myocardial infarction, arterial thrombosis, transient ischaemic attacks, peripheral vascular disease or stable or unstable angina, comprising administering to a subject a pharmaceutically active amount of a compound according to claim 1, or of a pharmaceutically acceptable salt thereof.

17. A method for treating thrombosis, comprising administering to a subject a pharmaceutically active amount of a compound according to claim 1, or of a pharmaceutically acceptable salt thereof.

18. A method for treating thrombosis, comprising administering to a subject a pharmaceutically active amount of a compound according to claim 6, or of a pharmaceutically acceptable salt thereof.

19. A method for treating thrombosis, comprising administering to a subject a pharmaceutically active amount of a compound according to claim 7, or of a pharmaceutically acceptable salt thereof.

* * * * *